US007371852B2

(12) United States Patent
Hardeman et al.

(10) Patent No.: US 7,371,852 B2
(45) Date of Patent: May 13, 2008

(54) ALKYL-LINKED NUCLEOTIDE COMPOSITIONS

(75) Inventors: Klass P. Hardeman, Chapel Hill, NC (US); Steven E. Hall, Chapel Hill, NC (US); Roy W. Ware, Raleigh, NC (US); Lindsay A. Hinkley, Raleigh, NC (US); Matthew G. Jenks, Durham, NC (US)

(73) Assignee: Serenex, Inc., Durham, NC (US)

( * ) Notice: Subject to any disclaimer, the term of this patent is extended or adjusted under 35 U.S.C. 154(b) by 464 days.

(21) Appl. No.: 10/762,078

(22) Filed: Jan. 21, 2004

(65) Prior Publication Data

US 2004/0215009 A1    Oct. 28, 2004

Related U.S. Application Data

(60) Provisional application No. 60/453,697, filed on Jan. 22, 2003, provisional application No. 60/532,134, filed on Dec. 23, 2003.

(51) Int. Cl.
C07H 21/00       (2006.01)
G01N 33/566    (2006.01)
G01N 33/543    (2006.01)

(52) U.S. Cl. ............... 536/25.3; 536/25.33; 536/26.22; 536/26.23; 536/26.26; 536/26.7; 536/26.8; 436/501; 436/518

(58) Field of Classification Search ............... 536/25.3, 536/25.33, 26.22, 26.23, 26.26, 26.7, 26.8
See application file for complete search history.

(56) References Cited

U.S. PATENT DOCUMENTS

| 4,529,796 | A |   | 7/1985  | Kang et al. |
| 4,988,680 | A |   | 1/1991  | Halazy et al. |
| 5,536,822 | A |   | 7/1996  | Haystead |
| 5,650,510 | A |   | 7/1997  | Webb, II et al. |
| 5,780,617 | A |   | 7/1998  | Van den Bosch et al. |
| 5,854,228 | A |   | 12/1998 | Webb, II et al. |
| 5,976,492 | A | * | 11/1999 | Griffiths et al. ............ 424/1.49 |
| 5,981,507 | A | * | 11/1999 | Josephson et al. ............ 514/48 |
| 2004/0241649 | A1 | * | 12/2004 | Huang ............................ 435/6 |

FOREIGN PATENT DOCUMENTS

| EP | 0269947 B2 | 6/1988 |
| EP | 0338887 B1 | 10/1999 |
| WO | WO00/63694 A1 * | 10/2000 |

OTHER PUBLICATIONS

Trayer et al., "Preparation of Adenosine Nucleotide Derivatives Suitable for Affinity Chromatography," Biochemical Journal, 139, 609-623 (1974).*
Peters et al., "Chemical Crosslinking: Reagents and Problems in Studies of Membrane Structure," Annual Reviews in Biochemistry, 46, 523-551 (1977).*
Van Aeroschot et al., "Silica Gel Functionalised with Different Spacers as Solid Support for Oligonucleotide Synthesis," Nucleosides & Nucleotides, 7(1), 75-90 (1988).*
Google of "proteome," See <http//en.wikipedia.org/wiki/Proteome>, accessed on Sep. 20, 2006.*
Shibaev et al., "New Affinity-Chromatography Adsorbents Derived From Uridine Nucleotide Phosphoryl Amides," Bioorganicheskaya Khimiya, 3(1), 120-126 (1977): Chemical Abstracts, 86, 1216783 (1977); only Abstract supplied.*
Shibaev et al., "New Affinity-Chromatography Adsorbants Derived From Uridine Nucleotide Phosphoryl Amides," Bioorganicheskaya Khimiya, 3(1), 120-126 (1977): Chemical Abstracts, 86, 1216783 (1977).*
Haystead et al., "[gamma]-Phosphate-linked ATP-Sepharose for the Afinity Purification of Protein Kinases—Rapid Purification to Homogeneity of Sketetal Muscle Mitogen-Activated Protein Kinase Kinase," European Journal of Biochemistry, 214(2), 459-467 (Jun. 1993).*
Bressi, J.C., et al., "Adenosine Analogues as Selective Inhibitors of Glyceraldehyde-3-phosphate Dehydrogenase of *Trypanosomatidae* via Structure-Based Drug Design," *J. Med. Chem.* 2001, pp. 2080-2093, vol. 44.
Chang, Y.-T., et al., "Synthesis and Application of Functionally Diverse 2,6,9-Trisubstituted Purine Libraries as CDK Inhibitors," *Chemistry Biology* Jun. 1999; pp. 361-375, vol. 6, No. 6.
Halbfinger, E., et al., "Molecular Recognition of Modified Adenine Nuceotides by the $P2Y_1$-Receptor. 1. A Synthetic, Biochemical, and NMR Approach," *J. Med. Chem.* 1999, pp. 5325-5337, vol. 42, No. 26.
Hernandez, A-I., et al., "Acyclic Nucleotide Analogues as Novel Inhibitors of Human Mitochondrial Thymidine Kinase," *J. Med. Chem.* 2002, pp. 4254-4263, vol. 45, No. 19.
Huryn, D.M., et al., "Synthesis of ISO-DDA, Member of a Novel Class of Anti-HIB Agents," *Tetrahedron Letters* 1989, pp. 6259-6262, vol. 30, No. 46, Printed in Great Britain by Pergamon Press plc.
Van Tilburg, E.W., et al., "$N^6$, 5'-Disubstituted Adensine Derivatives as Partial Agonists for the Human Adenosine $A_3$ Receptor," *J. Med. Chem.* 1999, pp. 1393-1400, vol. 42, No. 8.
Guiller, F., et al., "Linkers and Cleavage Strategies in Solid-Phase Organic Synthesis and Combinatorial Chemistry," *Chem. Rev. 2000*, pp. 2091-2157, vol. 100, No. 6 (XP-002248255).
Kumar, P., et al., "A Versatile Solid Phase Method for the Synthesis of Oligonucleotide-3'-Phosphates," *Tetrahedron Letters*, 1991, pp. 967-970, vol. 32, No. 7 (XP-002112931).
Vyle, J.S., et al., "A Novel Solid Support for Synthesis of 2', 3'-Cyclic Phosphate Terminated Oligonucleotides," *Tetrahedron Letters*, 1998, pp. 7975,7978, vol. 39 (XP004137857).
Graves, P.R., et al., "Discovery of Novel Targets of Quinoline Drugs in the Human Purine Binding Proteome," *Molecular Pharmacology*, 2002, pp. 1364-1372, vol. 62(6).

* cited by examiner

*Primary Examiner*—L. E. Crane
(74) *Attorney, Agent, or Firm*—Alston & Bird LLP

(57) ABSTRACT

Alkyl-linked nucleotide non-homogeneous solid supports and nucleotide affinity media comprising an alkyl-linked nucleotide are provided. The linker is generally a hydrophobic linker that can be a 3, 4, 5, 6, 7, 8, 9, 10, or a longer carbon chain. Also included in the invention are methods for synthesis of an alkyl-linked nucleotide, nucleotide affinity media and methods of use thereof for affinity chromatography and screening methods.

12 Claims, 5 Drawing Sheets

ALKYL-LINKED NUCLEOTIDE COMPOSITIONS

CROSS-REFERENCE TO RELATED APPLICATIONS

This application claims the benefit of U.S. Provisional Applications 60/453,697, filed Jan. 22, 2003, and 60/532,134, filed Dec. 23, 2003, each of which are hereby incorporated in its entirety by reference herein.

FIELD OF THE INVENTION

The present invention relates to nucleotide affinity media and methods for their use.

BACKGROUND OF THE INVENTION

Previous methods of preparing ligands, such as nucleotides, for use in affinity chromatography have typically coupled the nucleotide to a solid matrix through the N6 amino group on the purine ring, or via a hydroxyl group of the ribose moiety. However, these ligands are not always effective ligands for affinity chromatography, usually because of steric hindrance or the orientation of the ligand on the solid matrix. The studies of the molecular structures of some nucleotide binding proteins, such as kinases, support these findings.

Recently, in an alternative method, the nucleotide, adenosine triphosphate (ATP), was coupled to an affinity resin indirectly through the gamma-phosphate group of ATP via an aminophenyl moiety. Linking ATP to a resin via an aminophenyl group attached to the gamma-phosphate of ATP has advantages over earlier nucleotide affinity media.

However, a need still exists to develop a still more efficient method for synthesis of nucleotide affinity media that are suitable for use in affinity chromatography and screening methods.

SUMMARY OF THE INVENTION

The present invention is directed to alkyl-linked nucleotide non-homogeneous solid supports, which include alkyl-linked nucleotide affinity media.

In one embodiment, an alkyl-linked nucleotide non-homogeneous solid support has the general formula:

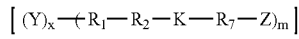

such that: Y is a solid support, a tag, or a protective group; x is either 0 or 1; $R_1$ is a covalent bond between Y and $R_2$, or $R_1$ is an acyl group, a substituted or a non-substituted group and the substituted or non-substituted group is selected from an alkyl, cycloalkyl, heteroalkyl, heterocycloalkyl, aryl, or a heteroaryl group, or a combination of these groups; $R_2$ is a substituted or a non-substituted group, and the substituted or non-substituted group is selected from an alkyl, cycloalkyl, heteroalkyl, heterocycloalkyl, or a heteroaryl group, or a combination of these groups; K is a heteroatom; $R_7$ is $(P)_n$ where P is a phosphate or thiophosphate and n is at least one or $R_7$ is a phosphate group mimic, Z is a nucleoside or nucleoside derivative; and m is at least one.

Also included in the invention is a method to synthesize an alkyl-linked nucleotide non-homogeneous solid support comprising an alkyl-linked nucleotide affinity medium, said alkyl-linked nucleotide affinity medium having a general formula:

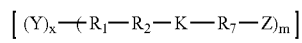

comprising the general steps of (a) coupling at least one linker to a solid support or tag in a suitable coupling buffer, wherein the linker is $R_2$, or a combination of $R_1$ and $R_2$; (b) end-capping reactive sites remaining on the solid support or tag after the coupling step; and (c) reacting a terminal phosphate or thiophosphate group of a nucleotide with the linker coupled to the solid support or tag, wherein Y is a solid support or a tag; x=1; $R_1$ is a covalent bond between Y and $R_2$, or $R_1$ is an acyl group, a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof; $R_2$ is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof; K is a heteroatom; $R_7$ is $(P)_n$ where P is a phosphate or thiophosphate and n is at least one or $R_7$ is a phosphate group mimic, Z is a nucleoside or nucleoside derivative; and m is at least one.

Also included in the invention is a method for screening compounds. For example, the method comprises the steps of (a) contacting a proteome with a nucleotide affinity medium comprising a general formula:

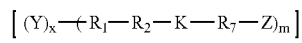

wherein Y is a solid support or a tag; x=1; $R_1$ is a covalent bond between Y and $R_2$, or $R_1$ is an acyl group, a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof; $R_2$ is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof; K is a heteroatom; $R_7$ is $(P)_n$ where P is a phosphate or thiophosphate and n is at least one or $R_7$ is a phosphate group mimic, Z is a nucleoside or nucleoside derivative; and m is at least one; (b) washing the nucleotide affinity medium with a buffer, whereby non-specifically bound components of the proteome are eluted from the nucleotide affinity medium and specific components of the proteome remain bound to the nucleotide affinity medium; (c) contacting the nucleotide affinity medium bound to specific components of the proteome with at least one test compound; (d) eluting from the nucleotide affinity medium components of the proteome that are specifically displaced by the test compound; and (e) identifying the components of the proteome that are specifically displaced by the test compound from the nucleotide affinity medium.

The alkyl-linked nucleotide non-homogeneous solid supports and alkyl-linked nucleotide affinity media as described herein are particularly useful, for example, as affinity ligands in affinity chromatography methods, for the screening of proteomes or combinatorial libraries, and for the purification of compounds such as, for example, proteins. Furthermore, the invention includes a more efficient method for the synthesis of such alkyl-linked nucleotides and nucleotide affinity media than has been previously accomplished.

DETAILED DESCRIPTION OF THE INVENTION

Figure 1:
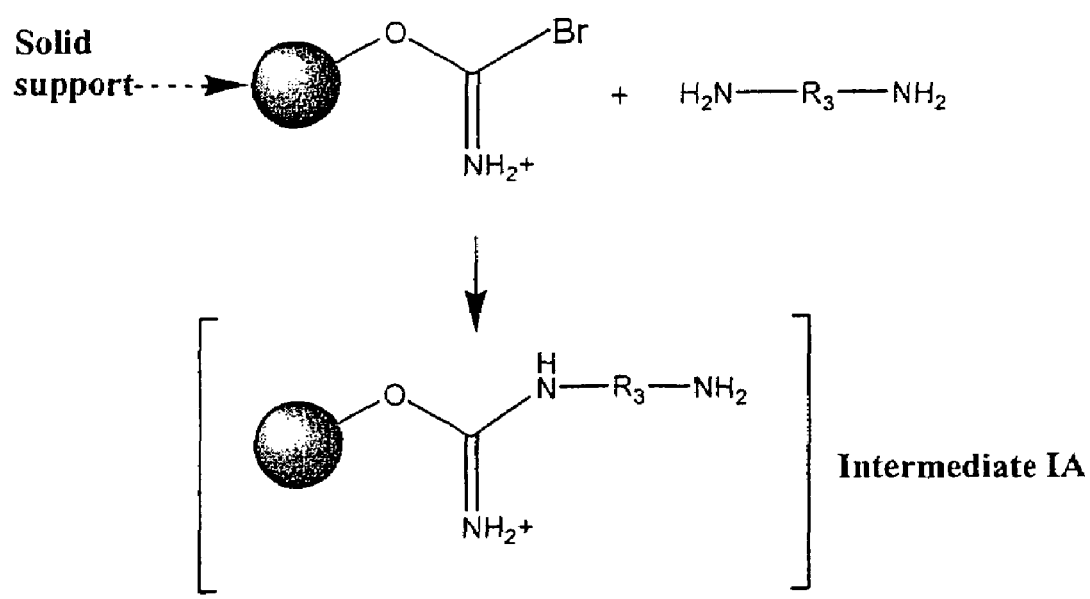
FIG. 1 is a schematic of the synthesis of a compound Intermediate IA using cyanogen bromide-activated beaded agarose and a linker.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to an alkyl-linked nucleotide non-homogeneous solid support comprising the general formula:

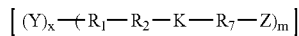

I wherein Y is a solid support, a tag, or a protective group; x=0 or 1; $R_1$ is a covalent bond between Y and $R_2$, or $R_1$ is an acyl group, a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof; $R_2$ is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof; K is a heteroatom; $R_7$ is $(P)_n$ where P is a phosphate or thiophosphate and n is at least one or $R_7$ is a phosphate group mimic, Z is a nucleoside or nucleoside derivative; and m is at least one.

Such substituted and non-substituted alkyl, cycloalkyl, heteroalkyl, heterocycloalkyl, aryl, heteroaryl groups, and combinations of same, can be linear or branched chains, as will be understood by one of skill in the art.

A "heteroaryl," as that term is used herein, is an aryl group that includes at least one aromatic ring structure in which one or more of the atoms of at least one of the aromatic rings is an element other than carbon, for example, sulfur, nitrogen or oxygen. Examples of heteroaromatic compounds include pyridine, pyrimidine, oxazole, quinoline, thiophene and furan.

A heteroatom (K) is preferably a nitrogen atom (N), an oxygen atom (O), or a sulfur atom (S). Preferably, the heteroatom (K) is a nitrogen atom.

An alkyl-linked nucleotide is also referred to herein as a ligand or an affinity ligand.

An alkyl-linked nucleotide bound to a solid support or a tag, such that the solid support or tag is suitable for the separation of the alkyl-linked nucleotide, and optionally, compounds (such as proteins, for example) bound to the alkyl-linked nucleotide, from unbound compounds, is also referred to herein as a "nucleotide affinity medium or media", or as an "alkyl-linked nucleotide affinity medium or media".

A solid support (Y) can be any suitable support, such as a resin, or a particulate material, such as a bead, or a particle. Alternatively, a solid support can be a continuous solid surface, such as a plate, chip, well, channel, column or a tube. The material of a solid support will be of any suitable substance, compound or polymer, as will be appreciated by one of skill in the art. Examples include, without limitation, acrylamide, agarose, methacrylate polymers, methacrylate copolymers, cellulose, nylon, silica, glass, ceramic, a magnetized particle or surface, nitrocellulose, polystyrene, thermoresponsive polymers (see, for example, Lee, et al. (1996) *Journal of Applied Polymer Science* 62: 301-311; Yoshida, et. al. (1996) *Macromolecules* 29:8987-89; and Osada and Khokhlov, eds. (2001) *Polymer Gels and Networks* (Marcel Dekker, New York); each of which is herein incorporated by reference in its entirety), and derivatives thereof.

In one embodiment, the solid support (Y) is a SEPHACRYL™ resin. SEPHACRYL™ is an acrylamide derivative, produced by polymerizing allyl dextran with the cross-linking monomer N,N'-methylene-bisacrylamide.

In another embodiment, the solid support (Y) is a TOYOPEARL® resin. TOYOPEARL® is a methacrylate derivative, produced by the co-polymerization of glycidyl methacrylate, pentaerythritol dimethylmethacrylate and polyethylene glycol.

In one embodiment, the solid support (Y) is a beaded agarose. An example of a suitable beaded agarose is SEPHAROSE™ beaded agarose. Beaded agarose, such as SEPHAROSE™ beaded agarose, can be a cross-linked preparation, such as will be appreciated by one of skill in the art. Cross-linked preparations are generally recognized to have good chemical and physical stability properties. The choice of a suitable solid support will be apparent to one of skill in the art from the known characteristics of a solid support and the method of use of that solid support.

Agarose is a linear polymer with a basic structure as follows:

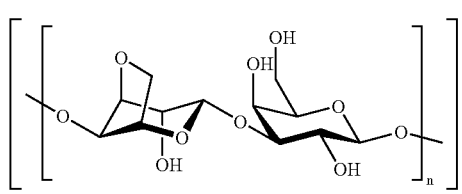

XXIV wherein v is at least one. Variations of this basic structure of agarose will be recognized by one of skill in the art. The preparation and use of solid supports, such as agarose, are well known in the art (see, for example, Cuatrecasas and Anfinsen, "Affinity Chromatography" in Ann. Rev. Biochem. Snell et al., eds. (CA: Annual Reviews Inc.), 40: 259-278 (1971), the teachings of which are incorporated herein by reference in their entirety).

As used herein, a tag is an agent that provides for the specific detection or capture of the alkyl-linked nucleotide. For example, and without limitation, a suitable tag is biotin, avidin, streptavidin, a hapten, a fluorophore or a chromophore. Detection or capture of the alkyl-linked nucleotide employs techniques that are standard in the art. For example, a biotin-tagged alkyl-linked nucleotide can be captured using avidin, streptavidin or related avidin derivatives. The biotin-avidin interaction is highly specific. An avidin-conjugated agent used to detect or capture a biotin-tagged alkyl-linked nucleotide can be soluble (for example, an antibody), or a particulate material (for example, beaded agarose or a magnetized particle), or a continuous surface (for example, a plate or well coated with avidin). Detection and capture of a hapten-tagged alkyl-linked nucleotide can be achieved, for example, using hapten-specific antibodies. Visual detection methods for fluorophore or chromophore-tagged alkyl-linked nucleotides are readily understood by one of skill in the art.

Protective groups are well-known and standard in the art. The selection of a protective group will be dependent upon the properties of the reactive group, the conditions in which the compound is to be used and the function that is desired. These are readily understood by those of skill in the art (see, generally, "Protective Groups in Organic Synthesis" Greene and Wuts, eds. (NY: John Wiley & Sons, Inc.) 3rd edition (1999), the teachings of which are incorporated herein by reference in their entirety). Protective groups are used to selectively protect reactive groups such as hydroxyl, amino, carboxyl, carbonyl, sulfhydryl, and phosphate groups.

$R_1$ can be a covalent bond, or when $R_1$ is not a covalent bond, $R_1$ is also referred to herein as a linker or linker arm. $R_2$ is also referred to herein as a linker or a linker arm. A linker can be selected from any suitable alkyl, heteroalkyl, cycloalkyl, heterocycloalkyl, aryl, heteroaryl, substituted, non-substituted, linear or branched group, or a combination of same. Generally, the linker is a hydrophobic linker. For example, the linker can be a 3, 4, 5, 6, 7, 8, 9, 10, or longer carbon chain. Furthermore, a linker used in the invention can be highly hydrophobic or moderately hydrophobic, as will be understood by one of skill in the art. Alternatively, a hydrophilic linker can be used.

In one embodiment, $R_1$ comprises:

XXIX wherein Q=O or $NH_2+$.

In another embodiment, $R_1$ comprises:

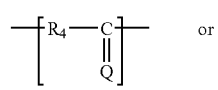

XXVI

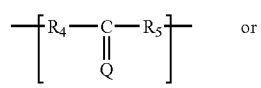

XXVII

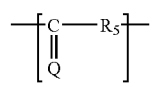

XXVIII wherein Q=O or $NH_2+$; $R_4$ is a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof; and $R_5$ is a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof.

In one embodiment, $R_2$ comprises the general formula:

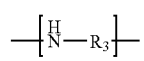

XXV wherein $R_3$ is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

Examples of suitable linkers include, without limitation:

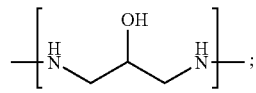

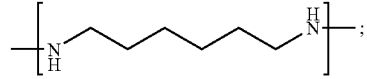

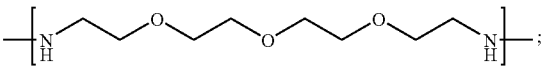

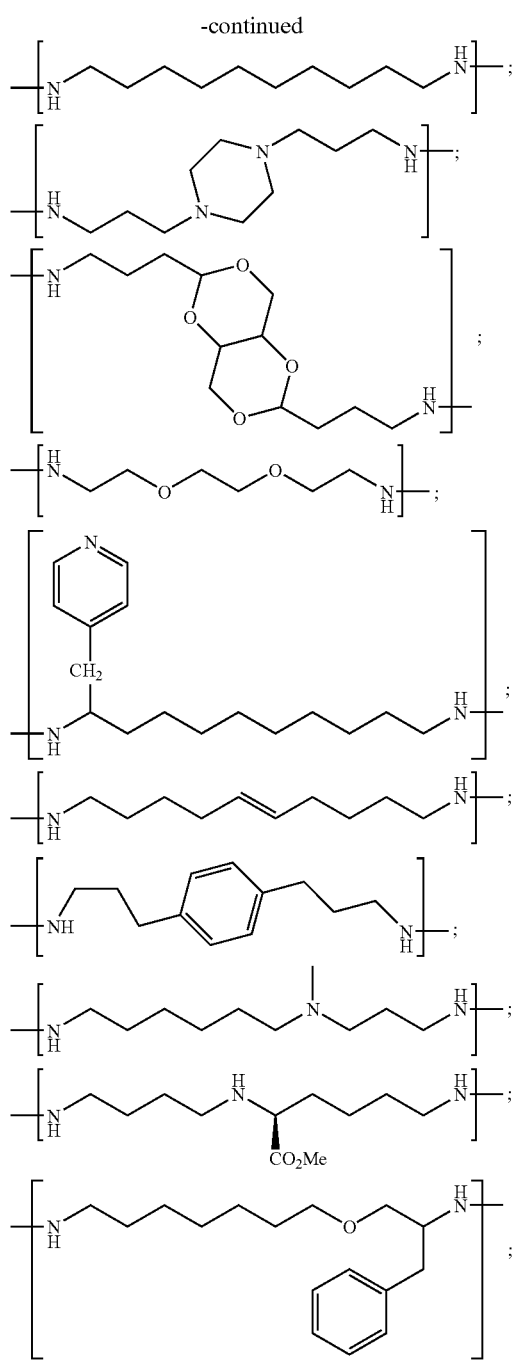

Furthermore, a linker, such as described above, can be attached (for example, via a condensation reaction) to another linker to form a larger and/or a longer linker. For example, a linker can be formed by the tandem synthesis of linkers in a linear configuration. This can be represented, for example, as:

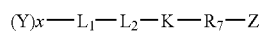

where Y is a solid support, a tag or a protective group, x is 0 or 1; $L_1$ and $L_2$ are linkers, such as provided in the above examples, and they can be the same or different linkers; K is a heteroatom; $R_7$ is $(P)_n$ where P is a phosphate or thiophosphate and n is at least one or $R_7$ is a phosphate group mimic, and Z is a nucleoside or nucleoside derivative. As shown in the above examples, two linkers can be synthesized in tandem, however, it will be understood that two, three, or more linkers, can be synthesized in tandem. Alternatively, a branched configuration of linkers can be synthesized. Again, the linkers can be the same or different. Different linkers can be chosen according to their different hydrophobic or hydrophilic properties, as will be understood by one of skill in the art.

Additionally or alternatively, more than one alkyl-linked nucleotide can be bound to Y, for example when Y is a solid support, by more than one type of linker. Again, different linkers can be chosen according to their different hydrophobic or hydrophilic properties, as will apparent to one of skill in the art. Thus, for example, when Y is a solid support, more than one nucleotide or nucleotide derivative (which may be the same nucleotide or different nucleotides, for example, only ATP, or a mixture of AMP and ADP, etc.) can be bound to the solid support by linkers that have similar or different hydrophobic properties (or hydrophilic properties). Examples of suitable synthesis methods for these affinity media are provided in the exemplification.

In some embodiments of the invention, $R_7$ is $(P)_n$ where P is a phosphate or thiophosphate group and $n \geq 1$. Examples of suitable phosphate and thiophosphate groups that may be used include, without limitation:

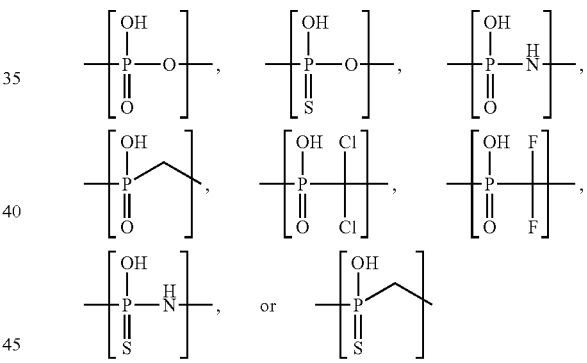

As will be understood by one of skill in the art, phosphate and thiophosphate groups can also be present in an ionized variant or salt form. In some embodiments of the invention n is $\geq 1$, $\geq 2$, $\geq 3$, or $\geq 4$. For example, n can be 1, 2, 3, or 4. When n>1, any combination of phosphate or thiophosphate groups may be used.

In other embodiments of the invention, $R_7$ is a phosphate group mimic. For example, in some embodiments, $R_7$ is a carboxylic acid that contains 4-8 carbons in the main chain and optionally contains a heteroatom. Examples of suitable carboxylic acids include, without limitation:

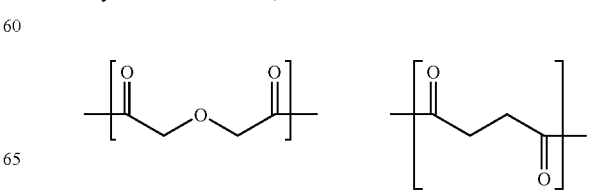

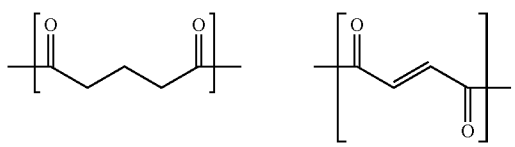

Accordingly, in some embodiments the alkyl linked nucleotide compositions have a general formula selected from:

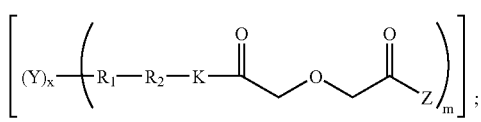

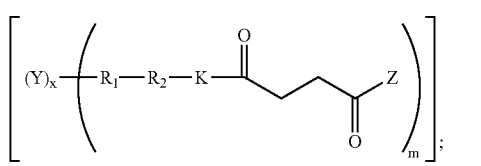

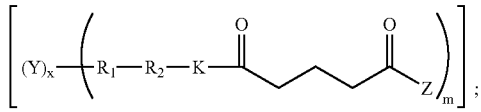

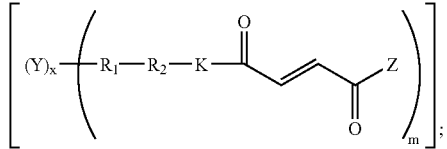

Other phosphate group mimics that may be used according to the invention include, without limitation, the following:

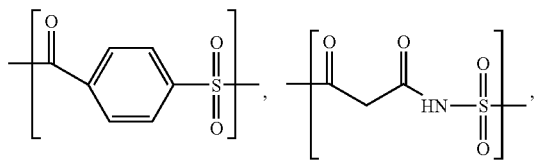

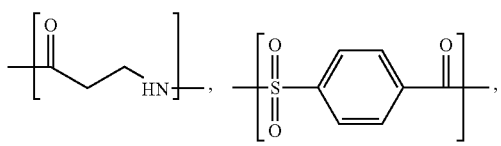

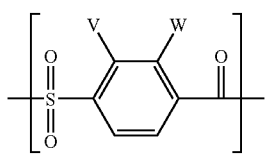

where V and W can be H or a heteroatom such as $NH_2$ or OH,

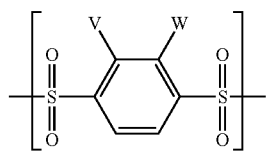

where V and W can be H or a heteroatom such as $NH_2$ or OH,

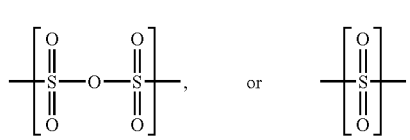

A nucleoside and a nucleotide, as referred to herein, can be naturally-occurring or non-naturally-occurring. Furthermore, the nucleoside or nucleotide can be biologically or synthetically-derived using techniques that are standard to one of skill in the art. Suitable nucleosides include, without limitation, adenosine (A), guanosine (G), cytidine (C), thymidine (T) and uridine (U), and derivatives and analogs thereof.

Nucleotides are nucleosides with at least one phosphate group (or thiophosphate group), for example, a monophosphate, diphosphate or triphosphate group. The nucleotide can have phosphate or thiophosphate groups, or a combination of both. The number of phosphate or thiophosphate groups is at least one, and can be one, two, three or more in number. Such nucleotides are often referred to in abbreviation, for example, AMP, ADP, ATP, GMP, GDP, GTP, etc., as is understood by one of skill in the art.

In one embodiment, the nucleotide is a monophosphate, diphosphate, or triphosphate of adenosine, guanosine, cytidine, thymidine, or uridine.

Nucleoside and nucleotide derivatives and analogs are also encompassed by the invention. The isolation or synthesis of nucleoside derivatives and analogs are accomplished using techniques that are standard in the art, see for example, Guranowski et al. (1981) Biochemistry 20:110-15; Yaginuma et al. (1981) *J. Antibiot.* 23:359-66; Robins et al. (1983) *J. Am. Chem. Soc.* 105:4059-65; Borchardt et al. (1984) *J. Biol. Chem.* 259:5353-58; De Clercq et al. (1987) *Biochem. Pharmacol.* 36:2567-75; Seela et al. (1991) *Helv. Chim. Acta* 74:1048; Franchetti et al., (1994) *J. Med. Chem.* 37: 3534-3541; Van Calenberg et al. (1994) *Helv. Chim. Acta.* 77:631-44; Picher et al. (1996) *Biochem. Pharmacol.* 51:1453-601; Rosse et al. (1997) *Helv. Chim. Acta.* 80:653; Cowart et al. (1999) *J. Org. Chem.* 64:2240-49. Fischer et al., (1999) *J. Med. Chem.* 42:3636-3646; van Tilburg et al. (1999) *J. Med. Chem.* 43:1393-400; Halbfinger et al., (1999) *J. Med. Chem.* 42:5325-5337; Ingall et al. (1999) *J. Med. Chem.* 42:213-20; Gendron et al., (2000) *J. Med. Chem.* 43:2239-2247; Loog et al. (2000) *FEBS Letters* 480:244; Bressi et al. (2001) *J. Med. Chem.* 44:2080-93; Herforth et al. (2002) *J. Comb. Chem.* 4:302-14; Hernandez et al. (2002) *J. Med. Chem.* 45:4254-63; Parang et al. (2002) *Pharmacology and Therapeutics* 93:145; Xu et al. (2002) *J. Med. Chem.* 45:5694-709; Hocek and Dvorakova (2003) *J. Org. Chem.* 68:5773-6; Koroniak et al. (2003) *Pharmacology & Therapeutics* 93:145; and Kourafalos et al. (2003) *J. Org.*

Chem. 68:6466-69; the teachings of all of which are incorporated herein by reference in their entirety.

In one embodiment, the invention includes an alkyl-linked nucleotide non-homogeneous solid support comprising an alkyl-linked adenosine, said alkyl-linked nucleotide non-homogeneous solid support comprising the general structure:

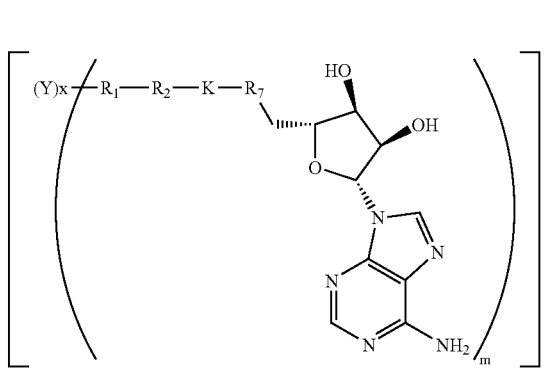

or an ionized variant or a salt thereof.

In another embodiment is an alkyl-linked nucleotide non-homogeneous solid support comprising an alkyl-linked guanosine, said alkyl-linked nucleotide non-homogeneous solid support comprising the general structure:

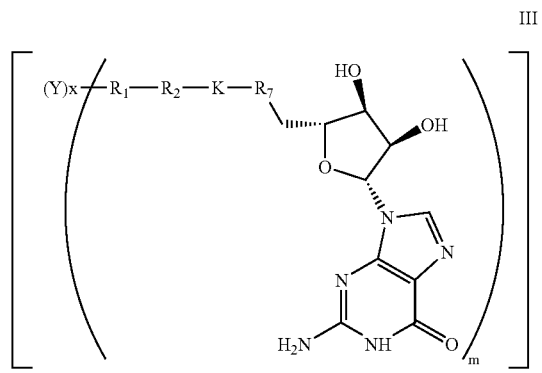

or an ionized variant or a salt thereof.

In another embodiment is an alkyl-linked nucleotide non-homogeneous solid support comprising an alkyl-linked thymidine, said alkyl-linked nucleotide non-homogeneous solid support comprising the general structure:

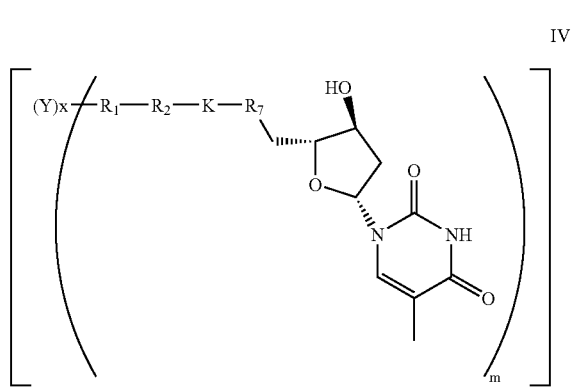

or an ionized variant or a salt thereof.

In a further embodiment is an alkyl-linked nucleotide non-homogeneous solid support comprising an alkyl-linked cytidine, said alkyl-linked nucleotide non-homogeneous solid support comprising the general structure:

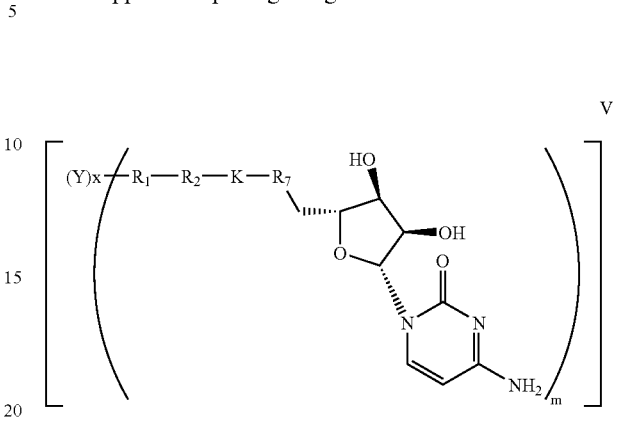

or an ionized variant or a salt thereof.

In yet another embodiment is an alkyl-linked nucleotide non-homogeneous solid support comprising an alkyl-linked uridine, said alkyl-linked nucleotide non-homogeneous solid support comprising the general structure:

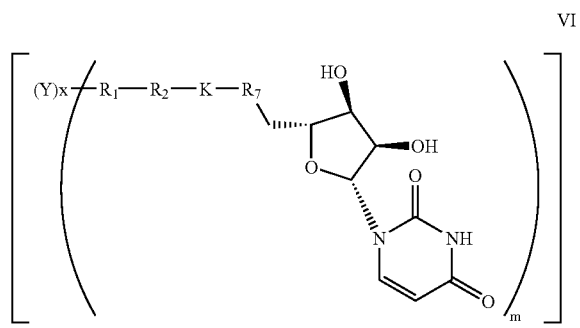

or an ionized variant or a salt thereof.

In another embodiment, the invention includes an alkyl-linked adenosine comprising the general structure:

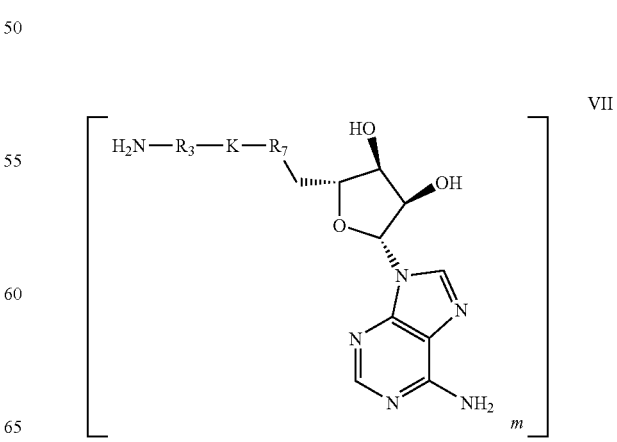

or an ionized variant or a salt thereof, wherein the linker (R$_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In further embodiment, the invention includes an alkyl-linked guanosine, comprising the general structure:

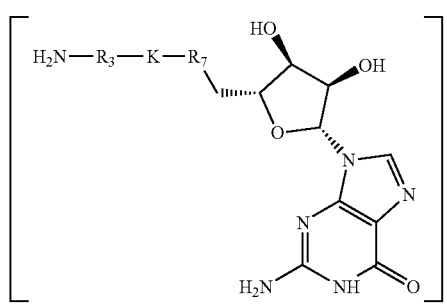

VIII or an ionized variant or a salt thereof, wherein the linker (R$_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked thymidine comprising the general structure:

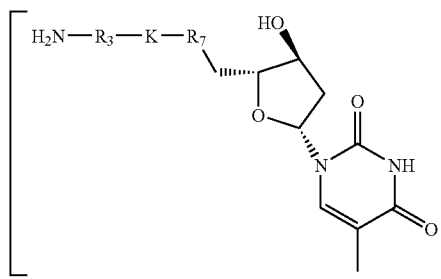

IX or an ionized variant or a salt thereof, wherein the linker (R$_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In yet another embodiment, the invention includes an alkyl-linked cytidine comprising the general structure:

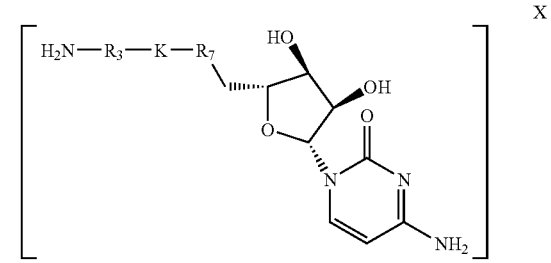

X or an ionized variant or a salt thereof, wherein the linker (R$_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In a further embodiment, the invention includes an alkyl-linked uridine comprising the general structure:

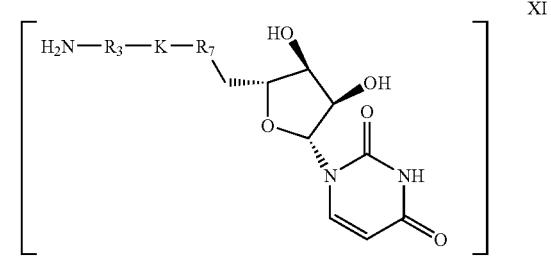

XI or an ionized variant or a salt thereof, wherein the linker (R$_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked 2'-deoxy-adenosine comprising the general structure:

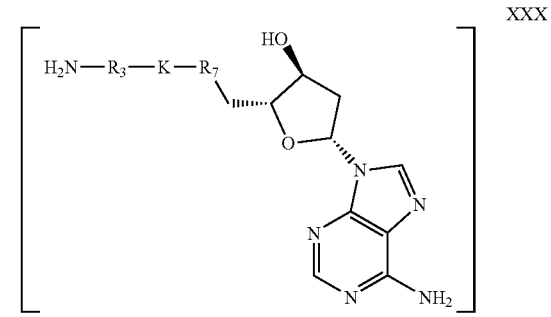

XXX or an ionized variant or a salt thereof, wherein the linker (R$_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked 3'-deoxy-adenosine comprising the general structure:

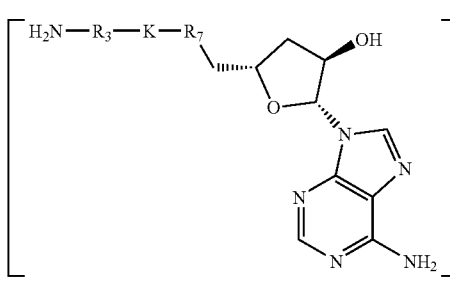

XXXI or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked 2'-deoxy-2'-amino-adenosine comprising the general structure:

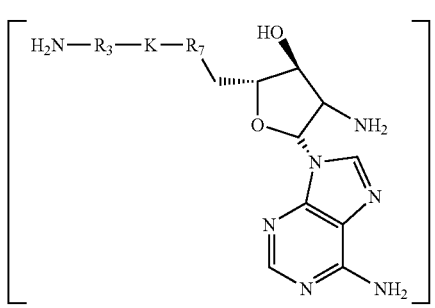

XXXII or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked 3'-deoxy-3'-amino-adenosine comprising the general structure:

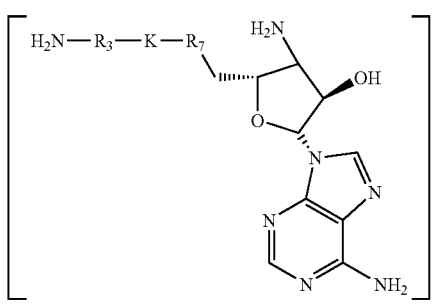

XXXIII or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked adenosine derivative, Aristeromycin comprising the general structure:

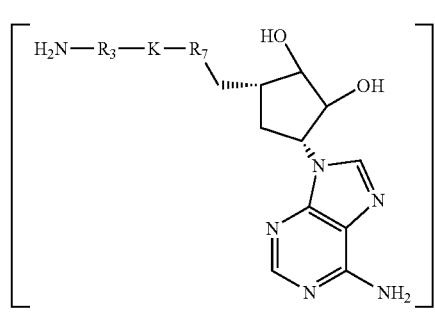

XXXIV or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked ATP derivative, Neplanocin A, comprising the general structure:

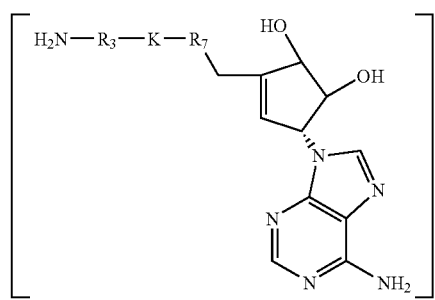

XXXV or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In another embodiment, the invention includes an alkyl-linked 2',3'-dideoxy-3'-oxoadenosine, comprising the general structure:

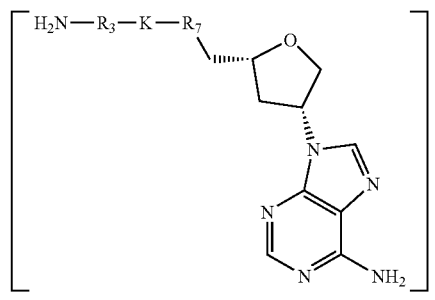

XXXVI or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In other embodiments, the invention includes an alkyl-linked 2-, 6-, or 8-substituted adenosine derivative. These substituted adenosine derivates can be made by the condensation of the corresponding bromides (for the 2 and 8 position) or chlorides (for the 6 position) and the appropriate amine (including, for example, allylamine, benzylamine, t-butylamine, 2-methoxyethylamine, and diethylamine. See, for example Halbfinger et al. (1999) *J. Med. Chem.* 42:5325-37 and van Tilburg et al. (1999) *J. Med. Chem.* 42:1393-400; each of which is herein incorporated by reference in its entirety. An example of the general structure of alkyl-linked 8-substituted adenosine is shown below:

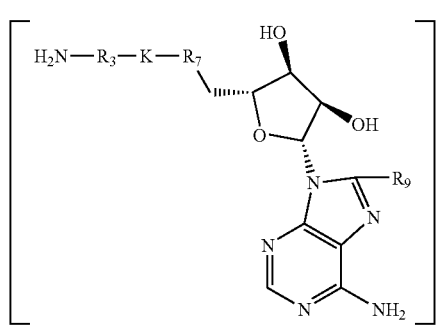

XXXVII or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof, and $R_9$ is an amine.

In an additional embodiment, the invention includes an alkyl-linked formycin A. An example of the general structure of alkyl-linked formycin A is shown below:

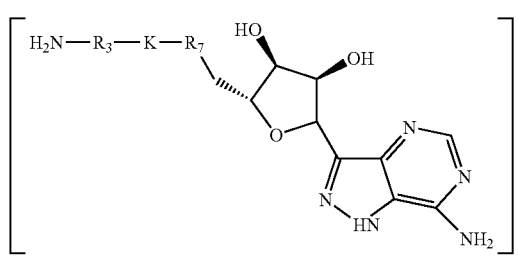

XXXVIII or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In an additional embodiment, the invention includes an alkyl-linked 4-deazaformycin. The synthesis of 4-deazaformyin A is described in Kourafalos et al. (2003) *J. Org. Chem.* 68:6466-69, herein incorporated by reference. An example of the general structure of alkyl-linked 4-deazaformycin A is shown below:

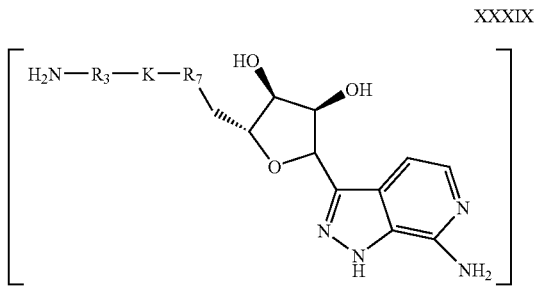

XXXIX or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In some embodiments, the invention includes an aza or deaza adenosine derivative. The synthesis of 8-aza, 8-aza-1-deaza, 8-aza-3-deaza, 1-deaza, 3-deaza, and 1,7-deaza adenine derivatives is described in Franchetti et al. (1994) *J. Med. Chem.* 37, 3534 and Seela et al. (1991) *Helv. Chim. Acta* 74:1048. These derivatives can be reacted with sugar halides or β-d-ribofuranose-1-acetate-2,3,5-tribenzoate (see, Kraybill et al. (2002) *J. Am. Chem. Soc.* 124:12118 and Saneyoshi et al. (1979) *Chem. Pharm. Bull.* 27:2518) and $SnCl_4$ to form additional adenosine derivatives. An example of the general structure of one such derivative is shown below:

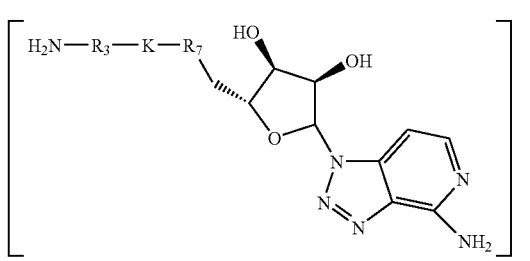

XL or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In a further embodiment, the invention includes an alkyl-linked purine riboside. An example of the general structure of alkyl-linked purine riboside is shown below:

XLI

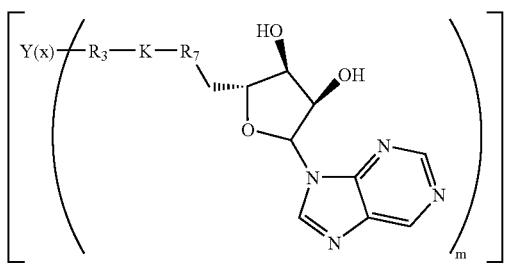

or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

The invention also provides an alkyl-linked 6-mercaptopurine riboside. An example of the general structure of alkyl-linked 6-mercaptopurine riboside is shown below:

XLII

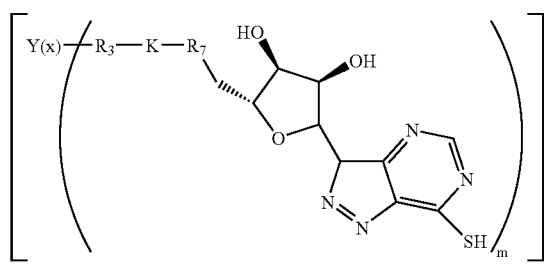

or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

The invention also provides an alkyl-linked 6-chloropurine riboside. An example of the general structure of alkyl-linked 6-chloropurine riboside is shown below:

XLIII

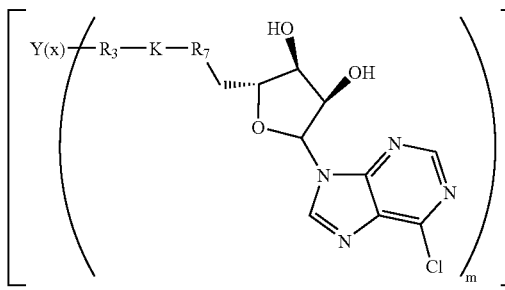

or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

The invention also provides an alkyl-linked 6-methyl purine riboside. The 6-methyl purine riboside may be synthesized by reacting 6-chloropurine riboside with the Grignard reagent methyl magnesium chloride to yield 6-methyl purine riboside (Hocek and Dvorakova (2003) *J. Org. Chem.* 68:5773-6, herein incorporated by reference). An example of the general structure of alkyl-linked 6-methyl purine riboside is shown below:

XLIV

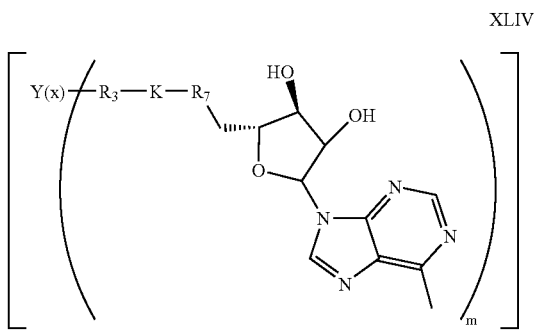

or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof.

In other embodiments, the invention includes an alkyl-linked adenosine derivative in which the ribose group has been replaced with a ribose mimic. One example of the general structure of such an alkyl-linked derivative is

XLV

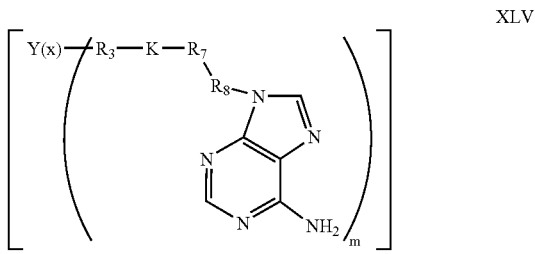

or an ionized variant or a salt thereof, wherein the linker ($R_3$) is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof and $R_8$ is a ribose mimic In some embodiments, the ribose mimic is an alkyl, $C_4$-$C_7$ cycloalkyl, heteroalkyl, aryl, or heteroaryl group. See, for example Hernandez et al. (2002) *J. Med. Chem.* 45:4254-63, herein incorporated by reference in its entirety. Examples of other suitable ribose mimics include, without limitation:

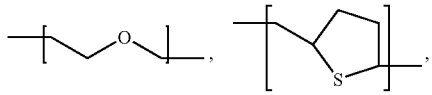
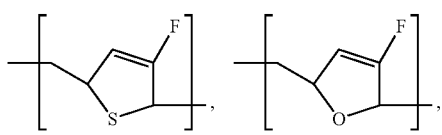
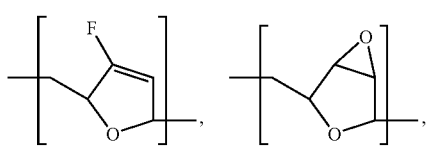
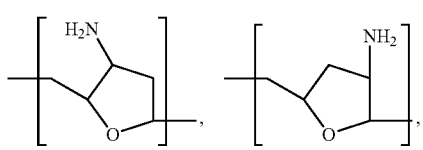
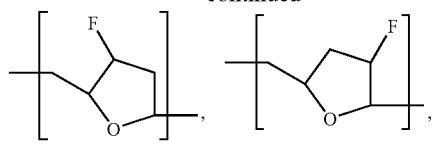
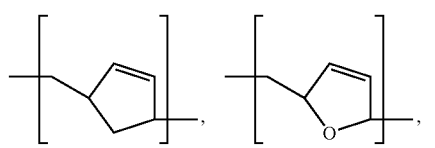
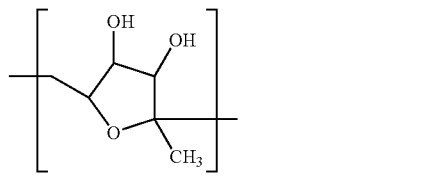
In another embodiment is an alkyl-linked nucleotide covalently bound to agarose comprising the general structure:
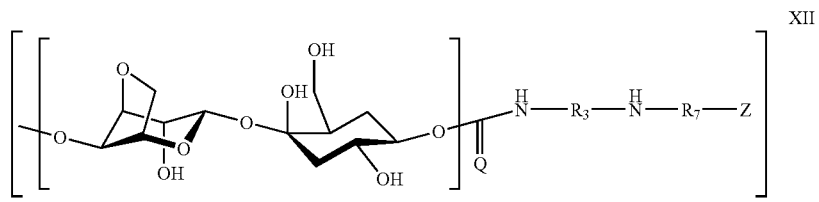
or an ionized variant or a salt thereof, wherein Q=NH$_2$+ or O.
In one embodiment, the invention includes an alkyl-linked adenosine covalently bound to agarose comprising the general structure:
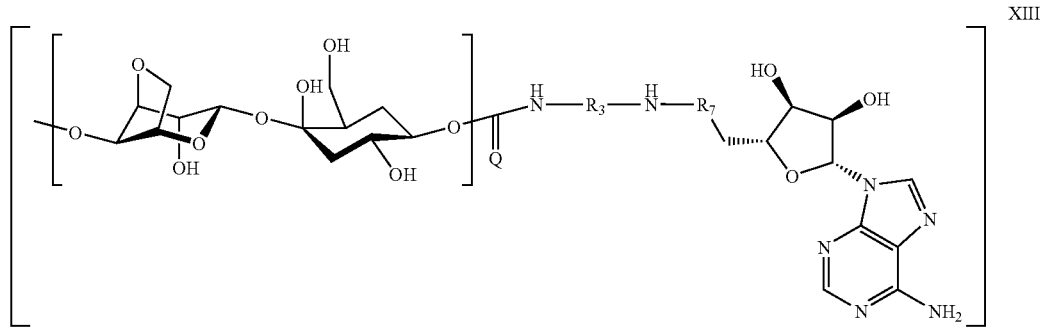

or an ionized variant or a salt thereof, wherein Q=NH$_2$+ or O.

In one embodiment, the invention includes an alkyl-linked guanosine covalently bound to agarose comprising the general structure:

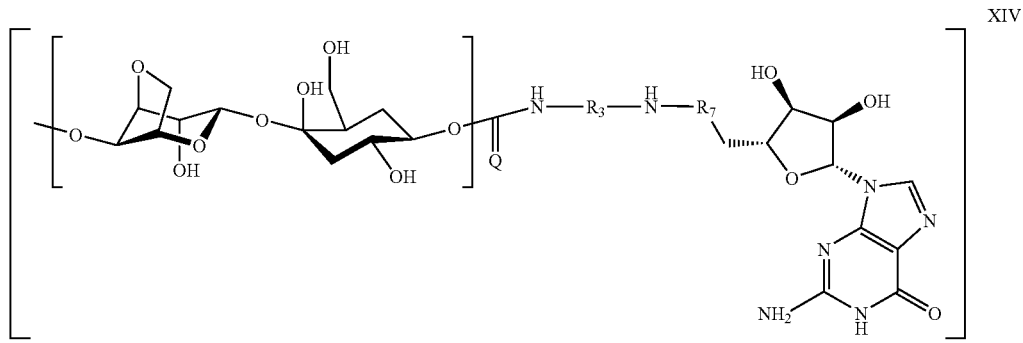

XIV or an ionized variant or a salt thereof, wherein Q=NH$_2$+ or O.

In one embodiment, the invention includes an alkyl-linked cytidine covalently bound to agarose comprising the general structure:

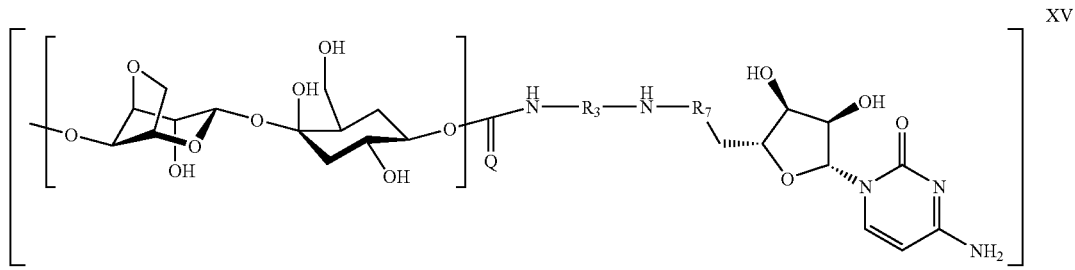

XV or an ionized variant or a salt thereof, wherein Q=NH$_2$+ or O.

In one embodiment, the invention includes an alkyl-linked thymidine covalently bound to agarose comprising the general structure:

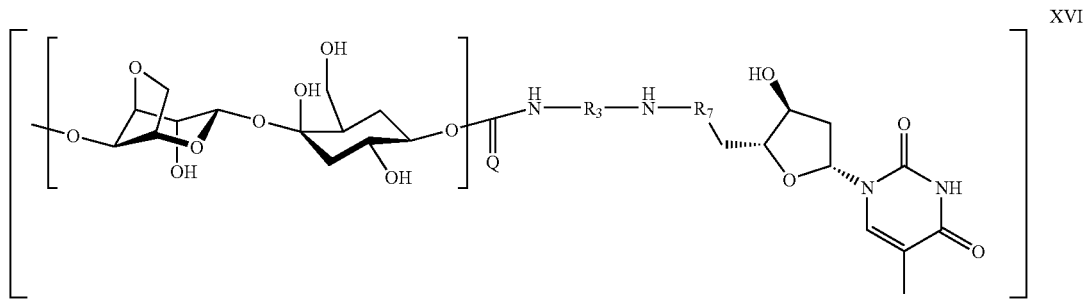

XVI or an ionized variant or a salt thereof, wherein Q=NH$_2$+ or O.

In one embodiment, the invention includes an alkyl-linked uridine covalently bound to agarose comprising the general structure:

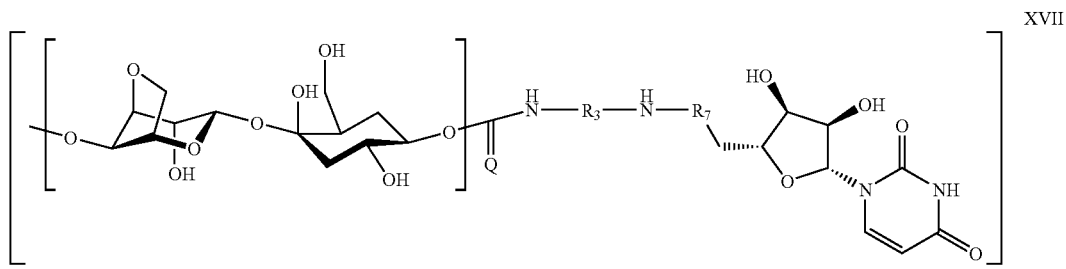

or an ionized variant or a salt thereof, wherein Q=NH$_2$+ or O.

Also included in the invention are γ-alkyl-linked nucleotide triphosphates comprising the general formula:

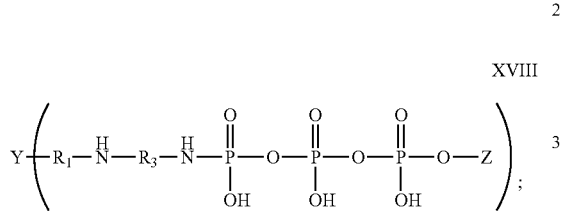

XLVI

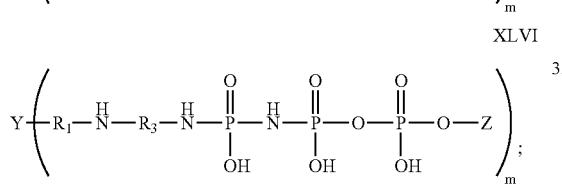

XLVII

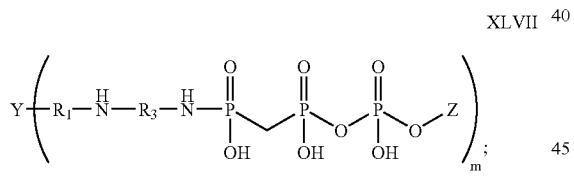

XLVIII

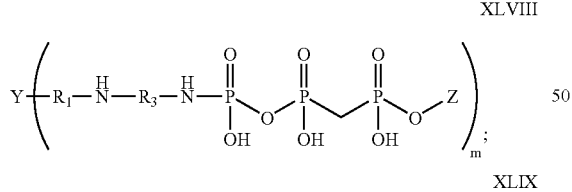

XLIX

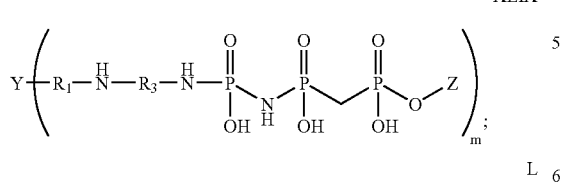

L

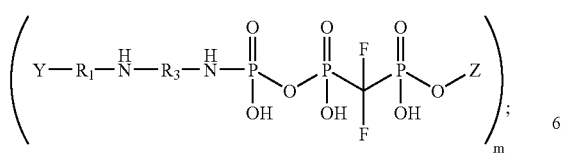

-continued

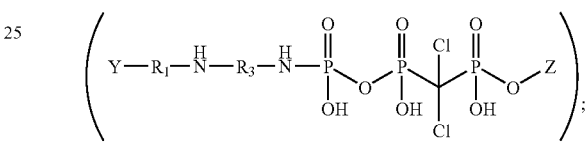

LI or an ionized variant or a salt thereof.

Also included in the invention are γ-alkyl-linked nucleotide analogs comprising the general formula:

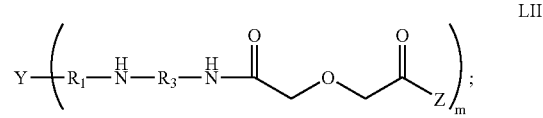

LII

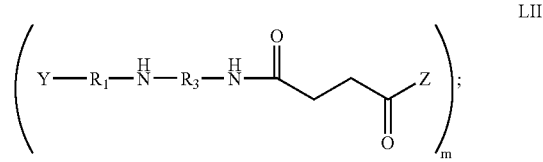

LIII

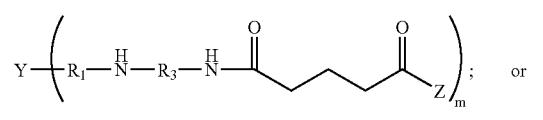

LIV or

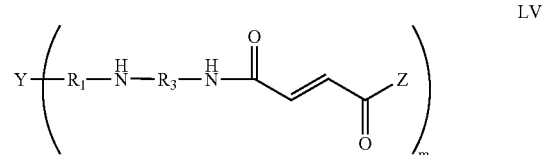

LV

In one embodiment, the invention includes a γ-phosphate-linked adenosine triphosphate bound to an agarose solid support comprising the general formula:

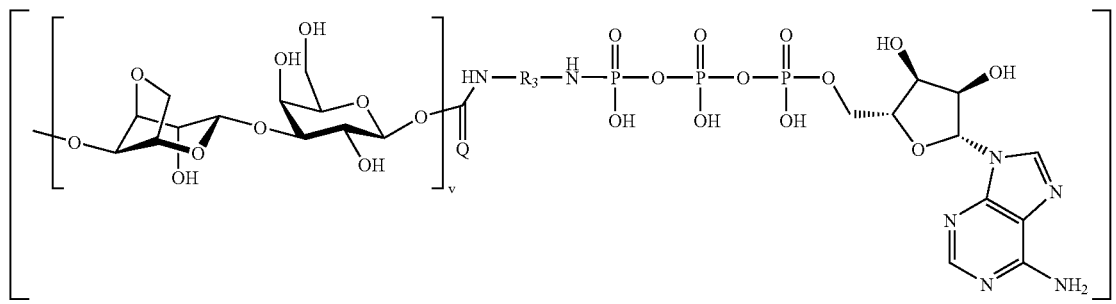

XIX or an ionized variant or a salt thereof.

In one embodiment, the invention includes a γ-phosphate-linked guanosine triphosphate bound to an agarose solid support comprising the general formula:

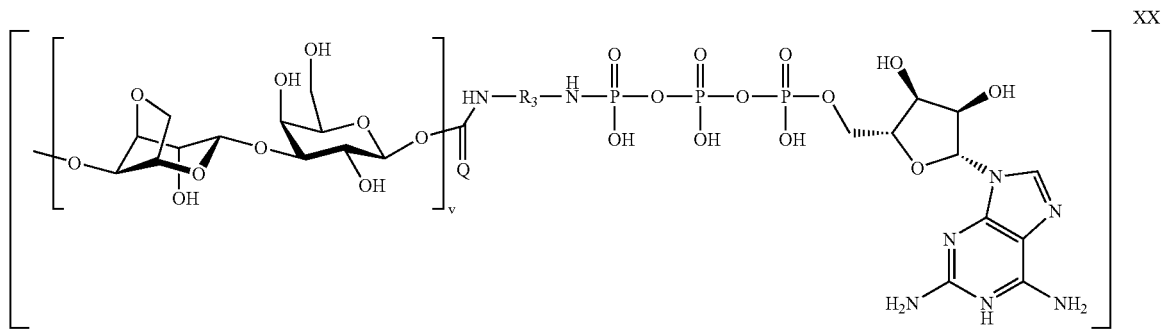

XX or an ionized variant or a salt thereof.

In another embodiment, the invention includes a γ-phosphate-linked cytidine triphosphate bound to an agarose solid support comprising the general formula:

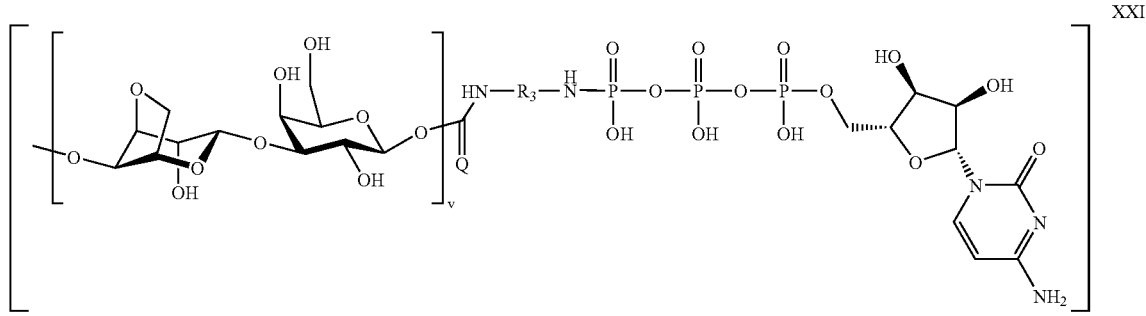

XXI or an ionized variant or a salt thereof.

In a further embodiment, the invention includes a γ-phosphate-linked thymidine triphosphate bound to an agarose solid support comprising the general formula:

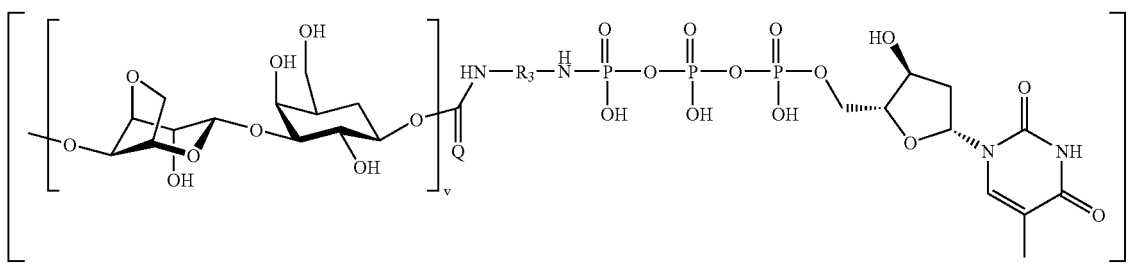

XXII or an ionized variant or a salt thereof.

In another embodiment, the invention includes γ-phosphate-linked uridine triphosphate bound to an agarose solid support comprising the general formula:

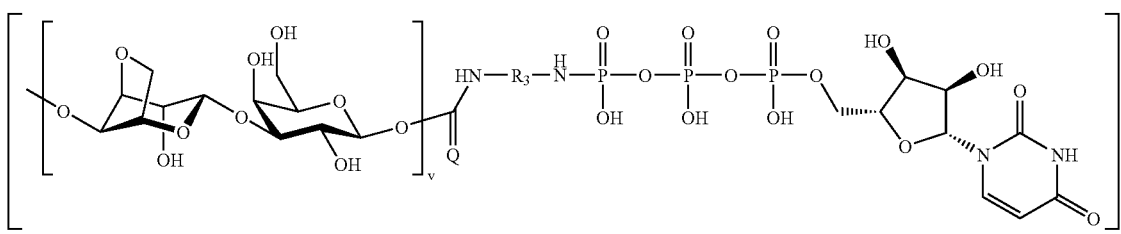

XXII or an ionized variant or a salt thereof.

Synthesis of Alkyl-Linked Nucleotide Affinity Media

Also included in the invention is a method to synthesize an alkyl-linked nucleotide affinity medium comprising a general formula:

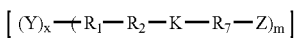

I comprising the general steps of (a) coupling at least one linker to a solid support or tag in a suitable coupling buffer, wherein the linker is $R_2$, or a combination of $R_1$ and $R_2$; (b) end-capping reactive sites remaining on the solid support or tag after the coupling step; and (c) reacting a terminal phosphate or thiophosphate group of a nucleotide with the linker coupled to the solid support or tag, wherein Y is a solid support or a tag; x=1; $R_1$ is a covalent bond between Y and $R_2$, or $R_1$ is an acyl group, a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof; $R_2$ is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof; K is a heteroatom; $R_7$ is $(P)_n$ where P is a phosphate or thiophosphate and n is at least one or $R_7$ is a phosphate group mimic, Z is a nucleoside or nucleoside derivative; and m is at least one. As described elsewhere herein, a solid support can be any suitable support, such as a resin, or a particulate material, such as a bead, or a particle. Alternatively, a solid support can be a continuous solid surface, such as a plate, chip, well, channel, column or a tube. The material of a solid support will be of any suitable substance, compound or polymer, as will be appreciated by one of skill in the art. Examples include, without limitation, acrylamide, agarose, methacrylate polymers, methacrylate co-polymers, thermoresponsive polymers, cellulose, nylon, silica, glass, ceramic, a magnetized particle or surface, nitrocellulose, polystyrene and derivatives thereof.

Furthermore, a tag, as used herein, is an agent that provides for the specific detection or capture of the alkyl-linked nucleotide. For example, and without limitation, a suitable tag is biotin, avidin, streptavidin, a hapten, a fluorophore or a chromophore. Detection or capture of the alkyl-linked nucleotide employs techniques that are standard in the art. For example, a biotin-tagged alkyl-linked nucleotide can be captured using avidin, streptavidin or related avidin derivatives. The biotin-avidin interaction is highly specific. An avidin-conjugated agent used to detect or capture a biotin-tagged alkyl-linked nucleotide can be soluble (for example, an antibody), or a particulate material (for example, beaded agarose or a magnetized particle), or a continuous surface (for example, a plate or well coated with avidin). Detection and capture of a hapten-tagged alkyl-linked nucleotide can be achieved, for example, using hapten-specific antibodies. Visual detection methods for fluorophore or chromophore-tagged alkyl-linked nucleotides are readily understood by one of skill in the art.

A nucleoside and a nucleotide, as referred to herein, can be naturally-occurring or non-naturally-occurring. Furthermore, the nucleoside or nucleotide can be biologically or synthetically-derived using techniques that are standard to one of skill in the art. Suitable nucleosides include, without limitation, adenosine (A), guanosine (G), cytidine (C), thymidine (T) and uridine (U), and derivatives thereof.

In one embodiment, the nucleotide is a monophosphate, diphosphate, triphosphate, or tetraphosphate of adenosine, guanosine, cytidine, thymidine, or uridine or an analog thereof. In certain embodiments, the phosphate moiety of the nucleotide is modified. See, for example Picher et al. (1996) *Biochem. Pharmacol.* 51:1453-60; Ingall et al. (1999) *J. Med. Chem.* 42:213-20; Gendron et al. (2000) *J. Med. Chem.* 43:2239-47; and Xu et al. (2002) *J. Med. Chem.* 45:5694-709 each of which is herein incorporated in its entirety by reference.

In other embodiments, the phosphate moiety of the nucleotide is replaced by a phosphate group mimic. For example, in some embodiments, the alkyl-linked nucleotide non-homogeneous solid supports comprise a carboxylic acid that contains 4-8 carbons in the main chain and optionally contains a heteroatom. To make these nucleotide derivates, 2',3'-isopropylidene adenosine is reacted with a cyclic anhydride, and then the acetonide is deprotected. Examples of cyclic anhydrides that may be reacted with 2',3'-isopropylidene include diglycolic anhydride, succinic anhydride, glutaric anhydride, and maleic anhydride, although any suitable electrophile may be used. The functionality of the 5'-hydroxyl of adenosine is may also be converted into a primary amine by a Mitsunobu reaction with phthalimide followed by hydrazinolysis. See, for example Bressi et al. (2001) *J. Med. Chem.* 44:2080-93 and Herforth et al. (2002) *J. Comb. Chem.* 4:302-14; each of which are herein incorporated by reference in their entirety.

Other phosphate group mimics may be used according to invention. For example, an ATP analog can be made by reacting 2',3'-O-isopropylidene-adenosine with 4-chlorosulfonylbenzoic acid to give an ATP analog having the formula:

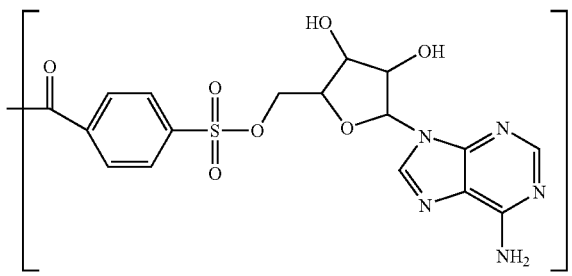

The benzene ring can be substituted with hydroxyl or amine groups. See, for example, Rosse et al. (1997) *Helv. Chim. Acta.* 80:653, herein incorporated by reference.

In another example, 2',3'-O-isopropylidene-adenosine is reacted with sulfamoyl chloride, the sulfonamide is conjugated with a carboxylic acid (for example, benzyl malonate or t-butyl malonate) and then deprotected in one or two steps to give an ATP analog having the structure:

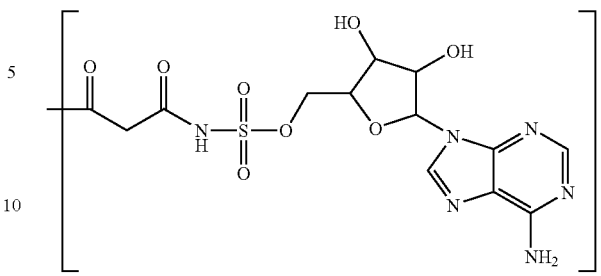

After conjugation with t-butyl malonate only one acidic deprotection step is performed; After conjugation with benzyl malonate a catalytic hydrogenation of the benzyl group and an acidic cleavage of the acetonide group are performed. In addition to mono-protected malonates, mono-protected succinates or glutarates can be used. In addition, the sulfonamide can be reacted with other electrophiles such as bromoacetic acid to obtain phosphate group mimics. Amino acids can also be used to link the sulfonamide with a linker. See, Koroniak et al. (2003) *Pharmacology & Therapeutics* 93:145, herein incorporated by reference.

In a further example, an ATP analog is made by conjugating adenosine-5'-carboxylic acid with β-alanine to form an ATP analog having the structure:

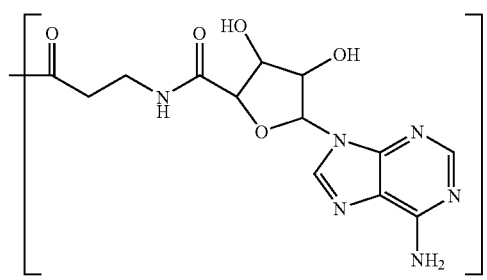

Other aminocarboxylic acids can be used. In addition, adenosine-5'-carboxylic acid can be conjugated with amino acids or peptides. See, Loog et al. (2000) *FEBS Letters* 480:244; and Parang et al. (2002) *Pharmacology and Therapeutics* 93:145, both of which are herein incorporated by reference in their entirety.

Other non-limiting examples of phosphate group mimics that may be used in the alkyl-linked nucleotide non-homogeneous solid supports of the present invention include:

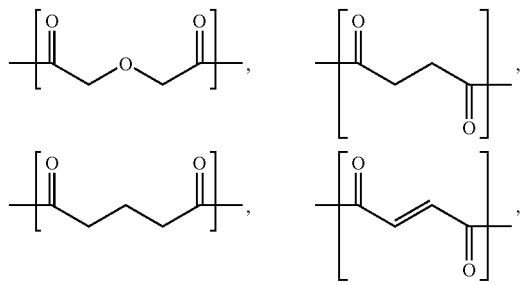

-continued

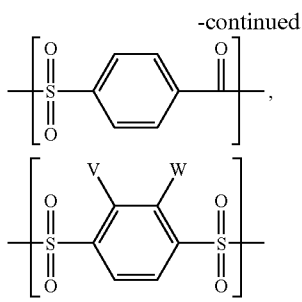

where V and W can be H or a heteroatom such as NH$_2$ or OH,

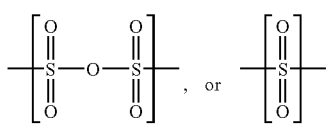

The ribose moiety of the alkyl-linked nucleotide may be modified or replaced. For example, oxidation and acetonide protection of 4-penten-1-ol yields an intermediate that can be reacted with the adenine under classic Mitsunobu conditions. Mitsunobu reactions between alcohols and the adenine N9 are well established. See, for example, Chang et al. (1999) *Chemistry & Biology* 6:361-75. Deprotection of the acetonide then leads to a first ligand ready for phosphorylation and attachment to a resin-linker arm combination. The primary alcohol of the same intermediate can also be oxidized to the aldehyde, followed by acetonide deprotection and ring closure. Selective protection of the primary hydroxyl over the secondary hydroxyl, a Mitsunobu reaction, and deprotection of the primary hydroxyl results in a second ligand.

Non-limiting examples of nucleoside analogs that may be used in the compositions of the invention include 2'-deoxy-adenosine, 3'-deoxy-adenosine, 2'-deoxy-2'-amino-adenosine, 3'-deoxy-3'-amino adenosine, formycin A, 4-deazaformycin A, aristeromycin, neplanocin A, purine riboside, 6-mercaptopurine riboside, 6-chloropurine riboside, 6-methyl purine riboside, and 2',3'-dideoxy-3'-oxoadenosine. See, for example, Guranowski et al. (1981) *Biochemistry* 20:110; Yaginuma et al. (1981) *J. Antibiot.* 23:359; Robins et al. (1983) *J. Am. Chem. Soc.* 105:4059; Borchardt et al. (1984) *J. Biol. Chem.* 259:5353; De Clerq et al. (1987) *Biochem. Pharmacol.* 36:2567; Huryn et al. (1989) *Tetrahedron Lett.* 30:6259; Franchetti et al. (1994) *J. Med. Chem.* 37:3534; Van Calenbergh et al. (1994) *Helv. Chim. Acta.* 77:631; Cowart et al. (1999) *J. Org. Chem.* 64:2240; Hocek and Dvorakova (2003) *J. Org. Chem.* 68:5773; and Kourafalos et al. (2003) *J. Org. Chem.* 68:6466-69; each of which is herein encompassed by reference in its entirety.

In still other embodiments, the nucleoside or nucleotide is a 2-, 6- or 8-substituted adenosine derivative. Such derivatives may be made by the condensation of the corresponding bromides (for the 2 and 8 position) or chlorides (for the 6 position) and the appropriate amine, e.g. allylamine, benzylamine, t-butylamine, 2-methoxyethylamine, diethylamine. See, for example Halbfinger et al (1999) *J. Med. Chem.* 42: 5325, and van Tilburg et al. (1999) *J. Med. Chem.* 42:1393.

In some embodiments, the compositions comprise a ribose mimic. For example, the ribose of the nucleoside or nucleotide is replaced with an alkyl, C$_4$-C$_7$ cycloalkyl, heteroalkyl, aryl, or heteroaryl group. This may be accomplished by monotitrylation of diols, followed by a Mitsunobu reaction with adenine and deprotection of the titrylated alcohol. See, for example, Hernandez et al. (2002) *J. Med. Chem.* 45, 4254, herein incorporated by reference. Other ribose mimics and their syntheses are described, for example, in Lee et al. (1961) *J. Am. Chem. Soc.* 83:1906; Imazawa (1978) *J. Org. Chem.* 43:3044; Robins et al. (1984) *Tetrahedron Letters* 25:367; Herdewijn et al. (1987) *J. Med. Chem.* 30:2131-37; Wu et al. (1988) *Tetrahedron* 44:6705; Van Aerschot et al. (1989) *J. Med. Chem.* 32:1743-49; Secrist et al. (1991) *J. Med. Chem.* 34:2361-66; Secrist et al. (1992) *J. Med. Chem.* 35:533-38; Holletz et al. (1994) *Synthesis* 8:789; Choi et al. (1998) *Tetrahedron Letters* 25:367; Meier et al. (1999) *Nucleosides Nucleotides* 18:907-12; Meier et al. (1999) *J. Med. Chem.* 42:1615-24; and Choo et al. (2003) *J. Med. Chem.* 46:389-98.

The synthesis of an alkyl-linked nucleotide affinity medium comprising alkyl-linked nucleotides is generally done in three steps: first the linker (or linkers) is attached to the solid support (also referred to herein generally as a resin); second, any remaining active sites on the solid support are end-capped using a suitable reagent such as, for example, ethanolamine, 2-amino-2-(hydroxymethyl)-1,3-propanediol, or glycine; and third, the linker arm is reacted with the affinity ligand of choice, for example, a nucleotide, such as, adenosine triphosphate (ATP), thus producing a nucleotide affinity medium.

The attachment of a tag, such as biotin, to a nucleotide via a linker uses techniques that are standard in the art. For example, biotin can be synthesized with a linker arm attached; such compounds are known to one of skill in the art and are commercially available with different linker arms already attached; for example:

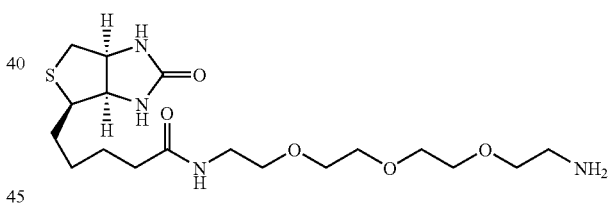

To synthesize an alkyl-linked nucleotide attached to a biotin tag, the water-soluble biotin linker complex is reacted with the nucleotide which has been reacted with 1-(3-dimethylaminopropyl)-3-ethylcarbodiimide hydrochloride (EDC) and 1-methyl imidazole.

The synthesis of an alkyl-linked nucleotide with a protective group uses techniques that are known in the art. Typically the linker, for example a diamine linker, is asymmetrically protected (i.e. protected at one end) to form a water-soluble semi-protected diamine linker. The unprotected end of the linker, is reacted with a nucleotide which has been prepared by reacting the nucleotide with EDC and 1-methyl imidazole, as will be understood by one of ordinary skill in the art.

As already described herein, an alkyl-linked nucleotide attached to a solid support or a tag, such that the solid support or tag is suitable for the separation of the alkyl-linked nucleotide, and optionally, compounds (such as proteins, for example) bound to the alkyl-linked nucleotide, from unbound compounds, is also referred to herein as a "nucleotide affinity medium or media", or as an "alkyl-linked nucleotide affinity medium or media."

Generally, the linker is attached to the solid support in any suitable coupling buffer as will be understood by one of skill in the art. For example, the coupling buffer can be 0.1M or 0.2M sodium phosphate, pH adjusted to 8-9 for cyanogen bromide-activated SEPHAROSE™, or 0.1M or 0.2M sodium phosphate, pH adjusted to 10 for 1,1'-carbonyl diimidazole-activated (CDI)-SEPHAROSE™. Alternatively, 0.01M to 0.1M borate, with pH adjusted to 8-9 can be used for coupling cyanogen bromide-activated SEPHAROSE™, or 0.01M to 0.1M borate, with pH adjusted to 10 can be used for coupling CDI-activated SEPHAROSE™. For example, a linker can be reacted at room temperature with cyanogen bromide-activated SEPHAROSE™ beaded agarose in a sodium bicarbonate coupling buffer (for example, and as used in the Examples below, 0.1 M $NaHCO_3$, 0.5 M NaCl, pH=8.2). For reactions with CDI-activated cross-linked SEPHAROSE™ beaded agarose, the linker can be, for example, reacted at room temperature with the resin in a 0.05 M $NaHCO_3$—$Na_2CO_3$ coupling buffer, pH=10, such as will be understood by one of skill in the art. Typically, the solid support is then washed with water.

The solid support is then end-capped to block remaining active sites on the solid support and is a standard technique that can be performed with any suitable reagent, such as, ethanolamine, 2-amino-2-(hydroxymethyl)-1,3-propanediol, or glycine. To illustrate, end-capping can be achieved by reacting the solid support with 1M ethanolamine (pH=8.9) for approximately 1 hour at room temperature. The solid support is then typically washed with 1M NaCl and water.

The nucleotide is then reacted with the linker arm on the solid support under suitable conditions, as will be understood by one of skill in the art, and as described in the Examples.

Once prepared, an alkyl-linked nucleotide bound to a solid support or tag (nucleotide affinity medium) is stored in any suitable buffer. For example, 0.1M $K_2HPO_4$—$KH_2PO_4$ buffer (pH=7.4), containing 0.02% sodium azide as a preservative.

Synthesis methods for isourea and carbamate linkages are standard in the art (see generally, Hermanson et al., "Immobilized Affinity Ligand Techniques", Academic Press, 1992, the teaching of which is incorporated herein by reference in its entirety). For example, the use of a cyanogen bromide-activated agarose (see, generally, Cuatrecasas and Anfinsen, "Affinity Chromatography" in Ann. Rev. Biochem. Snell et al., eds. (CA: Annual Reviews Inc.), 40: 259-278 (1971), the teachings of which are incorporated herein by reference in their entirety) provides for the synthesis of a suitable isourea linkage, whereas the use of a CDI-activated cross-linked SEPHAROSE™ beaded agarose 6B (Pierce Biotechnology, Inc.) provides a suitable carbamate linkage. Alternatively, the hydroxyl group of a suitable resin can be converted into suitable leaving groups using N,N'-disuccinimidylcarbonate as an intermediate to prepare a carbamate linkage, or using organic sulfonyl chlorides to activate the resin hydroxyl groups for nucleophilic displacement to prepare a carbon-nitrogen bond.

The alkyl-linked nucleotides bound to a solid support in the following exemplification were made with cyanogen bromide-activated SEPHAROSE™ beaded agarose 4B (Sigma), CDI-activated cross-linked SEPHAROSE™ beaded agarose 6B (Pierce Biotechnology, Inc.), TOYOPE-ARL® resins, SEPHACRYL™ resins, Trisacryl resins, or Ultrogel resins. Other suitable solid supports will be readily appreciated by one of skill in the art and include, for example and without limitation, acrylamide, agarose, methacrylate polymer, methacrylate copolymer, cellulose, nylon, silica, magnetized particle, nitrocellulose and polystyrene, and derivatives thereof.

Prior to use, cyanogen bromide-activated SEPHAROSE™ beaded agarose is washed with 1 mM HCl and water, whereas CDI-activated cross-linked SEPHAROSE™ beaded agarose is washed with ice-cold water, in accordance with standard protocols, as will be understood by one of skill in the art.

One example of the chemical synthesis of a γ-phosphate-linked nucleotide affinity ligand is illustrated in FIGS. 1-5. For the purpose of illustration, the nucleotide is ATP.

FIG. 1 illustrates the chemical formation of Intermediate IA. Cyanogen bromide-activated SEPHAROSE™ beaded agarose is reacted with a diamino-hydrophobic linker to form a resin-bound linker (Intermediate IA).

Figure 2:
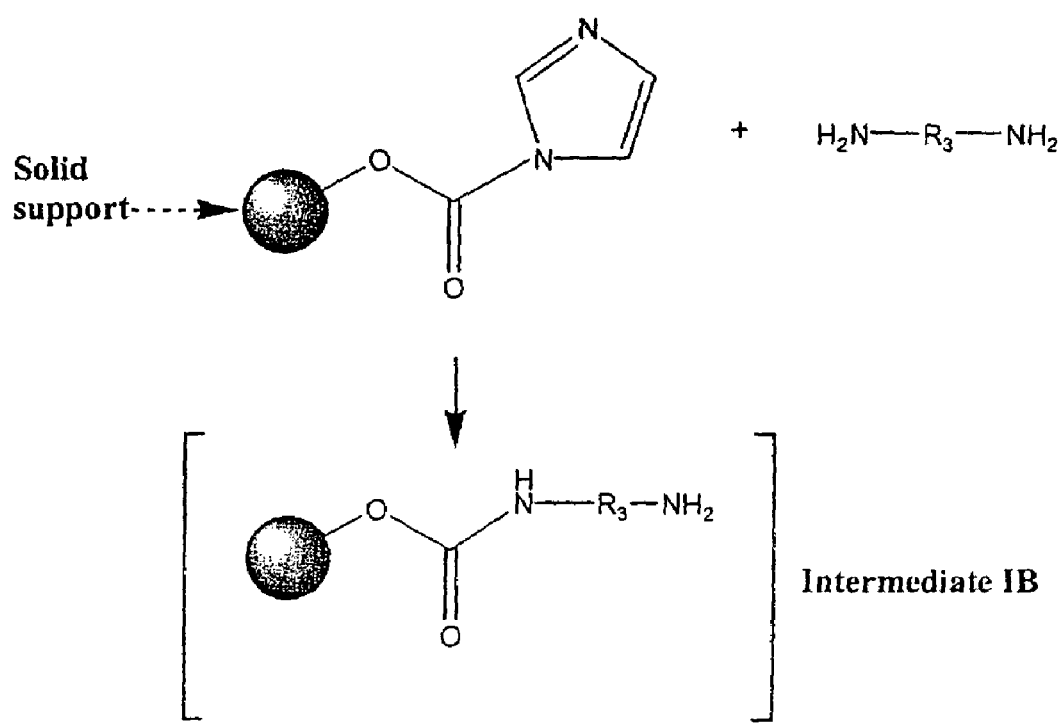
FIG. 2 is a schematic of the synthesis of a compound Intermediate IB using 1,1'-carbonyldiimidazole (CDI)-activated beaded agarose and a linker.

Using an alternative resin, FIG. 2 illustrates the chemical formation of Intermediate IB. CDI-activated SEPHAROSE™ beaded agarose is reacted with a diamino-hydrophobic linker to form a resin-bound linker (Intermediate IB).

Figure 3:
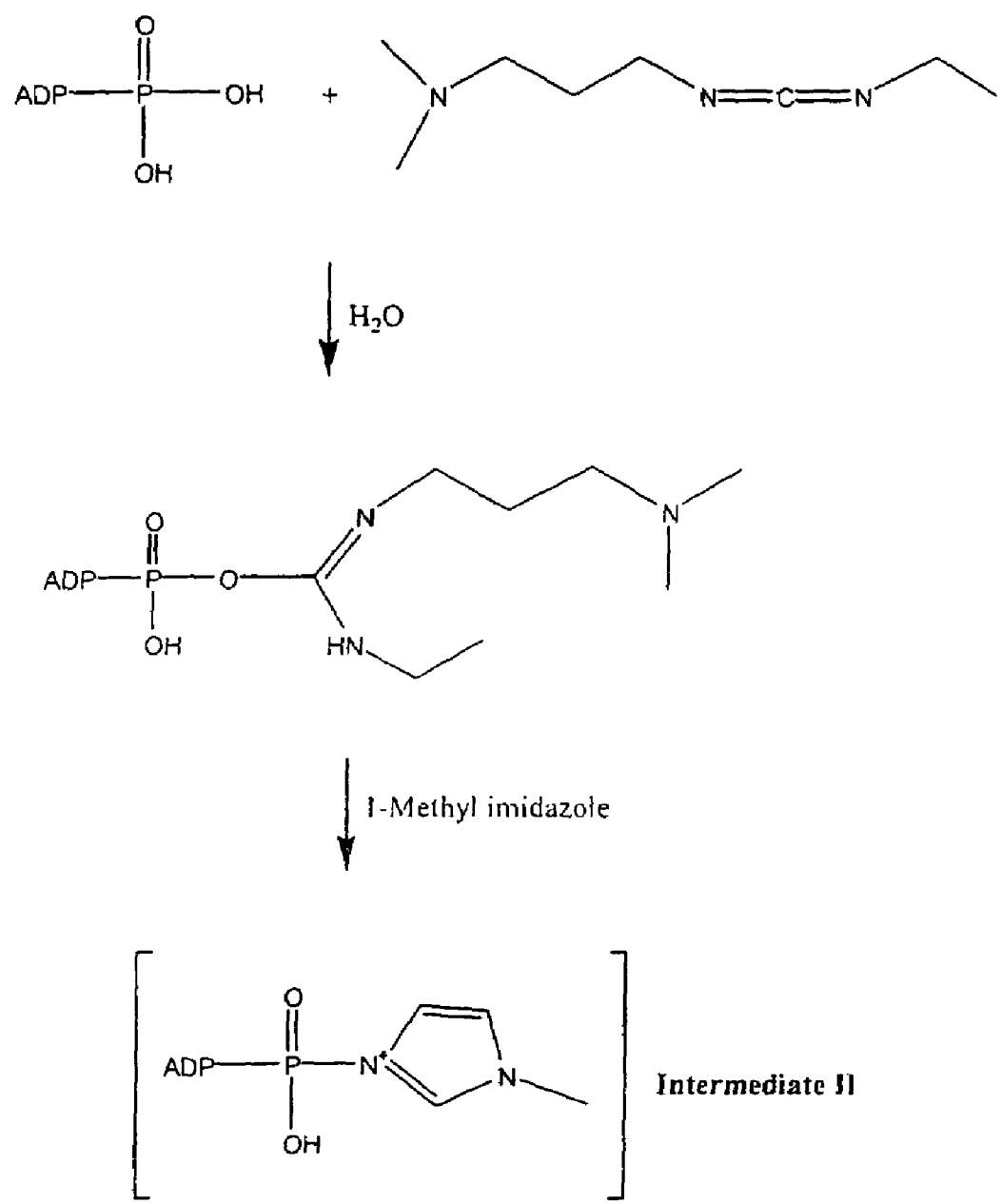
FIG. 3 is a schematic of the synthesis of a compound Intermediate II.

The chemical formation of Intermediate II, which is the modification of the nucleotide in preparation of its attachment to the resin, is illustrated in FIG. 3. The nucleotide is reacted with a water-soluble carbodiimide, such as 1-(3-dimethylaminopropyl)-3-ethyl carbodiimide hydrochloride (EDC) to form O-phosphoryl isourea. The O-phosphoryl isourea is then reacted with a suitable nucleophilic compound, for example, 1-methyl imidazole to form Intermediate II.

Figure 4:
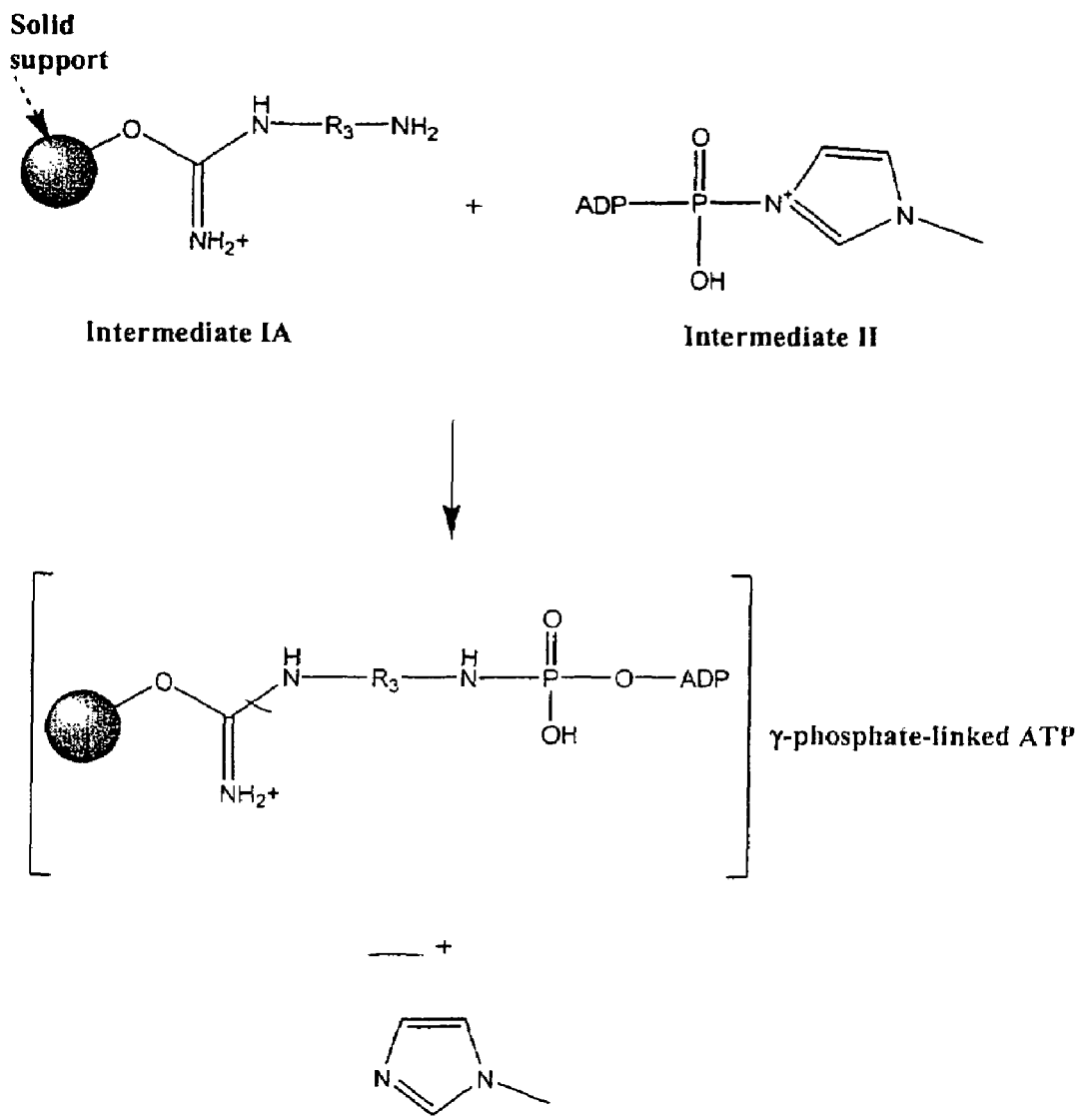
FIG. 4 is a schematic of the synthesis of a γ-phosphate-linked ATP using Intermediates IA and II as reaction components.
Figure 5:
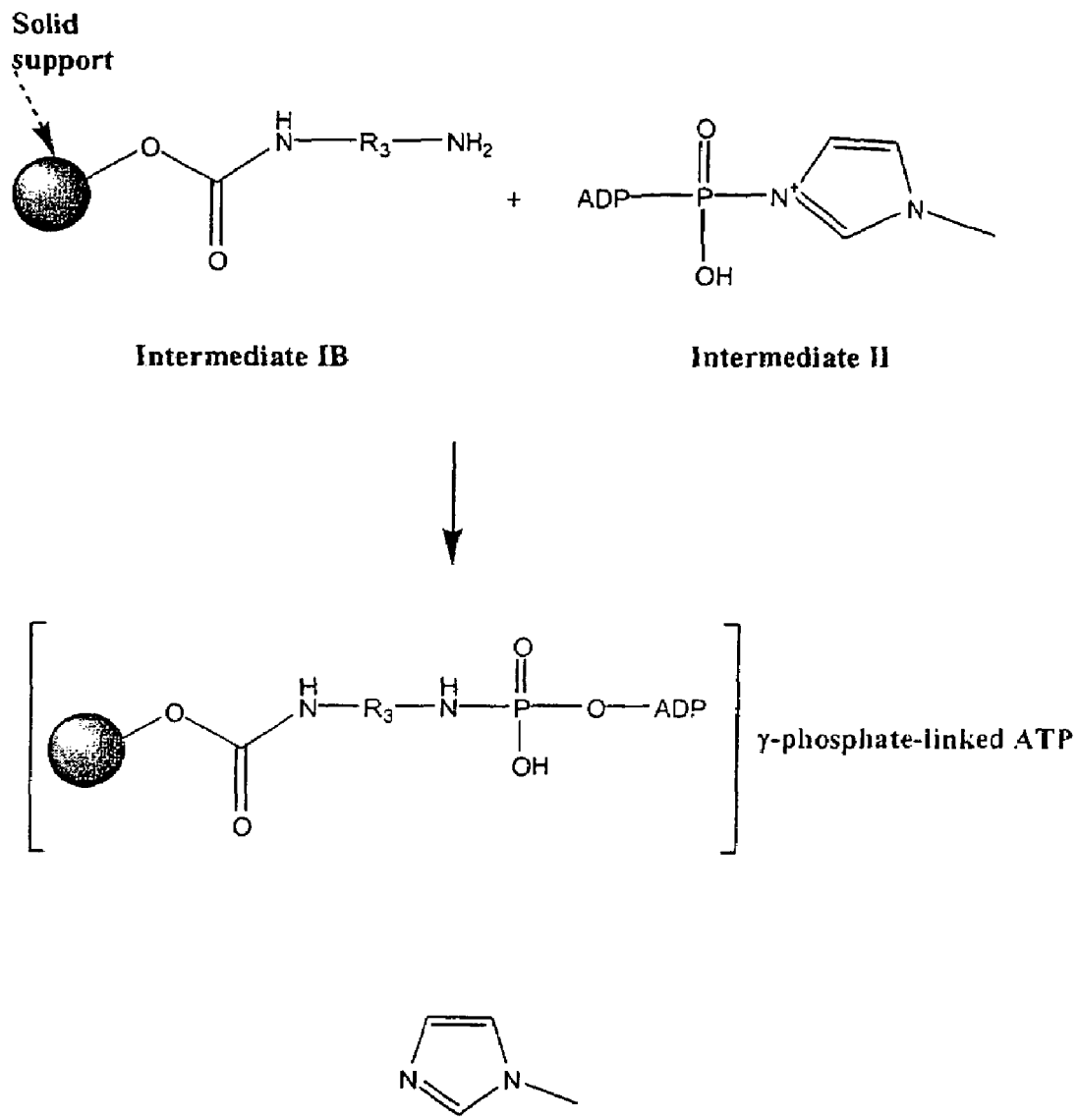
FIG. 5 is a schematic of the synthesis of a γ-phosphate-linked ATP using Intermediates IB and II as reaction components.

The final steps for the synthesis of nucleotide affinity media are illustrated in FIGS. 4 and 5. Specifically, FIG. 4 illustrates one example of the chemical formation of a nucleotide affinity medium. Intermediates IA and II are combined to form the final alkyl-linked nucleotide bound to a solid support. In another example, shown in FIG. 5, Intermediates IB and II are combined to form the final alkyl-linked nucleotide bound to a solid support.

In one embodiment, the loading of a solid support with an alkyl-linked nucleotide can be varied. This means that not necessarily all reactive sites on a solid support are reacted with an alkyl-linked nucleotide. For example, the loading of a solid support with an alkyl-linked nucleotide can be in a range of 5-25%, meaning 5-25% of reactive sites are reacted with an alkyl-linked nucleotide. Alternatively, the loading of the alkyl-linked nucleotide is in a range of 20-50%, 40-65%, 60-80% or 75-100%. The reactive groups on the solid support which are not reacted with an alkyl-linked nucleotide can be capped using a suitable reagent as appropriate.

Utility of Alkyl-Linked Nucleotide Compositions

Also included in the invention is a method for screening compounds, for example, with a proteome comprising the steps of (a) contacting a proteome with a nucleotide affinity medium comprising a general formula:

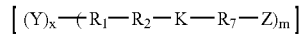

$$[(Y)_x\text{---}(R_1\text{---}R_2\text{---}K\text{---}R_7\text{---}Z)_m] \qquad I$$

wherein Y is a solid support or a tag; x=1; $R_1$ is a covalent bond between Y and $R_2$, or $R_1$ is an acyl group, a substituted or a non-substituted alkyl group, a substituted or a non-substituted cycloalkyl group, a substituted or a non-substituted heteroalkyl group, a substituted or a non-substituted heterocycloalkyl group, a substituted or a non-substituted aryl group, a substituted or a non-substituted heteroaryl group, or a combination thereof; $R_2$ is a substituted or a non-substituted alkyl group, a substituted or a non-substituted cycloalkyl group, a substituted or a non-substituted heteroalkyl group, a substituted or a non-substituted heterocycloalkyl, a substituted or a non-substituted heteroaryl group, or a combination thereof; K is a heteroatom; $R_7$ is $(P)_n$ where P is a phosphate or thiophosphate and n is at least one or $R_7$ is a phosphate group mimic, Z is a nucleoside or nucleoside derivative; and m is at least one; (b) washing the nucleotide affinity medium with a buffer, whereby non-specifically bound components of the proteome are eluted from the nucleotide affinity medium and specific components of the proteome remain bound to the nucleotide affinity medium; (c) contacting the nucleotide affinity medium bound to specific components of the proteome with at least one test compound; (d) eluting from the nucleotide affinity medium components of the proteome that are specifically displaced by the test compound; and (e) identifying the components of the proteome that are specifically displaced by the test compound from the nucleotide affinity medium.

A test compound can be any compound that is organic or inorganic, naturally-occurring or non-naturally occurring, as will be appreciated by one of skill in the art. For example, the test compound can be a compound from a combinatorial library or a chemical library. Furthermore, the test compound can be a compound extracted from a single cellular organism, a multicellular organism, or from an organ or a tissue of a multicellular organism. Examples of such organisms include, without limitation, bacteria, algae, fungi, plant, fish, amphibians, mammals, and the like. The test compound can be a single compound, or alternatively, a mixture of compounds, as will be understood by one of skill in the art.

As described elsewhere herein, a solid support can be any suitable support, such as a resin, or a particulate material, such as a bead, or a particle. Alternatively, a solid support can be a continuous solid surface, such as a plate, chip, well, channel, column or a tube. The material of a solid support will be of any suitable substance, compound or polymer, as will be appreciated by one of skill in the art. Examples include, without limitation, acrylamide, agarose, methacrylate polymer, methacrylate copolymer, cellulose, nylon, silica, glass, ceramic, a magnetized particle or surface, nitrocellulose, polystyrene and derivatives thereof.

Furthermore, a "tag", as that term is employed herein, is an agent that provides for the specific detection or capture of the alkyl-linked nucleotide. For example, and without limitation, a suitable tag is biotin, avidin, streptavidin, a hapten, a fluorophore or a chromophore. Detection or capture of the alkyl-linked nucleotide employs techniques that are standard in the art. For example, a biotin-tagged alkyl-linked nucleotide can be captured using avidin, streptavidin or related avidin derivatives. The biotin-avidin interaction is highly specific. An avidin-conjugated agent used to detect or capture a biotin-tagged alkyl-linked nucleotide can be soluble (for example, an antibody), or a particulate material (for example, beaded agarose or a magnetized particle), or a continuous surface (for example, a plate or well coated with avidin). Detection and capture of a hapten-tagged alkyl-linked nucleotide can be achieved, for example, using hapten-specific antibodies. Visual detection methods for fluorophore or chromophore-tagged alkyl-linked nucleotides are readily understood by one of skill in the art. The visual detection of fluorophore or chromophore-tagged alkyl-linked nucleotides will be useful for techniques such as rapidly determining the presence or absence of a specific interaction between the tagged alkyl-linked nucleotide and a target protein. Alternatively, the visual detection of fluorophore or chromophore-tagged alkyl-linked nucleotides will be useful for detecting the presence or absence of a specific interaction between a test compound and a tagged alkyl-linked nucleotide bound to a target protein. Furthermore, linker-specific effects on the affinity or avidity of the affinity ligand for a compound can be monitored using fluorophore or chromophore-tagged alkyl-linked nucleotides. For example, a linker can affect the selectivity, affinity or avidity of the alkyl-linked nucleotide for an interacting compound via steric hindrance or electrostatic interactions, for example. These linker-specific effects can be assayed or monitored by visually detecting which linkers attached to a nucleotide specifically affect the interaction of the nucleotide with the target protein or compound. Such linkers can be used to prepare nucleotide affinity media that selectively bind a subset of proteins or target compounds.

As described elsewhere herein, a nucleoside and a nucleotide, as referred to herein, can be naturally-occurring or non-naturally-occurring. Furthermore, the nucleoside or nucleotide can be biologically or synthetically-derived using techniques that are standard to one of skill in the art. Suitable nucleosides include, without limitation, adenosine (A), guanosine (G), cytidine (C), thymidine (T) and uridine (U).

In one embodiment, the nucleotide is a monophosphate, diphosphate, or triphosphate of adenosine, guanosine, cytidine, thymidine, or uridine or an analog thereof.

The alkyl-linked nucleotide affinity media of the invention can be used, for example, in affinity chromatography techniques using methods that are known to one of skill in the art. See, for example, WO 00/63694, filed 12 Apr. 2000 and U.S. Pat. No. 5,536,822, filed Mar. 4, 1994, the teachings of which are incorporated herein by reference in their entirety.

The nucleotide affinity media and alkyl-linked nucleotides are useful for the detection and purification of biological compounds that bind to a nucleotide. For example, γ-phosphate-linked adenosine triphosphate (ATP) can be used to detect and purify biological compounds such as kinases, which are known to bind ATP. Specifically, an alkyl-linked nucleotide, such as ATP, can be bound to a solid support or tag, and subsequently contacted with, or mixed with, a proteome or part thereof. Non-specifically-interacting components of a proteome are generally removed by washing with a suitable buffer, as will be readily understood by one of skill in the art.

Additionally, the alkyl-linked nucleotide can be used to screen chemical compounds that specifically interact with a protein captured by the alkyl-linked nucleotide. Subsequently, this protein can be identified using art-standard techniques.

Alternatively, the alkyl-linked nucleotide can be used to detect and isolate chemical compounds that specifically bind to the nucleotide. For example, an alkyl-linked nucleotide can be mixed with a combinatorial library. Compounds of the combinatorial library that specifically interact with the alkyl-linked nucleotide can be separated from non-specifically-interacting compounds, for example, by washing with one or more suitable buffers. Subsequently, the specifically-interacting compounds can be identified using art-standard techniques.

Alternatively, competitors of compounds which are known to interact with a nucleotide can be identified. For example, an alkyl-linked nucleotide can be mixed with a known interacting compound, such as a protein, to allow for their binding to occur. Then another compound or library of compounds (such as a combinatorial library) can be added to the alkyl-linked nucleotide bound to the known compound. If one or more different compounds can compete for binding to the nucleotide (and thus, displace the first bound compound), the known compound will be released and the competitor compound can be subsequently identified. Such compounds may be useful biological or pharmacological inhibitors.

EXEMPLIFICATION

The present invention is further illustrated by the following examples, which are not intended to be limiting in any way. For the purpose of simplicity of illustration, the solid support is generically represented as:

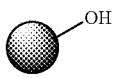

wherein, generally a hydroxyl group on the solid support is available to react with a suitable reagent, for example cyanogen bromide which will form a cyanogen bromide-activated solid support. The solid support may be any suitable solid support as described above.

Example 1

The following general structure represents the affinity ligand bound to a solid support when synthesized using the linker and reaction conditions described in Example 1:

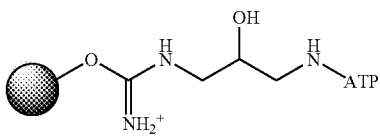

The linker arm was attached to the resin by adding 1 g of 1,3-diamino-2-propanol to 30 mL coupling buffer and combining with 2 g cyanogen bromide-activated SEPHAROSE™. The reaction was allowed to proceed for approximately 3 hours at room temperature.

The affinity ligand, ATP, was prepared for attachment to the resin by adding 500 mg ATP, 103.5 mg N-hydroxysuccinimide and 172.5 mg EDC to 20 mL water, and reacting for approximately 2 hours at room temperature.

Finally, the nucleotide affinity media was prepared by adding 111 mg 4-dimethylaminopyridine to the activated affinity ligand and combining with the prepared resin and allowing the reaction to continue for approximately 12-18 hours, or overnight, at room temperature.

Example 2

The following general structure represents the affinity ligand bound to a solid support when synthesized using the linker and reaction conditions described in Example 2:

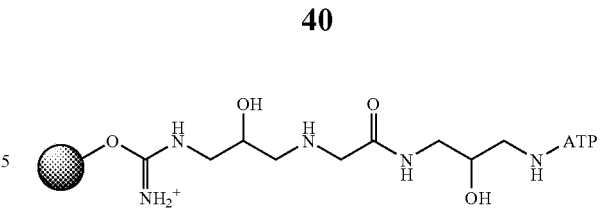

The linker was attached to the resin by first adding 1 g 1,3-diamino-2-propanol to 30 mL coupling buffer and combining with 2 g cyanogen bromide-activated SEPHAROSE™. The reaction proceeded for approximately 3 hours. A second reaction of the resin was performed by adding 1.5 g iodoacetic acid to 30 mL coupling buffer, and adjusting the pH to 9.8 and combining with the resin. This was reacted for a further 1 hour, approximately, at room temperature. In a further reaction with the resin, 500 mg EDC was added to 20 mL water and combined with the resin. Reaction proceeded for a further 30 minutes. Subsequently, 1 g 1,3-diamino-2-propanol was added to 30 mL coupling buffer and combined with the resin. Reaction continued for another 1 hour, approximately.

The affinity ligand was prepared by adding 500 mg ATP, 103.5 mg N-hydroxysuccinimide and 172.5 mg EDC to 20 mL water, and allowing the reaction to proceed for approximately 2 hours.

Finally, 111 mg 4-dimethylaminopyridine was added to the prepared affinity ligand and combined with resin. Reaction was allowed to proceed for approximately 12-18 hours, or overnight at room temperature.

Examples 3-8

The following general structure represents the affinity ligand bound to a solid support when synthesized using the linker and reaction conditions described in Examples 3-8:

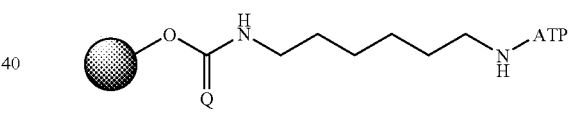

wherein Q=$NH_2^+$ or O

Example 3

To prepare the resin, 250 mg 1,6-diaminohexane was added to 5 mL coupling buffer, combined with 500 mg cyanogen bromide-activated SEPHAROSE™ and reacted for approximately 2 hours at room temperature.

The affinity ligand was prepared by adding 300 mg ATP, 104 mg EDC and 62 mg N-hydroxysuccinimide to 7 mL water, reacting for 90 minutes at room temperature.

The resin and affinity ligand were then combined together and allowed to react for approximately 12-18 hours, or overnight at room temperature.

Example 4

To prepare the resin, 250 mg 1,6-diaminohexane was added to 5 mL coupling buffer and combined with 500 mg cyanogen bromide-activated SEPHAROSE™. The reaction proceeded for approximately 2 hours at room temperature.

The affinity ligand was prepared by adding 690 mg ATP, 513 μL 1-methyl imidazole and 1200 mg EDC to 6 mL water, and reacting for approximately 1 hour at room temperature.

The resin and affinity ligand were then combined together and allowed to react for approximately 12-18 hours, or overnight at room temperature.

Example 5

To prepare the resin, 750 mg 1,6-diaminohexane was added to 7.5 mL coupling buffer and combined with 1.425 g cyanogen bromide-activated SEPHAROSE™. The reaction proceeded for approximately 2 hours at room temperature.

The affinity ligand was prepared by adding 1378 mg ATP, 1027 μL 1-methyl imidazole and 2400 mg EDC to 6 mL water, and reacting for approximately 1 hour at room temperature.

The resin and affinity ligand were then combined together and allowed to react for approximately 12-18 hours, or overnight at room temperature.

Example 6

To prepare the resin, 225 mg 1,6-diaminohexane was added to 1.5 mL coupling buffer and combine with 285 mg cyanogen bromide-activated SEPHAROSE™. The reaction proceeded for approximately 2 hours at room temperature.

The affinity ligand was prepared by adding 550 mg ATP, 410 μL 1-methyl imidazole and 960 mg EDC to 5 mL water, and reacting for approximately 1 hour at room temperature.

The resin and affinity ligand were then combined together and allowed to react for approximately 12-18 hours, or overnight at room temperature.

Example 7

To prepare the resin, 150 mg 1,6-diaminohexane was added to 3 mL coupling buffer, the pH was adjusted to pH 8.4, and then combined with 571 mg cyanogen bromide activated SEPHAROSE™. The reaction proceeded for approximately 2 hours at room temperature.

The affinity ligand was prepared by adding 1100 mg ATP, 820 μL 1-methyl imidazole and 1920 mg EDC to 10 mL water, and reacting for approximately 1 hour at room temperature.

The resin and affinity ligand were then combined together and allowed to react for approximately 12-18 hours, or overnight at room temperature.

Example 8

To prepare the resin, 250 mg 1,6-diaminohexane was added to 5 mL coupling buffer and combines with 2.5 mL CDI-activated cross-linked SEPHAROSE™. The reaction proceeded for approximately 2 hours at room temperature.

The affinity ligand was prepared by adding 690 mg ATP, 513 μL 1-methyl imidazole and 1200 mg EDC to 6 mL water, and reacting for approximately 1 hour at room temperature.

The resin and affinity ligand were then combined together and allowed to react for approximately 12-18 hours, or overnight at room temperature.

Examples 9-28

The following general structure represents the affinity ligand bound to a solid support when synthesized using the linker and reaction conditions described in Examples 9-28:

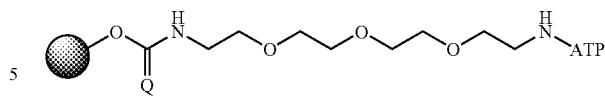

wherein $Q=NH_2^+$ or O

For all Examples 9-16, the resin was prepared by adding 700 μL 1,11-diamino-3,6,9-trioxaundecane to 10 mL coupling buffer and combining with 2 g cyanogen bromide-activated SEPHAROSE™. The reaction was allowed to proceed for approximately 2 hours at room temperature. Aliquots of 300 mg of the reacted resin were used for Examples 9-16.

Example 9

The affinity ligand was prepared by adding 275 mg ATP, 58 mg N-hydroxysuccinimide and 96 mg EDC to 3 mL water, and reacting for approximately 2 hours at room temperature.

The affinity ligand and 300 mg of prepared resin (above) were combined and allowed to react for approximately 12-18 hours, or overnight at room temperature.

Example 10

The affinity ligand was prepared by adding 275 mg ATP, 41 μL 1-methyl imidazole and 96 mg EDC to 3 mL water, and reacting for approximately 2 hours at room temperature.

The affinity ligand and 300 mg of prepared resin (above) were combined and allowed to react for approximately 12-18 hours, or overnight at room temperature.

Example 11

The affinity ligand was prepared by adding 275 mg ATP, 290 mg N-hydroxysuccinimide and 480 mg EDC to 3 mL water, and reacting for approximately 2 hours at room temperature.

The affinity ligand and 300 mg of prepared resin (above) were combined and allowed to react for approximately 12-18 hours, or overnight at room temperature.

Example 12

The affinity ligand was prepared by adding 275 mg ATP, 205 μL 1-methyl imidazole and 480 mg EDC to 3 mL water, and reacting for approximately 2 hours at room temperature.

The affinity ligand and 300 mg of prepared resin (above) were combined and allowed to react for approximately 12-18 hours, or overnight at room temperature.

Example 13

The affinity ligand was prepared by adding 275 mg ATP, 58 mg N-hydroxysuccinimide and 96 mg EDC to 3 mL water, and reacting for approximately 2 hours at room temperature.

The affinity ligand was then combined with 300 mg resin and allowed to react for approximately 5 hours at room temperature.

Alternatively, the affinity ligand was prepared by adding 275 mg ATP, 58 mg N-hydroxysuccinimide and 96 mg EDC to 3 mL water, and reacting for approximately 2 hours at room temperature.

43

The affinity ligand was then combined with 300 mg resin and allowed to react for approximately 12-18 hours, or overnight at room temperature.

Example 14

The affinity ligand was prepared by adding 275 mg ATP, 41 µL 1-methyl imidazole and 96 mg EDC to 3 mL water, and reacting for approximately 2 hours at room temperature.

The affinity ligand was then combined with 300 mg resin and allowed to react for approximately 5 hours at room temperature.

Alternatively, the affinity ligand was prepared by adding 275 mg ATP, 41 µL 1-methyl imidazole and 96 mg EDC to 3 mL water, and reacting for approximately 2 hours at room temperature.

The affinity ligand was then combined with 300 mg resin and allowed to react for approximately 12-18 hours, or overnight at room temperature.

Example 15

The affinity ligand was prepared by adding 275 mg ATP, 290 mg N-hydroxysuccinimide and 480 mg EDC to 3 mL water, and reacting for approximately 2 hours at room temperature.

The affinity ligand was then combined with 300 mg resin and allowed to react for approximately 5 hours at room temperature.

Alternatively, the affinity ligand was prepared by adding 275 mg ATP, 290 mg N-hydroxysuccinimide and 480 mg EDC to 3 mL water, and reacting for approximately 2 hours at room temperature.

The affinity ligand was then combined with 300 mg resin and allowed to react for approximately 12-18 hours, or overnight at room temperature.

Example 16

The affinity ligand was prepared by adding 275 mg ATP, 205 µL 1-methyl imidazole and 480 mg EDC to 3 mL water, and reacting for approximately 2 hours at room temperature.

The affinity ligand was then combined with 300 mg resin and allowed to react for approximately 5 hours at room temperature.

Alternatively, the affinity ligand was prepared by adding 275 mg ATP, 205 µL 1-methyl imidazole and 480 mg EDC to 3 mL water, and reacting for approximately 2 hours at room temperature.

The affinity ligand was then combined with 300 mg resin and allowed to react for approximately 12-18 hours, or overnight at room temperature.

Example 17

The resin was prepared by adding 500 µL 1,11-diamino-3,6,9-trioxaundecane to 10 mL coupling buffer and combining with 2 mL CDI-activated cross-linked SEPHAROSE™. The reaction was allowed to proceed for approximately 2 hours at room temperature.

The affinity ligand was prepared by adding 275 mg ATP, 205 µL 1-methyl imidazole and 480 mg EDC to 8 mL water, and reacting for approximately 1 hour at room temperature.

The affinity ligand was combined with the prepared resin and allowed to react for approximately 12-18 hours, or overnight at room temperature.

44

Alternatively, the affinity ligand was prepared by adding 275 mg ATP, 205 µL 1-methyl imidazole and 480 mg EDC to 4 mL water, and reacting for approximately 1 hour at room temperature.

The affinity ligand was combined with the prepared resin and allowed to react for approximately 12-18 hours, or overnight at room temperature.

Example 18

The resin was prepared by adding 200 µL 1,11-diamino-3,6,9-trioxaundecane to 2 mL coupling buffer and combining with 1 mL CDI-activated cross-linked SEPHAROSE™. The reaction was allowed to proceed for approximately 2 hours at room temperature.

The affinity ligand was prepared by adding 275 mg ATP, 205 µL 1-methyl imidazole and 480 mg EDC to 4 mL water, and reacting for approximately 1 hour at room temperature.

The resin and affinity ligand were then combined together and allowed to react for approximately 12-18 hours, or overnight at room temperature.

Example 19

The resin was prepared by adding 100 µL 1,11-diamino-3,6,9-trioxaundecane to 2 mL coupling buffer and combining with 1 mL CDI-activated cross-linked SEPHAROSE™. The reaction was allowed to proceed for approximately 2 hours at room temperature.

The affinity ligand was prepared by adding 275 mg ATP, 205 µL 1-methyl imidazole and 480 mg EDC to 4 mL water, and reacting for approximately 1 hour at room temperature.

The resin and affinity ligand were then combined together and allowed to react for approximately 12-18 hours, or overnight at room temperature.

Example 20

The resin was prepared by adding 250 µL 1,11-diamino-3,6,9-trioxaundecane to 5 mL coupling buffer and combining with 2.5 mL CDI-activated cross-linked SEPHAROSE™. The reaction was allowed to proceed for approximately 2 hours at room temperature.

The affinity ligand was prepared by adding 275 mg ATP, 82 µL 1-methyl imidazole and 192 mg EDC to 5 mL water, and reacting for approximately 1 hour at room temperature.

The resin and affinity ligand were then combined together and allowed to react for approximately 12-18 hours, or overnight at room temperature.

Alternatively, the affinity ligand was prepared by adding 250 mg ATP, 195 µL 1-methyl imidazole and 430 mg EDC to 5 mL water, and reacting for approximately 1 hour at room temperature.

The resin and affinity ligand were then combined together and allowed to react for approximately 12-18 hours, or overnight at room temperature.

Example 21

The resin was prepared by adding 75 µL ethanolamine and 75 µL 1,11-diamino-3,6,9-trioxaundecane to 3 mL coupling buffer and combining with 1.5 mL CDI-activated cross-linked SEPHAROSE™. The reaction was allowed to proceed for approximately 2 hours at room temperature.

The affinity ligand was prepared by adding 415 mg ATP, 125 µL 1-methyl imidazole and 290 mg EDC to 4 mL water, and reacting for approximately 1 hour at room temperature.

The resin and affinity ligand were then combined together and allowed to react for approximately 12-18 hours, or overnight at room temperature.

Example 22

The resin was prepared by adding 135 μL ethanolamine and 15 μL 1,11-diamino-3,6,9-trioxaundecane to 3 mL coupling buffer and combining with 1.5 mL CDI-activated cross-linked SEPHAROSE™. The reaction was allowed to proceed for approximately 2 hours at room temperature.

The affinity ligand was prepared by adding 415 mg ATP, 125 μL 1-methyl imidazole and 290 mg EDC to 4 mL water, and reacting for approximately 1 hour at room temperature.

The resin and affinity ligand were then combined together and allowed to react for approximately 12-18 hours, or overnight at room temperature.

Example 23

The resin was prepared by adding 142.5 μL ethanolamine and 7.5 μL 1,11-diamino-3,6,9-trioxaundecane to 3 mL coupling buffer and combining with 1.5 mL CDI-activated cross-linked SEPHAROSE™. The reaction was allowed to proceed for approximately 2 hours at room temperature.

The affinity ligand was prepared by adding 415 mg ATP, 125 μL 1-methyl imidazole and 290 mg EDC to 4 mL water, and reacting for approximately 1 hour at room temperature.

The resin and affinity ligand were then combined together and allowed to react for approximately 12-18 hours, or overnight at room temperature.

Example 24

The resin was prepared by adding 100 μL 1,11-diamino-3,6,9-trioxaundecane to 2 mL coupling buffer and combining with 1 mL CDI-activated cross-linked SEPHAROSE™. The reaction was reacted for approximately 2 hours at room temperature.

The affinity ligand was prepared by adding 275 mg ATP, 82 μL 1-methyl imidazole and 192 mg EDC to 3 mL water, and reacting for approximately 1 hour at room temperature.

The resin and affinity ligand were then combined together and allowed to react for approximately 12-18 hours, or overnight at room temperature.

Example 25

The resin was prepared by adding 100 μL 1,11-diamino-3,6,9-trioxaundecane to 2 mL coupling buffer and combining with 1 mL CDI-activated cross-linked SEPHAROSE™. The reaction was allowed to proceed for approximately 2 hours at room temperature.

The affinity ligand was prepared by adding 138 mg ATP, 103 μL 1-methyl imidazole and 240 mg EDC to 3 mL water, and reacting for approximately 1 hour at room temperature.

The resin and affinity ligand were then combined together and allowed to react for approximately 12-18 hours, or overnight at room temperature.

Example 26

The resin was prepared by adding 100 μL 1,11-diamino-3,6,9-trioxaundecane to 2 mL coupling buffer and combining with 1 mL CDI-activated cross-linked SEPHAROSE™. The reaction was allowed to proceed for approximately 2 hours at room temperature.

The affinity ligand was prepared by adding 138 mg ATP, 41 μL 1-methyl imidazole and 96 mg EDC to 3 mL water, and reacting for approximately 1 hour at room temperature.

The resin and affinity ligand were then combined together and allowed to react for approximately 12-18 hours, or overnight at room temperature.

Example 27

The resin was prepared by adding 100 μL 1,11-diamino-3,6,9-trioxaundecane to 2 mL coupling buffer and combining with 1 mL CDI-activated cross-linked SEPHAROSE™. The reaction was allowed to proceed for approximately 2 hours at room temperature.

The affinity ligand was prepared by adding 275 mg ATP, 204 μL 1-methyl imidazole and 96 mg EDC to 3 mL water, and reacting for approximately 1 hour at room temperature.

The resin and affinity ligand were then combined together and allowed to react for approximately 12-18 hours, or overnight at room temperature.

Example 28

The resin was prepared by adding 100 μL 1,11-diamino-3,6,9-trioxaundecane to 2 mL coupling buffer and combining with 1 mL CDI-activated cross-linked SEPHAROSE™. The reaction was allowed to proceed for approximately 2 hours at room temperature.

The affinity ligand was prepared by adding 275 mg ATP, 41 μL 1-methyl imidazole and 480 mg EDC to 3 mL water, and reacting for approximately 1 hour at room temperature.

The resin and affinity ligand were then combined together and allowed to react for approximately 12-18 hours, or overnight at room temperature.

Examples 29-36

The following general structure represents the affinity ligand bound to a solid support when synthesized using the linker and reaction conditions described in Examples 29-36:

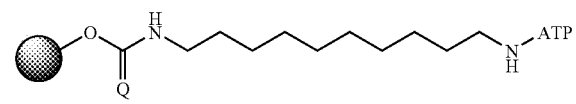

wherein Q=$NH_2^+$ or O

Example 29

The resin was prepared by adding 250 mg 1,10-diaminodecane and 1 mL 1,4-dioxane to 4 mL coupling buffer and combining with 571 mg cyanogen bromide-activated SEPHAROSE™. The reaction was allowed to proceed for approximately 2 hours at room temperature.

The affinity ligand was prepared by adding 550 mg ATP, 410 μL 1-methyl imidazole and 960 mg EDC to 6 mL water, and reacting for approximately 1 hour at room temperature.

The resin and affinity ligand were then combined together and allowed to react for approximately 12-18 hours, or overnight at room temperature.

Example 30

The resin was prepared by adding 125 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 482 mg ATP, 359 μL 1-methyl imidazole and 840 mg EDC to 5.25 mL water, and reacting for approximately 1 hour at room temperature.

The resin and affinity ligand were then combined together and allowed to react for approximately 12-18 hours, or overnight at room temperature.

Example 31

The resin was prepared by adding 250 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 482 mg ATP, 359 μL 1-methyl imidazole and 840 mg EDC to 5.25 mL water, and reacting for approximately 1 hour at room temperature.

The resin and affinity ligand were then combined together and allowed to react for approximately 12-18 hours, or overnight at room temperature.

Example 32

The resin was prepared by adding 219 mg 1,10-diaminodecane and 0.875 mL 1,4-dioxane to 3.5 mL coupling buffer and combining with 500 mg cyanogen bromide-activated SEPHAROSE™. The reaction was allowed to proceed for approximately 2 hours at room temperature.

The affinity ligand was prepared by adding 482 mg ATP, 359 μL 1-methyl imidazole and 840 mg EDC to 2.5 mL water, and reacting for approximately 1 hour at room temperature.

The resin and affinity ligand were then combined together and allowed to react for approximately 12-18 hours, or overnight at room temperature.

Example 33

The resin was prepared by adding 219 mg 1,10-diaminodecane and 0.875 mL 1,4-dioxane to 3.5 mL coupling buffer and combining with 500 mg cyanogen bromide-activated SEPHAROSE™. The reaction was allowed to proceed for approximately 2 hours at room temperature.

The affinity ligand was prepared by adding 241 mg ATP, 180 μL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 34

The resin was prepared by adding 125 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 241 mg ATP, 180 μL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 35

The resin was prepared by adding 250 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 241 mg ATP, 180 μL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 36

The resin was prepared by adding 125 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 482 mg ATP, 359 μL 1-methyl imidazole and 840 mg EDC to 2.5 mL water, and reacting for approximately 1 hour at room temperature.

The resin and affinity ligand were then combined together and allowed to react for approximately 12-18 hours, or overnight at room temperature.

Example 37

The following general structure represents the affinity ligand bound to a solid support when synthesized using the linker and reaction conditions described in Example 37:

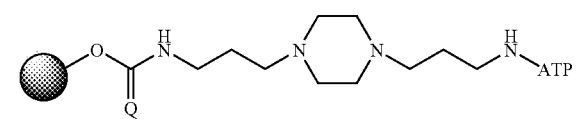

wherein Q=$NH_2^+$ or O

The resin was prepared by adding 125 μL 1,4-bis(3-aminopropyl)piperazine and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 241 mg ATP, 180 μL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 38

The following general structure represents the affinity ligand bound to a solid support when synthesized using the linker and reaction conditions described in Example 38:

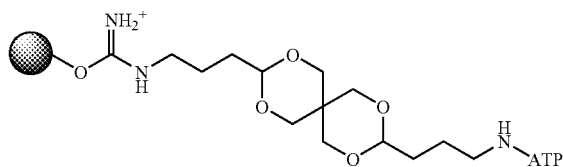

The resin was prepared by adding 125 mg 2,4,8,10-tetraoxaspiro[5.5]undecane-3,9-dipropanamine and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 241 mg ATP, 180 μL 1-methyl imidazole and 40 mg EDC to 2.5 mL water, and reacting for approximately 1 hour at room temperature.

The resin and affinity ligand were then combined together and allowed to react for approximately 12-18 hours, or overnight at room temperature.

Example 39

The following general structure represents the affinity ligand bound to a solid support when synthesized using the linker and reaction conditions described in Example 39:

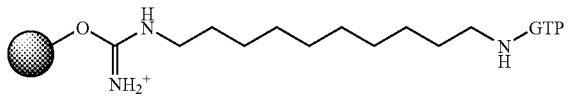

The resin was prepared by adding 62.5 mg 1,10-diaminodecane and 0.25 mL 1,4-dioxane to 1 mL coupling buffer and combining with 140 mg cyanogen bromide-activated SEPHAROSE™. The reaction was allowed to proceed for approximately 2 hours at room temperature.

The affinity ligand was prepared by adding 39 mg GTP, 31 μL 1-methyl imidazole and 72 mg EDC to 1 mL water, and reacting for approximately 1 hour at room temperature.

The resin and affinity ligand were then combined together and allowed to react for approximately 12-18 hours, or overnight at room temperature.

Example 40

The following general structure represents the affinity ligand bound to a solid support when synthesized using the linker and reaction conditions described in Example 40:

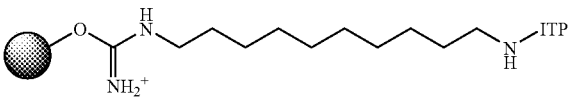

The resin was prepared by adding 62.5 mg 1,10-diaminodecane and 0.25 mL 1,4-dioxane to 1 mL coupling buffer and combining with 140 mg cyanogen bromide-activated SEPHAROSE™. The reaction was allowed to proceed for approximately 2 hours at room temperature.

The affinity ligand was prepared by adding 43 mg ITP, 31 μL 1-methyl imidazole and 72 mg EDC to 1 mL water, and reacting for approximately 1 hour at room temperature.

The resin and affinity ligand were then combined together and allowed to react for approximately 12-18 hours, or overnight at room temperature.

Example 41

The following general structure represents the affinity ligand bound to a solid support when synthesized using the linker and reaction conditions described in Example 41:

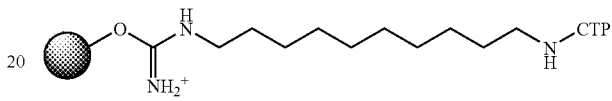

The resin was prepared by adding 62.5 mg 1,10-diaminodecane and 0.25 mL 1,4-dioxane to 1 mL coupling buffer and combining with 140 mg cyanogen bromide-activated SEPHAROSE™. The reaction was allowed to proceed for approximately 2 hours at room temperature.

The affinity ligand was prepared by adding 40 mg CTP, 31 μm 1-methyl imidazole and 72 mg EDC to 1 mL water, and reacting for approximately 1 hour at room temperature.

The resin and affinity ligand were then combined together and allowed to react for approximately 12-18 hours, or overnight at room temperature.

Example 42

The following general structure represents the affinity ligand bound to a solid support when synthesized using the linker and reaction conditions described in Example 42:

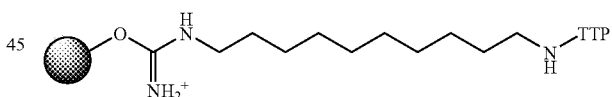

The resin was prepared by adding 62.5 mg 1,10-diaminodecane and 0.25 mL 1,4-dioxane to 1 mL coupling buffer and combining with 140 mg cyanogen bromide-activated SEPHAROSE™. The reaction was allowed to proceed for approximately 2 hours at room temperature.

The affinity ligand was prepared by adding 36 mg TTP, 31 μL 1-methyl imidazole and 72 mg EDC to 1 mL water, and reacting for approximately 1 hour at room temperature.

The resin and affinity ligand were then combined together and allowed to react for approximately 12-18 hours, or overnight at room temperature.

Example 43

The following general structure represents the affinity ligand bound to a solid support when synthesized using the linker and reaction conditions described in Example 43:

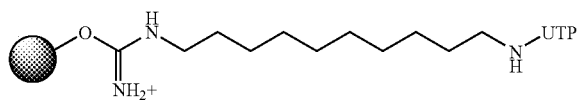

The resin was prepared by adding 62.5 mg 1,10-diaminodecane and 0.25 mL 1,4-dioxane to 1 mL coupling buffer and combining with 140 mg cyanogen bromide-activated SEPHAROSE™. The reaction was allowed to proceed for approximately 2 hours at room temperature.

The affinity ligand was prepared by adding 37 mg UTP, 31 µL 1-methyl imidazole and 72 mg EDC to 1 mL water, and reacting for approximately 1 hour at room temperature.

The resin and affinity ligand were then combined together and allowed to react for approximately 12-18 hours, or overnight at room temperature. React overnight.

Examples 44-48

The following general structure represents the affinity ligand bound to a solid support when synthesized using the linker and reaction conditions described in Examples 44-48:

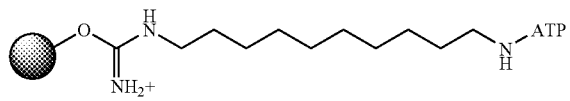

Example 44

The resin was prepared by adding 187.5 mg 1,10-diaminodecane, 62.5 µL ethanolamine and 1 mL 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Example 45

The resin was prepared by adding 125 mg 1,10-diaminodecane, 125 µL ethanolamine and 1 mL 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Example 46

The resin was prepared by adding 62.5 mg 1,10-diaminodecane, 187.5 µL ethanolamine and 1 mL 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Example 47

The resin was prepared by adding 25 mg 1,10-diaminodecane, 225 µL ethanolamine and 1 mL, 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Example 48

The resin was prepared by adding 83 mg 1,10-diaminodecane, 167 µL ethanolamine and 1 mL 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Examples 49-50

The following general structure represents the affinity ligand bound to a solid support when synthesized using the linkers and reaction conditions described in Examples 49-50:

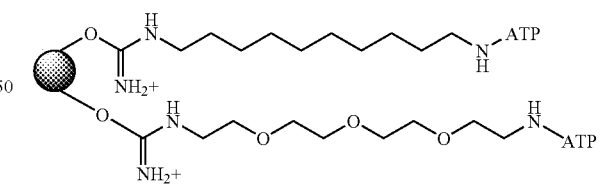

Example 49

The resin was prepared by adding 125 mg 1,10-diaminodecane, 125 µL 1,11-diamino-3,6,9-trioxaundecane and 1 mL 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Example 50

The resin was prepared by adding 62.5 mg 1,10-diaminodecane, 187.5 µL 1,11-diamino-3,6,9-trioxaundecane and 1 mL 1,4-dioxane to 4 mL coupling buffer and combining with 1 g cyanogen bromide-activated SEPHAROSE™. The reaction was allowed to proceed for approximately 2 hours at room temperature.

The affinity ligand was prepared by adding 480 mg ATP, 360 µL 1-methyl imidazole and 840 mg EDC to 5 mL water, and reacting for approximately 1 hour at room temperature.

The resin and affinity ligand were then combined together and allowed to react for approximately 12-18 hours, or overnight at room temperature.

Example 51

The following general structure represents the affinity ligand bound to a solid support when synthesized using the linker and reaction conditions described in Example 51:

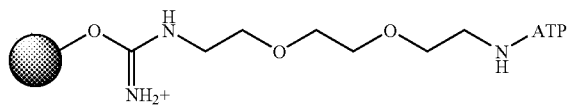

The resin was prepared by adding 125 µL 1,8-diamino-3,6-dioxaoctane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 µL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Examples 52-53

The following general structure represents the affinity ligand bound to a solid support when synthesized using the linkers and reaction conditions described in Examples 52-53:

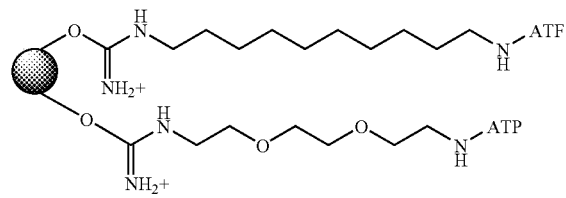

Example 52

The resin was prepared by adding 62.5 mg 1,10-diaminodecane, 62.5 µL 1,8-diamino-3,6-dioxaoctane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 µL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 53

The resin was prepared by adding 31.5 mg 1,10-diaminodecane, 93.75 µL 1,8-diamino-3,6-dioxaoctane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 µL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Examples 54-56

The following general structure represents the affinity ligand bound to a solid support when synthesized using the linkers and reaction conditions described in Examples 54-56:

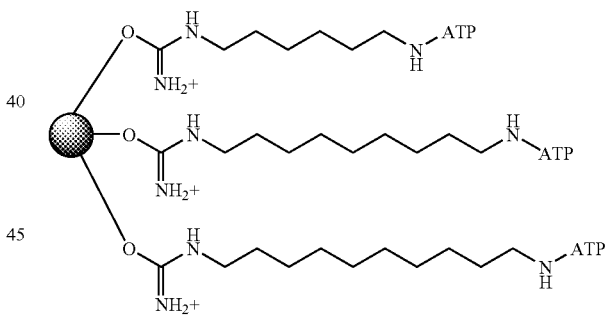

For Examples 54-56, a mixture of 100 mg of each linker arm: 1,10-diaminodecane; 1,9-diaminononane; and 1,6-diaminohexane, was prepared for use in the preparation of the nucleotide affinity media described.

Example 54

The resin was prepared by adding 125 mg of the mixture of linker arms (above), and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 µL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 55

The resin was prepared by adding 62.5 mg of the mixture of linker arms (above), 62.5 µL ethanolamine and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 µL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 56

The resin was prepared by adding 31.25 mg of the mixture of linker arms (above), 93.75 µL ethanolamine and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 µL 1-methyl imidazole and 420 mg EDC to 2.5 mL water, and reacting for approximately 1 hour at room temperature.

The resin and affinity ligand were then combined together and allowed to react for approximately 12-18 hours, or overnight at room temperature.

Example 57

The following general structure represents the affinity ligand bound to a solid support when synthesized using the linker and reaction conditions described in Example 57:

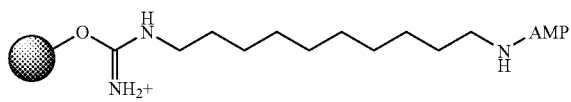

The resin was prepared by adding 125 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 160 mg AMP, 180 µL 1-methyl imidazole and 420 mg EDC to 2.5 mL water, and reacting for approximately 1 hour at room temperature.

The resin and the affinity ligand were combined and allowed to react for approximately 12-18 hours, or overnight, at room temperature.

Example 58

The following general structure represents the affinity ligand bound to a solid support when synthesized using the linker and reaction conditions described in Example 58:

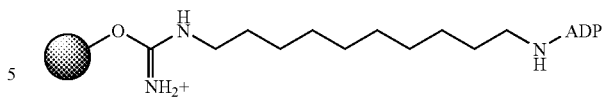

The resin was prepared by adding 125 mg 1,10-diaminodecane and 0.5 mL 1,4-dioxane to 2 mL coupling buffer and combining with 500 mg cyanogen bromide-activated SEPHAROSE™. The reaction was allowed to proceed for approximately 2 hours at room temperature.

The affinity ligand was prepared by adding 188 mg ADP, 180 µL 1-methyl imidazole and 420 mg EDC to 2.5 mL water, and reacting for approximately 1 hour at room temperature.

The resin and the affinity ligand were combined and allowed to react for approximately 12-18 hours, or overnight, at room temperature.

General procedure for SEPHACRYL™ and TOYOPEARL® resins:

SEPHACRYL™ and TOYOPEARL® resins are generally stored in 20% ethanol. After washing 2.5 mL of the resin with 2 volumes of water, 1 volume of 30% acetone, 1 volume of 70% acetone and 5 volumes of dry acetone the resin is transferred into 2.5 mL dry acetone. 200 mg 1,1'-carbonyl diimidazole is added and the resin is allowed to react for approximately 1 hour at room temperature. After approximately 1 hour the resin is washed with 5 volumes of dry acetone, 1 volume of 70% acetone, 1 volume of 30% acetone and 2 volumes of water. 250 mg 1,10-diaminodecane and 1 mL 1,4-dioxane are added to 4 mL of a suitable coupling buffer and combined with the resin. The resin is allowed to react overnight at 4° C. The resin is then washed with three volumes of 1 M NaCl and two volumes of water. To end-cap any remaining reactive sites, 5 mL of a 1 M ethanolamine solution (pH=8.9) is added to the resin and the resin is allowed to react at room temperature for approximately 1 hour. The resin is subsequently washed with three volumes of 1 M NaCl and two volumes of water. 964 mg ATP, 720 µL 1-methyl imidazole and 1680 mg EDC are added to 10 mL water, and after reacting for approximately 1 hour, are combined with the resin. The resin is allowed to react overnight. Finally the resin is washed with three volumes of 1 M NaCl and two volumes of water and transferred into a storage buffer.

Examples 59-64

The following general structure represents the affinity ligand bound to a solid support when synthesized using the linker and reaction conditions described in Examples 59-64:

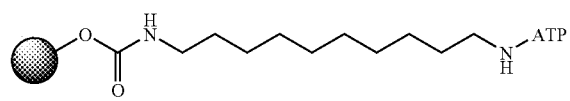

Example 59

The resin is prepared by combining 2.5 mL of HR S-300 SEPHACRYL™ resin with 2.5 mL dry acetone and 200 mg 1,1'-carbonyl diimidazole. The reaction is allowed to proceed for approximately 1 hour. Next, 250 mg 1,10-diaminodecane and 1 mL 1,4-dioxane are added to 4 mL of coupling buffer and combined with the resin. The reaction is allowed to proceed for approximately 12-18 hours, or overnight, at 4° C. Any remaining reactive sites are end-capped by adding 5 mL of a 1 M ethanolamine solution to the resin and reacting for approximately 1 hour.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 60

The resin is prepared by combining 2.5 mL of HR S-300 SEPHACRYL™ resin with 2.5 mL dry acetone and 200 mg 1,1'-carbonyl diimidazole. The reaction is allowed to proceed for approximately 1 hour. Next, 125 mg 1,10-diaminodecane, 125 µL ethanolamine and 1 mL 1,4-dioxane are added to 4 mL of coupling buffer and combined with the resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 61

The resin is prepared by combining 2.5 mL of HR S-300 SEPHACRYL™ resin with 2.5 mL dry acetone and 200 mg 1,1'-carbonyl diimidazole. The reaction is allowed to proceed for approximately 1 hour. Next, 62.5 mg 1,10-diaminodecane, 187.5 µL ethanolamine and 1 mL 1,4-dioxane are added to 4 mL of coupling buffer and combined with the resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 62

The resin is prepared by combining 2.5 mL of HR S-400 SEPHACRYL™ resin with 2.5 mL dry acetone and 200 mg 1,1'-carbonyl diimidazole. The reaction is allowed to proceed for approximately 1 hour. Next, 250 mg 1,10-diaminodecane and 1 mL 1,4-dioxane are added to 4 mL of coupling buffer and combined with the resin. The reaction is allowed to proceed for approximately 12-18 hours, or overnight, at 4° C. Any remaining reactive sites are end-capped by adding 5 mL of a 1 M ethanolamine solution to the resin and reacting for approximately 1 hour.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 63

The resin is prepared by combining 2.5 mL of HR S-400 SEPHACRYL™ resin with 2.5 mL dry acetone and 200 mg 1,1'-carbonyl diimidazole. The reaction is allowed to proceed for approximately 1 hour. Next, 125 mg 1,10-diaminodecane, 125 µL ethanolamine and 1 mL 1,4-dioxane are added to 4 mL of coupling buffer and combine with resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 64

The resin is prepared by combining 2.5 mL of HR S-400 SEPHACRYL™ resin with 2.5 mL dry acetone and 200 mg 1,1'-carbonyl diimidazole. The reaction is allowed to proceed for approximately 1 hour. Next, 62.5 mg 1,10-diaminodecane, 187.5 µL ethanolamine and 1 mL 1,4-dioxane are added to 4 mL of coupling buffer and combine with resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Examples 65-70

The following general structure represents the affinity ligand bound to a solid support when synthesized using the linker and reaction conditions described in Examples 65-70:

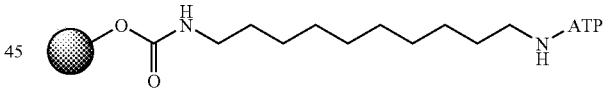

Example 65

The resin is prepared by combining 2.5 mL of HW-65F TOYOPEARL® resin with 2.5 mL dry acetone and 200 mg 1,1'-carbonyl diimidazole. The reaction is allowed to proceed for approximately 1 hour. Next 250 mg 1,10-diaminodecane and 1 mL 1,4-dioxane are added to 4 mL of coupling buffer and combined with the resin. The reaction is allowed to proceed for approximately 12-18 hours, or overnight, at 4° C. Any remaining reactive sites are end-capped by adding 5 mL of a 1 M ethanolamine solution to the resin and reacting for approximately 1 hour.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 66

The resin is prepared by combining 2.5 mL of HW-65F TOYOPEARL® resin with 2.5 mL dry acetone and 200 mg 1,1'-carbonyl diimidazole. The reaction is allowed to proceed for approximately 1 hour. Next, 125 mg 1,10-diaminodecane, 125 µL ethanolamine and 1 mL 1,4-dioxane are added to 4 mL of coupling buffer and combined with the resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 67

The resin is prepared by combining 2.5 mL of HW-65S TOYOPEARL® resin with 2.5 mL dry acetone and 200 mg 1,1'-carbonyl diimidazole. The reaction is allowed to proceed for approximately 1 hour. Next, 250 mg 1,10-diaminodecane and 1 mL 1,4-dioxane are added to 4 mL of coupling buffer and combined with the resin. The reaction is allowed to proceed for approximately 12-18 hours, or overnight, at 4° C. Any remaining reactive sites are end-capped by adding 5 mL of a 1 M ethanolamine solution to the resin and reacting for approximately 1 hour.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 68

The resin is prepared by combining 2.5 mL of HW-65S TOYOPEARL® resin with 2.5 mL dry acetone and 200 mg 1,1'-carbonyl diimidazole. The reaction is allowed to proceed for approximately 1 hour. Next, 125 mg 1,10-diaminodecane, 125 µL ethanolamine and 1 mL 1,4-dioxane are added to 4 mL of coupling buffer and combined with the resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 69

The resin is prepared by combining 2.5 mL of HW-75F TOYOPEARL® resin with 2.5 mL dry acetone and 200 mg 1,1'-carbonyl diimidazole. The reaction is allowed to proceed for approximately 1 hour. Next, 250 mg 1,10-diaminodecane and 1 mL 1,4-dioxane are added to 4 mL of coupling buffer and combined with the resin. The reaction is allowed to proceed for approximately 12-18 hours, or overnight, at 4° C. Any remaining reactive sites are end-capped by adding 5 mL of a 1 M ethanolamine solution to the resin and reacting for approximately 1 hour.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 70

The resin is prepared by combining 2.5 mL of HW-75F TOYOPEARL® resin with 2.5 mL dry acetone and 200 mg 1,1'-carbonyl diimidazole. The reaction is allowed to proceed for approximately 1 hour. Next, 125 mg 1,10-diaminodecane, 125 µL ethanolamine and 1 mL 1,4-dioxane are added to 4 mL of coupling buffer and combined with the resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

The procedure for the AF-Tresyl-650M TOYOPEARL® resin is different than for the other TOYOPEARL® resins, since this resin comes with its hydroxyl functionalities pre-activated with tresyl chloride (an organic sulfonyl chloride), similar to cyanogen bromide-activated SEPHAROSE™ or 1,1'-carbonyl diimidazole-activated SEPHAROSE™.

Examples 71-72

The following general structure represents the affinity ligand bound to a solid support when synthesized using the linker and reaction conditions described in Examples 71-72:

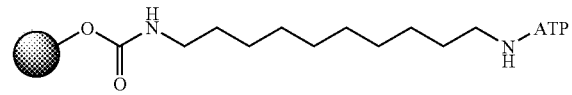

Example 71

The resin is prepared by allowing 0.5 g of AF-Tresyl-650M TOYOPEARL® resin to swell in 15 mL 1 mM HCl for approximately 10 minutes. The resin is then washed with 2 volumes of 1 mM HCl and 1 volume of water. Next, 250 mg 1,10-diaminodecane and 1 mL 1,4-dioxane are added to 4 mL of coupling buffer (0.2 M sodium phosphate buffer, pH=7.45) and combined with the resin. The reaction is allowed to proceed for approximately 12-18 hours, or overnight, at 4° C. Any remaining reactive sites are end-capped by adding 5 mL of a 1 M ethanolamine solution to the resin and reacting for approximately 1 hour.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 72

The resin is prepared by allowing 0.5 g of AF-Tresyl-650M TOYOPEARL® resin to swell in 15 mL HCl for approximately 10 minutes. The resin is then washed with 2 volumes of 1 mM HCl and 1 volume of water. Next, 125 mg 1,10-diaminodecane, 125 µL ethanolamine and 1 mL 1,4-dioxane are added to 4 mL of coupling buffer (0.2M sodium phosphate buffer, pH=7.45) and combined with the resin. The reaction is allowed to proceed for approximately 12-18 hours, or overnight, at 4° C.

The affinity ligand is prepared by adding 964 mg ATP, 720 µL 1-methyl imidazole and 1680 mg EDC to 10 mL water. The reaction is allowed to proceed for approximately 1 hour before combining with the prepared resin. The combined resin and affinity ligand are reacted for approximately 12-18 hours, or overnight.

Example 73

The following general structure represents the affinity ligand bound to a solid support when synthesized using the linker and reaction conditions described in Example 73:

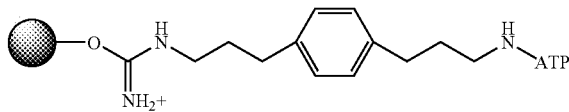

The resin was prepared by adding 190 mg 3-[4-(3-aminopropyl)-phenyl]-propylamine and 1.5 mL 1,4-dioxane to 3 mL coupling buffer and combining with 500 mg cyanogen bromide-activated SEPHAROSE™. The reaction was allowed to proceed for approximately 5 hours at room temperature.

The affinity ligand was prepared by adding 480 mg ATP, 360 µL 1-methyl imidazole and 840 mg EDC to 2.5 mL water, and reacting for approximately 1 hour at room temperature.

The resin and the affinity ligand were combined and allowed to react for approximately 12-18 hours, or overnight, at room temperature.

Example 74

The following general structure represents the affinity ligand bound to a solid support when synthesized using the linker and reaction conditions described in Example 74:

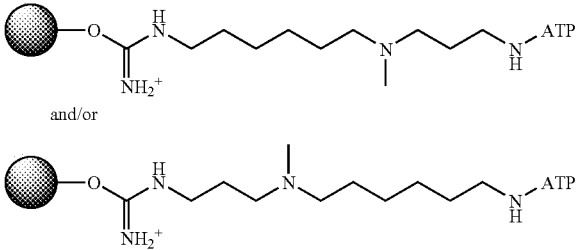

and/or

The resin was prepared by adding 190 mg N-(3-aminopropyl)-N-methyl-hexane-1,6-diamine and 0.75 mL 1,4-dioxane to 3 mL coupling buffer and combining with 500 mg cyanogen bromide-activated SEPHAROSE™. The reaction was allowed to proceed for approximately 5 hours at room temperature.

The affinity ligand was prepared by adding 480 mg ATP, 360 µL 1-methyl imidazole and 840 mg EDC to 2.5 mL water, and reacting for approximately 1 hour at room temperature.

The resin and the affinity ligand were combined and allowed to react for approximately 12-18 hours, or overnight, at room temperature.

Example 75

The following general structure represents the affinity ligand bound to a solid support when synthesized using the linker and reaction conditions described in Example 75:

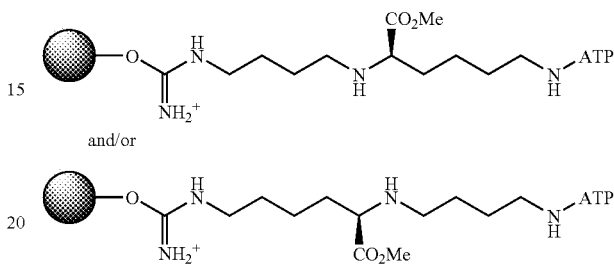

and/or

The resin was prepared by adding 350 mg 6-amino-2-(4-amino-butylamino)-hexanoic acid methyl ester and 1.4 mL 1,4-dioxane to 5.6 mL coupling buffer and combining with 500 mg cyanogen bromide-activated SEPHAROSE™. The reaction was allowed to proceed for approximately 5 hours at room temperature.

The affinity ligand was prepared by adding 480 mg ATP, 360 µL 1-methyl imidazole and 840 mg EDC to 2.5 mL water, and reacting for approximately 1 hour at room temperature.

The resin and the affinity ligand were combined and allowed to react for approximately 12-18 hours, or overnight, at room temperature.

Example 76

The following general structure represents the affinity ligand bound to a solid support when synthesized using the linker and reaction conditions described in Example 76:

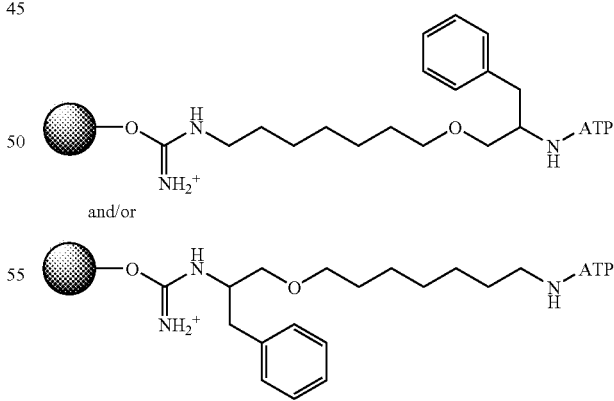

and/or

The resin was prepared by adding 260 mg 7-(2-amino-3-phenyl-propoxy)-heptylamine and 1.0 mL 1,4-dioxane to 4 mL coupling buffer and combining with 500 mg cyanogen bromide-activated SEPHAROSE™. The reaction was allowed to proceed for approximately 5 hours at room temperature.

The affinity ligand was prepared by adding 480 mg ATP, 360 μL 1-methyl imidazole and 840 mg EDC to 2.5 mL water, and reacting for approximately 1 hour at room temperature.

The resin and the affinity ligand were combined and allowed to react for approximately 12-18 hours, or overnight, at room temperature.

Example 77

The following general structure represents the affinity ligand bound to a solid support when synthesized using the linker and reaction conditions described in Example 77:

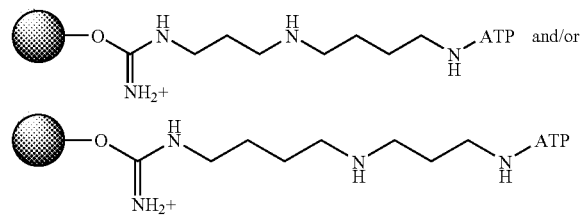

The resin was prepared by adding 105 mg spermidine and 0.5 mL 1,4-dioxane to 2.5 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 μL 1-methyl imidazole and 420 mg EDC to 2.5 mL water, and reacting for approximately 1 hour at room temperature.

The resin and the affinity ligand were combined and allowed to react for approximately 12-18 hours, or overnight, at room temperature.

Example 78

The following general structure represents the affinity ligand bound to a solid support when synthesized using the linker and reaction conditions described in Example 78:

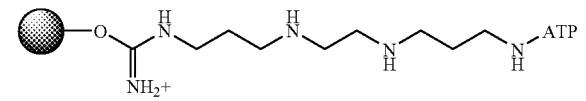

The resin was prepared by adding 127 mg bis(3-aminopropyl)-ethylene diamine and 0.5 mL 1,4-dioxane to 2.5 mL coupling buffer and combining with 500 mg cyanogen bromide-activated SEPHAROSE™. The reaction was allowed to proceed for approximately 2 hours at room temperature.

The affinity ligand was prepared by adding 240 mg ATP, 180 μL 1-methyl imidazole and 420 mg EDC to 2.5 mL water, and reacting for approximately 1 hour at room temperature.

The resin and the affinity ligand were combined and allowed to react for approximately 12-18 hours, or overnight, at room temperature.

Example 79

The following general structure represents the affinity ligand bound to a solid support when synthesized using the linker and reaction conditions described in Example 79:

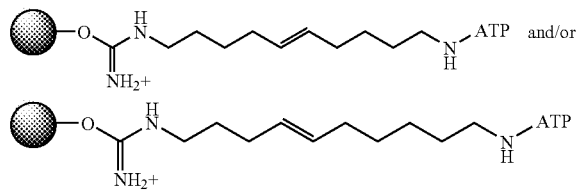

1,10 Diiodo-dec-5-ene is prepared as follows: 9-Borabicyclo[3.3.1]nonane (1 equiv.) is added to anhydrous THF at 0° C. followed by followed by 1,5,9-decatriene (4 equiv.). The reaction is warmed to ambient temperature and stirred for 1.5 h. The resulting solution is cooled to −20° and sodium methoxide (2 equiv.) is added followed by iodine (2 equiv.). The reaction mixture is stirred at −20° C. for 1.5 h, warmed to room temperature and stirred for an additional 1 h. The crude product is purified via silica gel chromatography. The appropriate fractions are pooled and concentrated in vacuo to afford 1,10-Diiodo-dec-5-ene.

The 1,10-Diiodo-dec-5-ene (1 equiv.) is dissolved in anhydrous acetone at ambient temperature followed by the addition of potassium phthalimide (4. equiv.). The reaction mixture is stirred until completion, washed with brine, dried over magnesium sulfate, and concentrated in vacuo. The crude product is purified via silica gel chromatography to afford 1,10-dipthalimido-dec-5-ene.

The 1,10-dipthalimido-dec-5-ene (1 equiv.) and hydrazine (2 equiv.) are stirred in ethanol at reflux. The reaction mixture is cooled to room temperature and the resulting solid is filtered off. The filtrate is purified via silica gel chromatography to yield 1,10 diamino-dec-5-ene.

200 mg of the linker arm and 1.5 ml 1,4-dioxane are added to 3 ml coupling buffer and combined with 500 mg cyanogen bromide-activated Sepharose. The reaction is allowed to proceed for about five hours. 480 mg ATP, 360 ml 1-methyl imidazole and 840 mg EDC are added to 2.5 ml water, allowed to react for one hour, and then combined the resin. The reaction is allowed to proceed overnight.

Example 80

The following general structure represents the affinity ligand bound to a solid support when synthesized using the linker and reaction conditions described in Example 80:

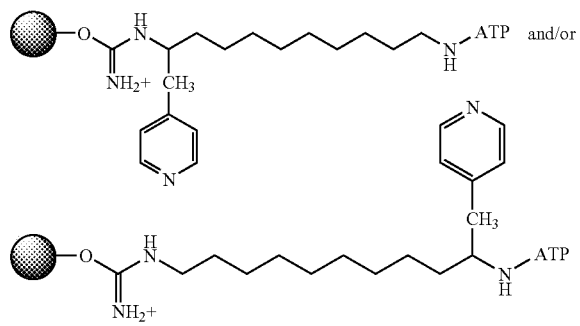

Magnesium (1.2 equiv.) is stirred in anhydrous ether under a nitrogen atmosphere and a catalytic amount of iodine is added. The mixture is heated to reflux and 4-bromomethylpyridine (1 equiv.) is added. The reaction is stirred until formation of the Grignard reagent is complete and 9-phthalimidononanal (1.5 equiv.) is added. The reaction mixture is stirred until completion, quenched with ammonium chloride, extracted with brine and concentrated in vacuo. The crude product is purified by silica gel chromatography to give 1-hydroxy-1-(4-pyridinyl)-10-phthalimidodecane.

1-Hydroxy-1-(4-pyridinyl)-10-phthalimidodecane (1 equiv.) is dissolved in THF with stirring. Phthalimide (1.5 equiv.) and triphenylphosphine (2.1 equiv.) are added to the solution and the resulting mixture is cooled to 0° C. Diisopropyl azodicarboxylate (2.0 equiv.) is added dropwise to the above solution and the reaction is stirred until completion. The resulting solid is filtered off and the filtrate is concentrated in vacuo. The crude product is purified by silica gel chromatography to yield 1,10-diphthalimido-1-pyridinyldecane.

1,10-diphthalimido-1-pyridinyldecane (1 equiv.) and hydrazine (2 equiv.) are stirred in ethanol at reflux. The reaction mixture is cooled to room temperature and the resulting solid is filtered off. The filtrate is purified by silica gel chromatography to yield 1,10-diamino-1-pyridinyldecane.

250 mg of linker arm and 1.5 ml 1,4-dioxane is added to 3 ml coupling buffer and combined with 500 mg cyanogen bromide-activated Sepharose. The reaction is allowed to proceed for 5 hours. 480 mg ATP, 360 ml 1-methyl-imidazole and 840 mg EDC are added to 2.5 ml water, reacted for about one hour, and combined with the resin. The reaction is allowed to proceed overnight.

Examples 81-83

The following general structures represent the affinity ligand bound to a solid support when synthesized using the linker and reaction conditions described in Examples 81-83:

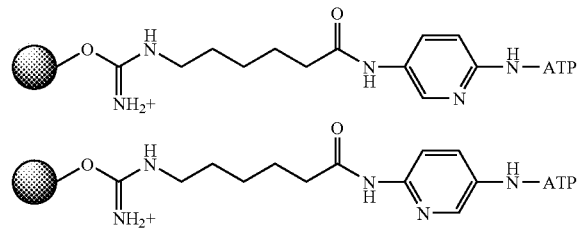

CH-activated SEPHAROSE™ 4B (Sigma) is used for these examples.

Example 81

50 mg of 2,5-diaminopyridine and 0.2 mL 1,4-dioxane are added to 0.8 mL coupling buffer and combined with 200 mg CH-activated SEPHAROSE™. The reaction is allowed to proceed for approximately 2 hours at room temperature.

The affinity ligand is prepared by combining 100 mg ATP, 74 μL 1-methyl imidazole and 172 mg EDC to 1.5 mL water, and reacting for approximately 1 hour at room temperature.

The resin and the affinity ligand are combined and allowed to react for approximately 12-18 hours, or overnight, at room temperature.

Example 82

40 mg of 2,5-diaminopyridine, 10 μL ethanolamine and 0.2 mL 1,4-dioxane are added to 0.8 mL coupling buffer and combined with 200 mg CH-activated SEPHAROSE™. The reaction is allowed to proceed for approximately 2 hours at room temperature.

The affinity ligand is prepared by combining 100 mg ATP, 74 μL 1-methyl imidazole and 172 mg EDC to 1.5 mL water, and reacting for approximately 1 hour at room temperature.

Example 83

30 mg of 2,5-diaminopyridine, 20 μL ethanolamine, and 0.2 mL 1,4-dioxane are added to 0.8 mL coupling buffer and combined with 200 mg CH-activated SEPHAROSE™. The reaction is allowed to proceed for approximately 2 hours at room temperature.

The affinity ligand is prepared by combining 100 mg ATP, 74 μL 1-methyl imidazole and 172 mg EDC to 1.5 mL water, and reacting for approximately 1 hour at room temperature.

The resin and the affinity ligand are combined and allowed to react for approximately 12-18 hours, or overnight, at room temperature.

Examples 84-89

The following general structure represents the affinity ligand bound to a solid support when synthesized using the linker and reaction conditions described in Examples 84-89:

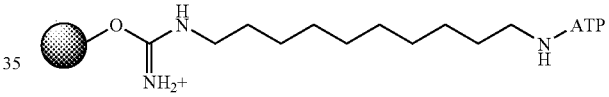

Cyanogen bromide-activated SEPHAROSE™ 4B (Sigma) is used for these examples.

Example 84

112.5 mg of 1,10-diaminodecane, 12.5 mg glycine, and 0.5 mL 1,4-dioxane are added to 2 mL coupling buffer and combined with 0.5 mg cyanogen bromide-activated SEPHAROSE™. The reaction is allowed to proceed for approximately 2 hours at room temperature.

The affinity ligand is prepared by combining 240 mg ATP, 180 μL 1-methyl imidazole and 420 mg EDC to 2.5 mL water, and reacting for approximately 1 hour at room temperature.

The resin and the affinity ligand are combined and allowed to react for approximately 12-18 hours, or overnight, at room temperature.

Example 85

93.75 mg of 1,10-diaminodecane, 31.25 mg glycine, and 0.5 mL 1,4-dioxane are added to 2 mL coupling buffer and combined with 0.5 mg cyanogen bromide-activated SEPHAROSE™. The reaction is allowed to proceed for approximately 2 hours at room temperature.

The affinity ligand is prepared by combining 240 mg ATP, 180 μL 1-methyl imidazole and 420 mg EDC to 2.5 mL water, and reacting for approximately 1 hour at room temperature.

The resin and the affinity ligand are combined and allowed to react for approximately 12-18 hours, or overnight, at room temperature.

Example 86

62.5 mg of 1,10-diaminodecane, 62.5 mg glycine, and 0.5 mL 1,4-dioxane are added to 2 mL coupling buffer and combined with 0.5 mg cyanogen bromide-activated SEPHAROSE™. The reaction is allowed to proceed for approximately 2 hours at room temperature.

The affinity ligand is prepared by combining 240 mg ATP, 180 µL 1-methyl imidazole and 420 mg EDC to 2.5 mL water, and reacting for approximately 1 hour at room temperature.

The resin and the affinity ligand are combined and allowed to react for approximately 12-18 hours, or overnight, at room temperature.

Example 87

112.5 mg of 1,10-diaminodecane, 12.5 mg tris(hydroxymethyl)aminomethane, and 0.5 mL 1,4-dioxane are added to 2 mL coupling buffer and combined with 0.5 mg cyanogen bromide-activated SEPHAROSE™. The reaction is allowed to proceed for approximately 2 hours at room temperature.

The affinity ligand is prepared by combining 240 mg ATP, 180 µL 1-methyl imidazole and 420 mg EDC to 2.5 mL water, and reacting for approximately 1 hour at room temperature.

The resin and the affinity ligand are combined and allowed to react for approximately 12-18 hours, or overnight, at room temperature.

Example 88

93.75 mg of 1,10-diaminodecane, 31.25 mg tris(hydroxymethyl)aminomethane, and 0.5 mL 1,4-dioxane are added to 2 mL coupling buffer and combined with 0.5 mg cyanogen bromide-activated SEPHAROSE™. The reaction is allowed to proceed for approximately 2 hours at room temperature.

The affinity ligand is prepared by combining 240 mg ATP, 180 µL 1-methyl imidazole and 420 mg EDC to 2.5 mL water, and reacting for approximately 1 hour at room temperature.

The resin and the affinity ligand are combined and allowed to react for approximately 12-18 hours, or overnight, at room temperature.

Example 89

62.25 mg of 1,10-diaminodecane, 62.25 mg tris(hydroxymethyl)aminomethane, and 0.5 mL 1,4-dioxane are added to mL coupling buffer and combined with 0.5 mg cyanogen bromide-activated SEPHAROSE™. The reaction is allowed to proceed for approximately 2 hours at room temperature.

The affinity ligand is prepared by combining 240 mg ATP, 180 µL 1-methyl imidazole and 420 mg EDC to 2.5 mL water, and reacting for approximately 1 hour at room temperature.

The resin and the affinity ligand are combined and allowed to react for approximately 12-18 hours, or overnight, at room temperature.

Examples 90-96

The following general structure represents the affinity ligand bound to a solid support when synthesized using the linker and reaction conditions described in Examples 90-96:

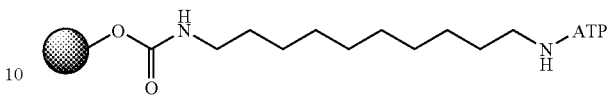

Trisacryl resin GF 2000 M (BioSepra) or Ultrogel AcA 22 (BioSepra) resin is used for these examples. The general procedure for these resins is the same as that described for the TOYOPEARL® and SEPHACRYL™ resins as described above.

Example 90

2.5 ml Trisacryl GF 2000 M resin was combined with 2.5 ml dry acetone and 200 mg 1,1'-carbonyl diimidazole. The reaction is allowed to proceed for approximately 1 hour at room temperature. 250 mg of 1,10-diaminodecane and 1 mL 1,4-dioxane are added to 4 mL coupling buffer and combined with the resin. The reaction is allowed to proceed for approximately 12-18 hours, or overnight, at 4° C. 5 mL of a 1 M ethanolamine solution are then added to the resin and allowed to react at room temperature for approximately 1 hour.

The affinity ligand is prepared by combining 964 mg ATP, 720 µL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 91

2.5 ml Trisacryl GF 2000 M resin was combined with 2.5 ml dry acetone and 200 mg 1,1'-carbonyl diimidazole. The reaction is allowed to proceed for approximately 1 hour at room temperature. 165 mg of 1,10-diaminodecane, 85 µL ethanolamine and 1 mL 1,4-dioxane are added to 4 mL coupling buffer and combined with the resin. The reaction is allowed to proceed for approximately 12-18 hours, or overnight, at 4° C. 5 mL of a 1 M ethanolamine solution are then added to the resin and allowed to react at room temperature for approximately 1 hour.

The affinity ligand is prepared by combining 964 mg ATP, 720 µL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 92

2.5 ml Trisacryl GF 2000 M resin was combined with 2.5 ml dry acetone and 200 mg 1,1'-carbonyl diimidazole. The reaction is allowed to proceed for approximately 1 hour at room temperature. 82 mg of 1,10-diaminodecane, 168 µL ethanolamine and 1 mL 1,4-dioxane are added to 4 mL coupling buffer and combined with the resin. The reaction is allowed to proceed for approximately 12-18 hours, or overnight, at 4° C. 5 mL of a 1M ethanolamine solution are then added to the resin and allowed to react at room temperature for approximately 1 hour.

The affinity ligand is prepared by combining 964 mg ATP, 720 μL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 93

2.5 ml Ultrogel AcA 22 resin was combined with 2.5 ml dry acetone and 200 mg 1,1'-carbonyl diimidazole. The reaction is allowed to proceed for approximately 1 hour at room temperature. 250 mg of 1,10-diaminodecane and 1 mL 1,4-dioxane are added to 4 mL coupling buffer and combined with the resin. The reaction is allowed to proceed for approximately 12-18 hours, or overnight, at 4° C. 5 mL of a 1 M ethanolamine solution are then added to the resin and allowed to react at room temperature for approximately 1 hour.

The affinity ligand is prepared by combining 964 mg ATP, 720 μL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 94

2.5 ml Ultrogel AcA 22 resin was combined with 2.5 ml dry acetone and 200 mg 1,1'-carbonyl diimidazole. The reaction is allowed to proceed for approximately 1 hour at room temperature. 165 mg of 1,10-diaminodecane, 85 μL ethanolamine and 1 mL 1,4-dioxane are added to 4 mL coupling buffer and combined with the resin. The reaction is allowed to proceed for approximately 12-18 hours, or overnight, at 4° C. 5 mL of a 1M ethanolamine solution are then added to the resin and allowed to react at room temperature for approximately 1 hour.

The affinity ligand is prepared by combining 964 mg ATP, 720 μL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 95

2.5 ml Ultrogel AcA 22 resin was combined with 2.5 ml dry acetone and 200 mg 1,1'-carbonyl diimidazole. The reaction is allowed to proceed for approximately 1 hour at room temperature. 82 mg of 1,10-diaminodecane, 168 μL ethanolamine and 1 mL 1,4-dioxane are added to 4 mL coupling buffer and combined with the resin. The reaction is allowed to proceed for approximately 12-18 hours, or overnight, at 4° C. 5 mL of a 1M ethanolamine solution are then added to the resin and allowed to react at room temperature for approximately 1 hour.

The affinity ligand is prepared by combining 964 mg ATP, 720 μL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 96

2.5 ml Ultrogel AcA 22 resin was combined with 2.5 ml dry acetone and 200 mg 1,1'-carbonyl diimidazole. The reaction is allowed to proceed for approximately 1 hour at room temperature. 25 mg of 1,10-diaminodecane, 225 μL ethanolamine and 1 mL 1,4-dioxane are added to 4 mL coupling buffer and combined with the resin. The reaction is allowed to proceed for approximately 12-18 hours, or overnight, at 4° C. 5 mL of a 1 M ethanolamine solution are then added to the resin and allowed to react at room temperature for approximately 1 hour.

The affinity ligand is prepared by combining 964 mg ATP, 720 μL 1-methyl imidazole and 1680 mg EDC to 10 mL water, and reacting for approximately 1 hour at room temperature.

The resin and the affinity ligand are combined and allowed to react for approximately 12-18 hours, or overnight, at room temperature.

Example 97

The following structure represents an ATP analog out of which an alkyl linked nucleotide was made using the conditions described in Example 97:

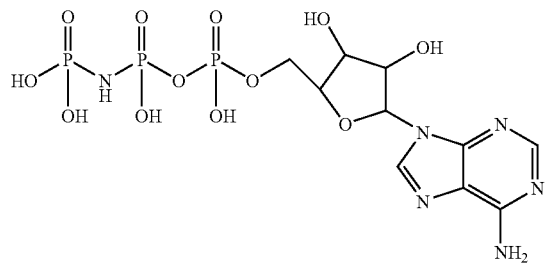

13.5 mg of 1,10-diaminodecane, 13.5 μl ethanolamine and 105 μl 1,4-dioxane are added to 419 μl coupling buffer and combined with 105 mg cyanogen-bromide-activated SEPHAROSE™. The reaction is allowed to proceed for approximately 2 hours at room temperature. 29 mg adenyl-imido-diphosphate (Calbiochem®, San Diego Calif.), 22.5 μl 1-methyl imidazole and 52.5 mg EDC are added to 625 μl water, and the reaction is allowed to proceed for one hour. The resin is combined with the ligand, and the reaction is allowed to proceed overnight.

Example 98

The following structure represents an ATP analog out of which an alkyl linked nucleotide was made using the conditions described in Example 98:

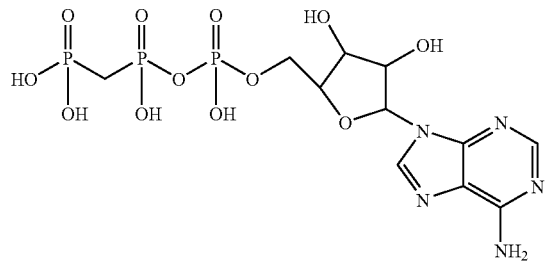

13.5 mg of 1,10-diaminodecane, 13.5 µl ethanolamine and 105 µl 1,4-dioxane are added to 419 µl coupling buffer and combined with 105 mg cyanogen-bromide-activated SEPHAROSE™. The reaction is allowed to proceed for approximately 2 hours at room temperature. 30 mg β,γ-methylene-ATP (Calbiochem®, San Diego Calif.), 22.5 µl 1-methyl imidazole and 52.5 mg EDC are added to 625 µl water, and the reaction is allowed to proceed for one hour. The resin is combined with the ligand, and the reaction is allowed to proceed overnight.

Example 99

The following structure represents an ATP analog out of which an alkyl linked nucleotide was made using the conditions described in Example 99:

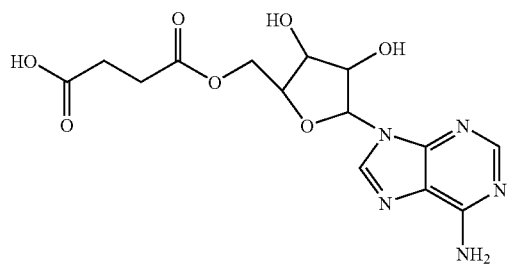

16 mg of 1,10-diaminodecane, 16 µl ethanolamine and 125 µl 1,4-dioxane are added to 500 µl coupling buffer and combined with 125 mg cyanogen bromide-activated SEPHAROSE™. The reaction is allowed to proceed for approximately 2 hours at room temperature. 20 mg adenosine-5'-succinate (Sigma, St. Lous, Mo.), 22.5 µl 1-methyl imidazole and 52.5 mg EDC are added to 625 µl water, and the reaction is allowed to proceed for one hour. The resin is combined with the ligand, and the reaction is allowed to proceed overnight.

Example 100

The following structure represents an ATP analog out of which an alkyl linked nucleotide was made using the conditions described in Example 100:

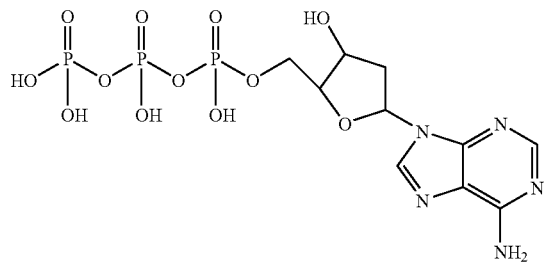

16 mg of 1,10-diaminodecane, 16 µl ethanolamine and 125 µl 1,4-dioxane are added to 500 µl coupling buffer and combined with 125 mg cyanogen-bromide-activated SEPHAROSE™. The reaction is allowed to proceed for approximately 2 hours at room temperature. 29 mg 2-deoxoy-ATP (Sigma, St. Lous, Mo.), 22.5 µl 1-methyl imidazole and 52.5 mg EDC are added to 625 µl water, and the reaction is allowed to proceed for one hour. The resin is combined with the ligand, and the reaction is allowed to proceed overnight.

Examples 101-105

The alkyl-linked nucleotide non-homogeneous solid supports of Examples 101-105 are made in three steps: the adenosine derivative is prepared; phosphorylated, and then attached to the resin-linker arm combination. For each of examples 99-103, the adenosine derivatives are phosphorylated as follows. The adenosine derivatives are dissovled in trimethyl phosphate (5-12 mL) and cooled to about 0° C. After stirring for 10 minutes, phosphorous oxychloride (1.8 equivalents) is added dropwise. The reaction mixture is stirred at 0° C. for 6 hours. Tributylamine (5.4 equivalents) is added followed immediately by 0.5 M tributylammonium pyrophosphate (4 equivalents) and stirring is continued for about 15 additional minutes. The reaction is quenched by the addition of 0.2 M triethylammonium bicarbonate (40-50 mL). The reaction mixture is then stirred at room temperature for 15 hours, and then lyophilized. The crude preparation is then purified on a Sephadex™ DEAE-25-ion-exchange resin, and eluted with water following a gradient of TEAB buffer (0.05 M to 0.5 M). The appropriate fractions are then combined.

Example 101

The following structure represents an ATP analog synthesized using the conditions described in Example 101:

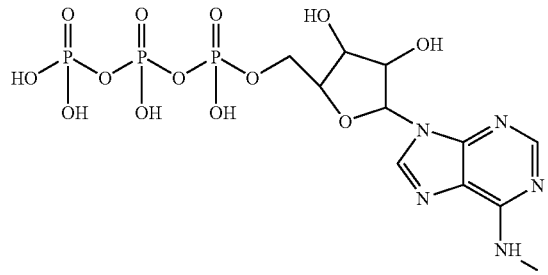

1.016 g 6-chloropurine riboside and 8.82 mL methylamine (33% in ethyl alcohol) are combined and heated to 90° C. in a sealed reaction vessel for about 22 hours. The reaction vessel is cooled in an ice bath for about 30 minutes to allow formation of a solid precipitate. The precipitate is filtered and washed with ice-cold ethyl alcohol (3×25 mL) and dried to 0.66 g of $N^6$-methyladenosine in 66% yield.

16 mg 1,10-diaminodecane, 16 µl ethanolamine and 125 µl 1,4-dioxane are added to 500 µl coupling buffer and combined with 125 mg cyanogen bromide-activated Sepharose™. The reaction is allowed to proceed for about 2 hours. 202 mg ligand, 90 µl 1-methyl imidazole and 210 mg EDC are added to 1 ml water and allowed to react to about one hour. The ligand is then added to the resin and the reaction is allowed to proceed overnight.

Example 102

The following structure represents an ATP analog synthesized using the conditions described in Example 102:

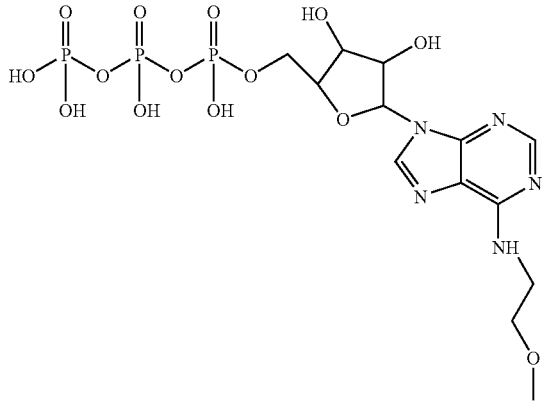

547 mg 6-chloropurine riboside, 0.882 mL 2-methoxyethylamine, and 5.0 mL ethyl alcohol are combined and heated to 90° C. in a sealed reaction vessel for about 22 hours. The ligand is then purified by silica gel chromatography using 8:1 methylene chloride:methanol to yield $N^6$-(2-methoxyethyl)-adenosine (0.61 g, 98% yield.

16 mg 1,10-diaminodecane, 16 µl ethanolamine and 125 µl 1,4-dioxane are added to 500 µl coupling buffer and combined with 125 mg cyanogen bromide-activated Sepharose™. The reaction is allowed to proceed for about 2 hours. 154 mg ligand, 90 µl 1-methyl imidazole and 210 mg EDC are added to 1 ml water and allowed to react to about one hour. The ligand is then added to the resin and the reaction is allowed to proceed overnight.

Example 103

The following structure represents an ATP analog synthesized using the conditions described in Example 103:

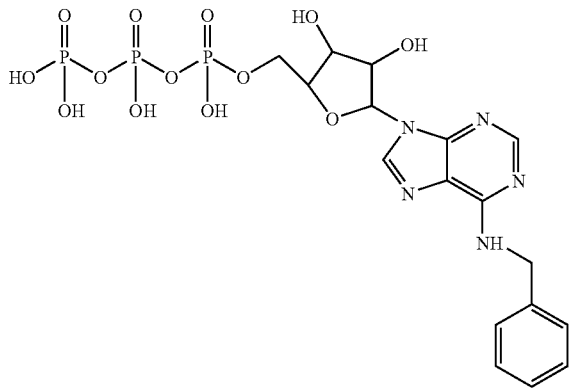

473 mg 6-chloropurine riboside, 0.54 mL 2-benzylamine, 0.69 ml triethylamine, and 5.0 mL of ethyl alcohol are combined and heated to 90° C. in a sealed reaction vessel for about 18 hours. The reaction vessel is cooled in an ice bath for about 30 minutes to allow formation of a solid precipitate. The precipitate is filtered and washed with ice-cold ethyl alcohol (3×25 mL) and dried to yield 0.51 g of $N^6$-benzoyladenosine (86% yield).

16 mg 1,10-diaminodecane, 16 µl ethanolamine and 125 µl 1,4-dioxane are added to 500 µl coupling buffer and combined with 125 mg cyanogen bromide-activated Sepharose™. The reaction is allowed to proceed for about 2 hours. 160.8 mg ligand, 90 µl 1-methyl imidazole and 210 mg EDC are added to 1 ml water and allowed to react to about one hour. The ligand is then added to the resin and the reaction is allowed to proceed overnight.

Example 104

The following structure represents an ATP analog synthesized using the conditions described in Example 104:

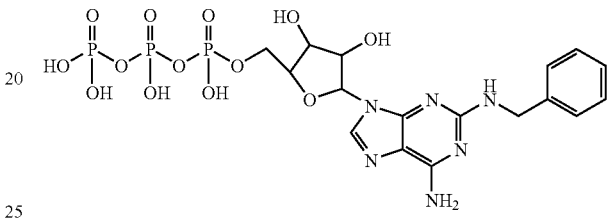

400 mg 2-chloroadenosine hemihydrate, 0.42 mL 2-benzylamine, 0.54 ml triethylamine, and 5.0 mL of ethyl alcohol are combined and heated to 90° C. in a sealed reaction vessel for about 96 hours. The ligand is then purified by silica gel chromatography using 20:1; methylene chloride:methanol to yield 0.11 g of $N^2$-benzyladenosine (22%).

16 mg 1,10-diaminodecane, 16 µl ethanolamine and 125 µl 1,4-dioxane are added to 500 µl coupling buffer and combined with 125 mg cyanogen bromide-activated Sepharose™. The reaction is allowed to proceed for about 2 hours. 120 mg ligand, 67.5 µl 1-methyl imidazole and 157.5 mg EDC are added to 1 ml water and allowed to react to about one hour. The ligand is then added to the resin and the reaction is allowed to proceed overnight.

Example 105

The following structure represents an ATP analog synthesized using the conditions described in Example 105:

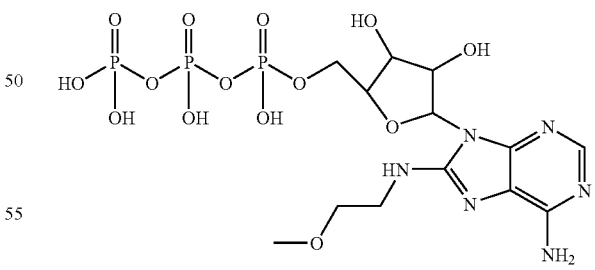

507 mg 8-bromoadenosine, 0.631 mL 2-methoxyethylamine, and 5.0 mL of ethyl alcohol are combined and heated to 90° C. in a sealed reaction vessel for about 168 hours. The ligand is then purified by silica gel chromatography using 4:1, methylene chloride:methanol to yield 0.52 g of $N^8$-(2-methoxyethyl)-adenosine (99% yield) as a clear, viscous oil.

16 mg 1,10-diaminodecane, 16 µl ethanolamine and 125 µl 1,4-dioxane are added to 500 µl coupling buffer and combined with 125 mg cyanogen bromide-activated Sepharose™. The reaction is allowed to proceed for about 2 hours. 157.2 mg ligand, 90 µl 1-methyl imidazole and 210 mg EDC are added to 1 ml water and allowed to react to about one hour. The ligand is then added to the resin and the reaction is allowed to proceed overnight.

While this invention has been particularly shown and described with references to preferred embodiments thereof, it will be understood by those skilled in the art that various changes in form and details may be made therein without departing from the scope of the invention encompassed by the appended claims.

Various publications, patent applications and patents are cited herein, the disclosures of which are incorporated by reference in their entireties.

The invention claimed is:

1. An alkyl-linked nucleotide non-homogeneous solid support consisting essentially of the general formula:

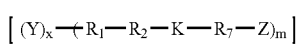

wherein Y is a solid support; x=1; $R_1$ is a covalent bond between Y and $R_2$, or $R_1$ is a divalent acyl group —C(=Q)—, wherein Q is O or $NH_2^+$; K is NH; $R_7$ is $(P)_n$ where P is a phosphate or a thiophosphate and n is at least one; and m is at least one; Z is a 5'-nucleosidyl group or a 5'-nucleosidyl group wherein the 5'-nucleosidyl group is not naturally occurring, or a derivative thereof; and —$R_2$—K— is selected from the group consisting of:

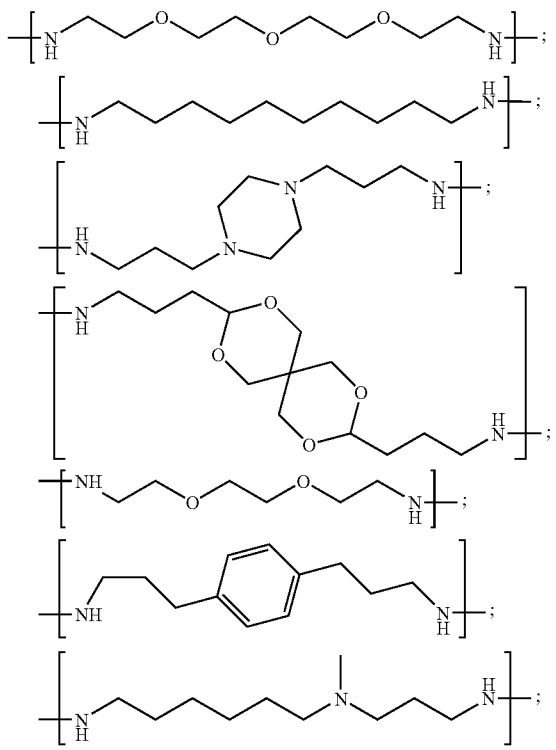

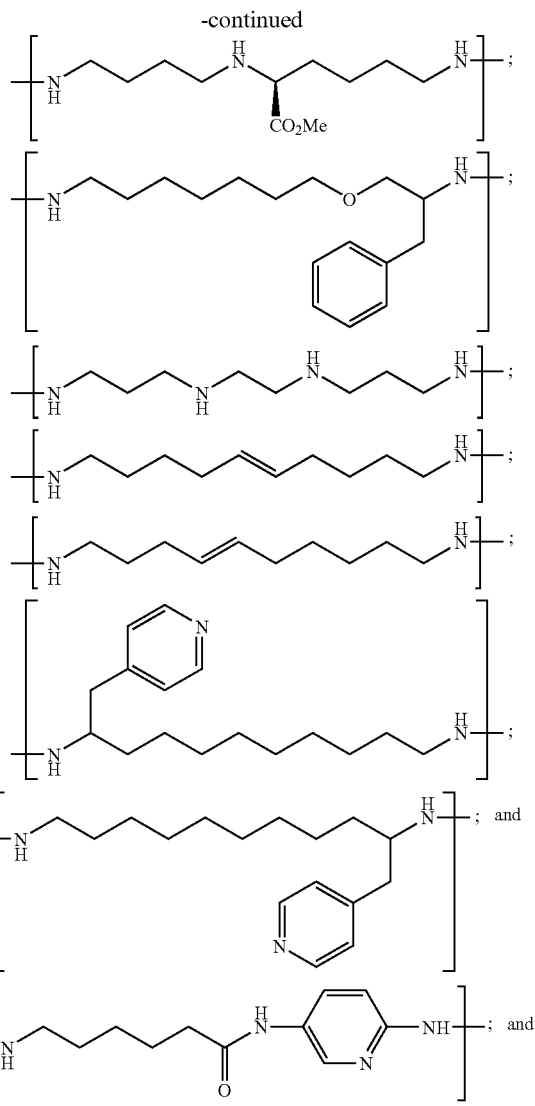

wherein the solid support has a loading of an alkyl-linked nucleotide having a range of about 20% to about 50%.

2. The alkyl-linked nucleotide non-homogeneous solid support of claim 1, wherein the solid support includes at least one member selected from the group consisting of an acrylamide, agarose, methacrylate, cellulose, nylon, silica, glass, ceramic, a magnetized particle, nitrocellulose, polystyrene, a thermoresponsive polymer, and derivatives thereof.

3. The alkyl-linked nucleotide non-homogeneous solid support of claim 1, wherein the solid support is a beaded agarose.

4. The alkyl-linked nucleotide non-homogeneous solid support of claim 1, wherein the 5'-nucleosidyl group is selected from the group consisting of a -5-deoxy-5'-adenosinyl radical, a -5-deoxy-5'-guanosinyl radical, a -5-deoxy-5'-cytidinyl radical, a -5-deoxy-5'-thymidinyl radical, and a -5-deoxy-5'-uridinyl radical, or an analog thereof.

5. The alkyl-linked nucleotide non-homogeneous solid support of claim 4, wherein the 5'-nucleosidyl group is a -5-deoxy-5'-adenosinyl radical, said alkyl-linked nucleotide non-homogeneous solid support consisting essentially of the general structure:

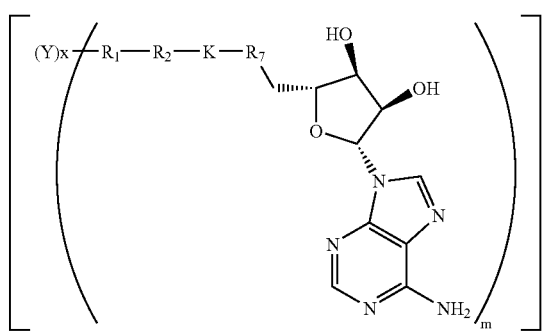

or an ionized variant or a salt thereof.

6. The alkyl-linked nucleotide non-homogeneous solid support of claim 4, wherein the 5'-nucleosidyl group is a -5-deoxy-5'-guanosinyl radical, said alkyl-linked nucleotide non-homogeneous solid support consisting essentially of the general structure:

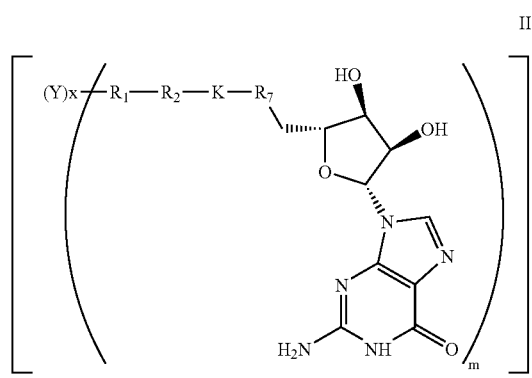

or an ionized variant or a salt thereof.

7. The alkyl-linked nucleotide non-homogeneous solid support of claim 4, wherein the 5'-nucleosidyl group is a -5-deoxy-5'-thymidinyl radical, said alkyl-linked nucleotide non-homogeneous solid support consisting essentially of the general structure:

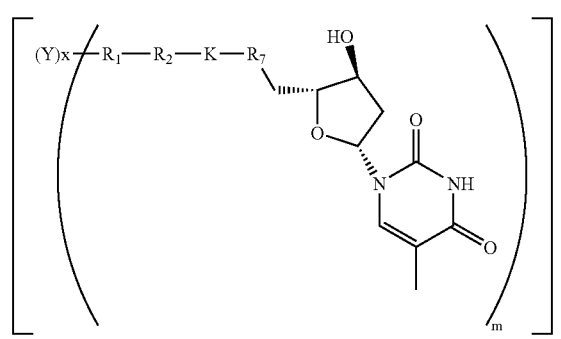

or an ionized variant or a salt thereof.

8. The alkyl-linked nucleotide non-homogeneous solid support of claim 4, wherein the 5'-nucleosidyl group is a -5-deoxy-5'-cytidinyl radical, said alkyl-linked nucleotide non-homogeneous solid support consisting essentially of the general structure:

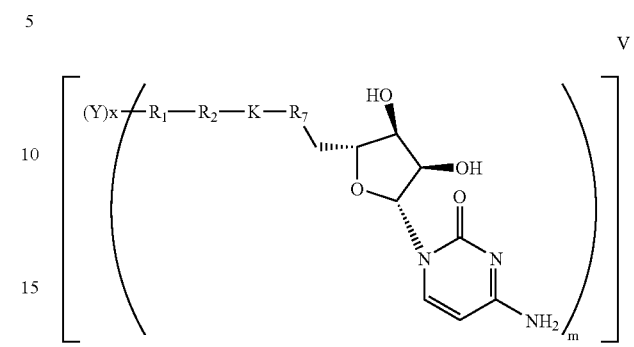

or an ionized variant or a salt thereof.

9. The alkyl-linked nucleotide non-homogeneous solid support of claim 4, wherein the 5'-nucleosidyl group is a -5-deoxy-5'-uridinyl radical, said alkyl-linked nucleotide non-homogeneous solid support consisting essentially of the general structure:

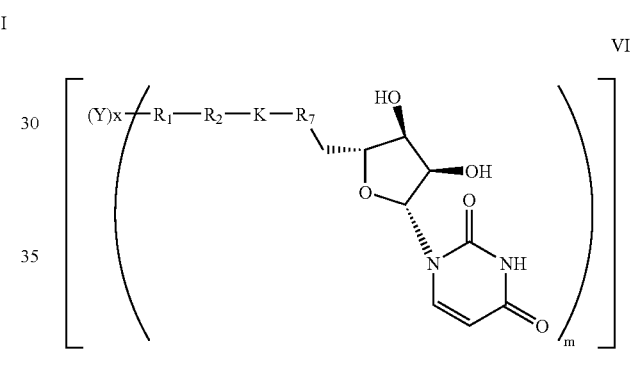

or an ionized variant or a salt thereof.

10. The alkyl-linked nucleotide non-homogeneous solid support of claim 1, wherein:
$R_1$ is —C(=$NH_2^+$)—;
$R_2$ is:

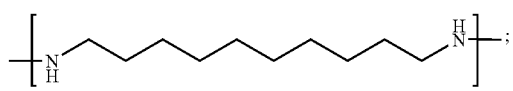

P is phosphate; and
n is 3.

11. A method for synthesizing a nucleotide affinity medium consisting essentially of the general formula:

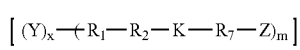

comprising the steps of:
a) coupling at least one linker to a solid support in a suitable coupling buffer, wherein said linker is $R_2$ or a combination of $R_1$ and $R_2$;
b) end-capping at least a portion of reactive sites remaining on said solid support after said coupling step; and c) reacting a terminal phosphate or thiophosphate group of a nucleotide with said linker coupled to said solid support, wherein Y is a solid support; x=1; $R_1$ is a covalent bond between Y and $R_2$, or $R_1$ is a divalent acyl group —C(=Q)—, wherein Q is O or $NH_2+$; K is NH; $R_7$ is $(P)_n$ where P is a phosphate or thiophosphate and n is at least one; Z is a 5'-nucleosidyl group or a 5'-nucleosidyl group wherein the 5'-nucleosidyl group is not naturally occurring, or a derivative thereof; and m is at least one;

and —$R_2$—K— is selected from the group consisting of:

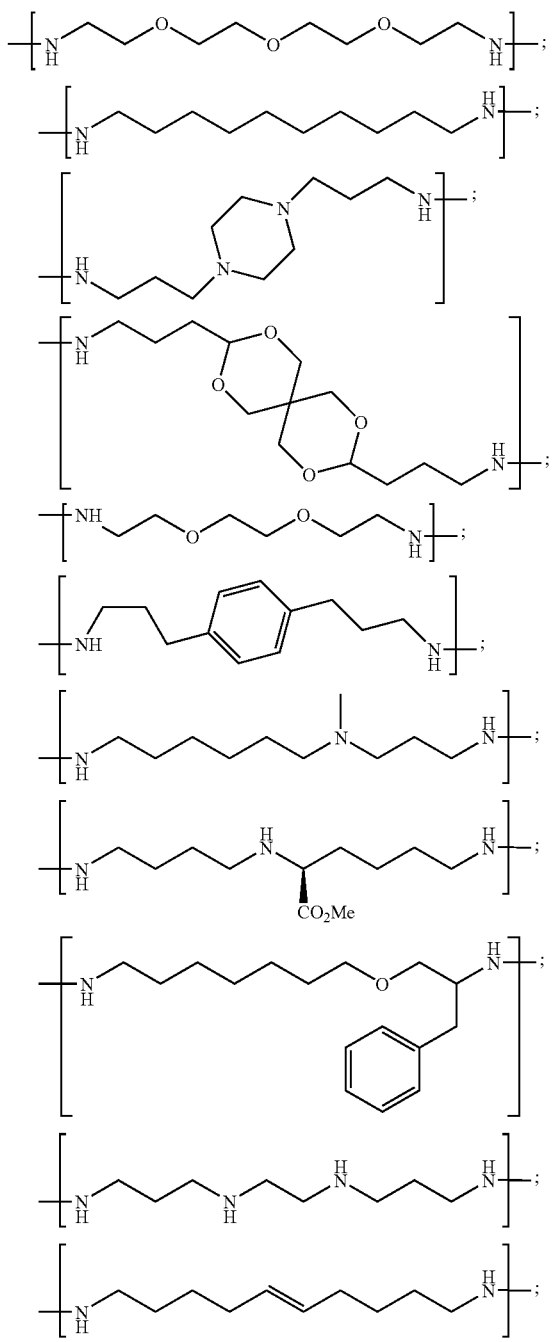

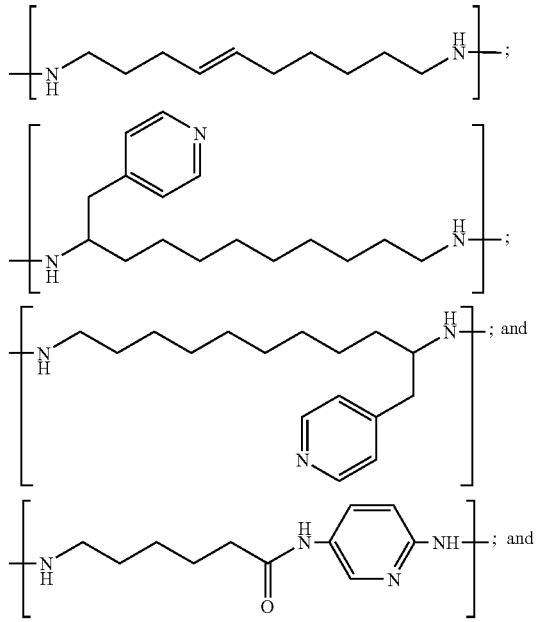

wherein the solid support has a loading of an alkyl-linked nucleotide having a range of about 20% to about 50%.

12. A method for screening a test compound comprising the steps of:
a) contacting a proteome with a nucleotide affinity medium consisting essentially of the general formula:

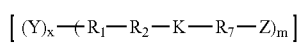

wherein Y is a solid support; x=1; $R_1$ is a covalent bond between Y and $R_2$, or $R_1$ is a divalent acyl group —C(=Q)—, wherein Q is O or $NH_2+$, K is NH; $R_7$ is $(P)_n$ where P is a phosphate or thiophosphate and n is at least one Z is a 5'-nucleosidyl group or a 5'-nucleosidyl group wherein the nucleoside is not naturally occurring, or a derivative thereof; and m is at least one;

and —$R_2$—K— is selected from the group consisting of:

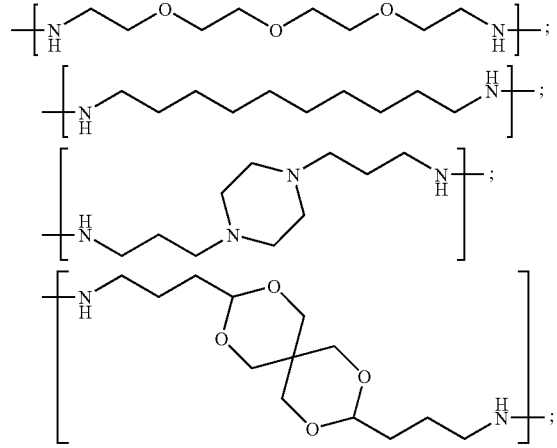

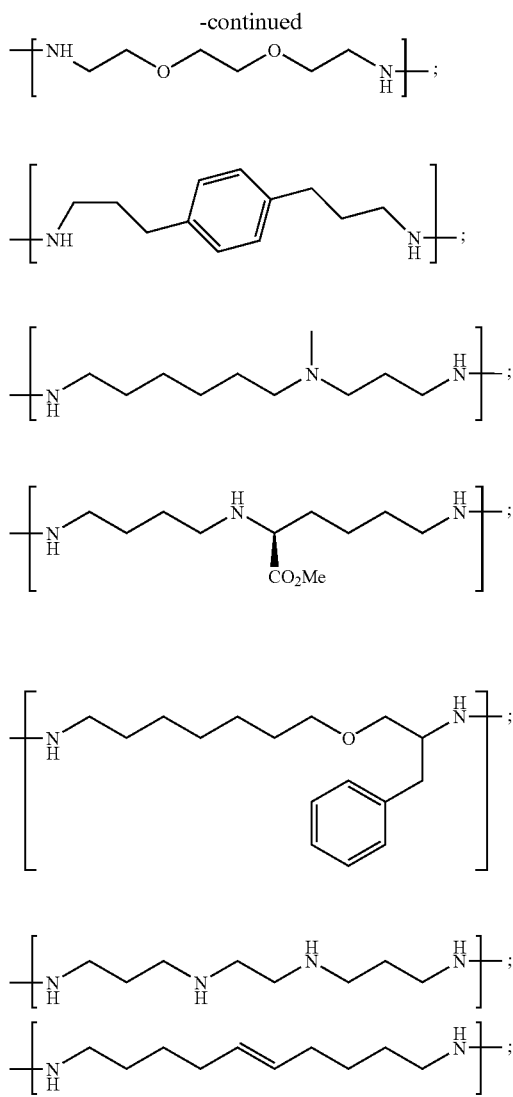

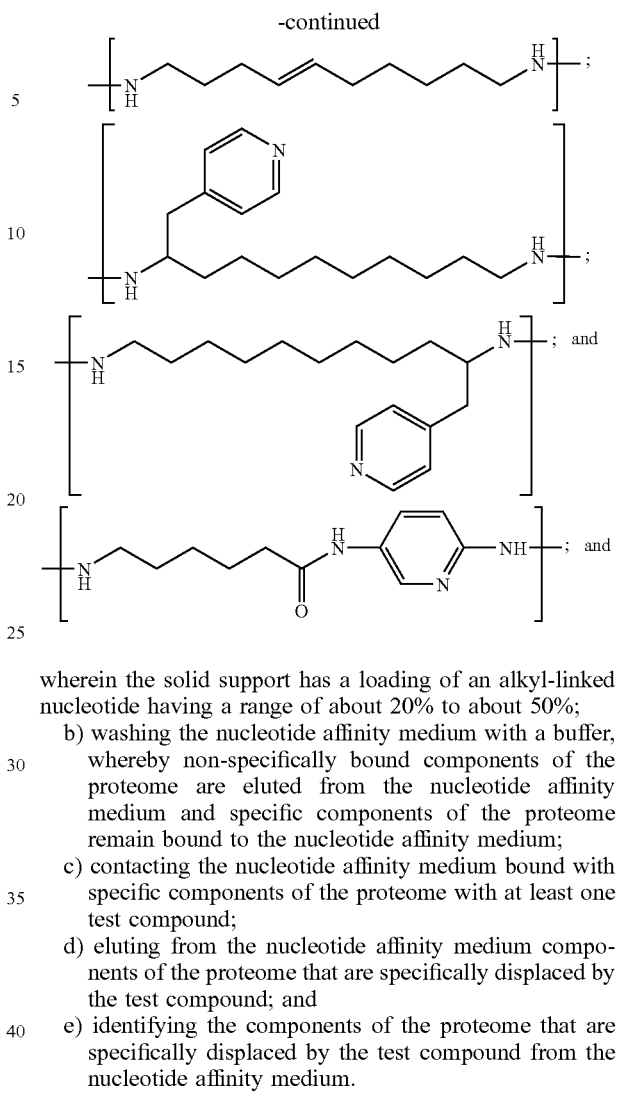

wherein the solid support has a loading of an alkyl-linked nucleotide having a range of about 20% to about 50%;

b) washing the nucleotide affinity medium with a buffer, whereby non-specifically bound components of the proteome are eluted from the nucleotide affinity medium and specific components of the proteome remain bound to the nucleotide affinity medium;

c) contacting the nucleotide affinity medium bound with specific components of the proteome with at least one test compound;

d) eluting from the nucleotide affinity medium components of the proteome that are specifically displaced by the test compound; and e) identifying the components of the proteome that are specifically displaced by the test compound from the nucleotide affinity medium.

* * * * *

UNITED STATES PATENT AND TRADEMARK OFFICE
CERTIFICATE OF CORRECTION

PATENT NO.       : 7,371,852 B2                                     Page 1 of 4
APPLICATION NO.  : 10/762078
DATED            : May 13, 2008
INVENTOR(S)      : Hardeman et al.

It is certified that error appears in the above-identified patent and that said Letters Patent is hereby corrected as shown below:

Column 5
Lines 3-14

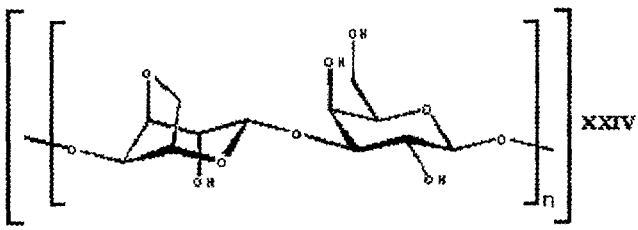

should be

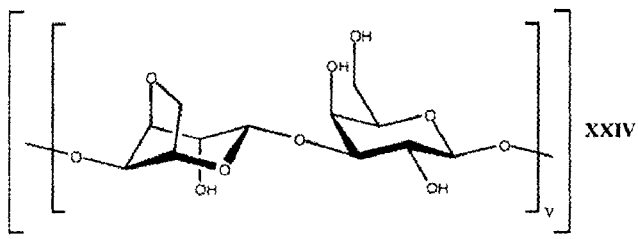

Column 26
Lines 44-51

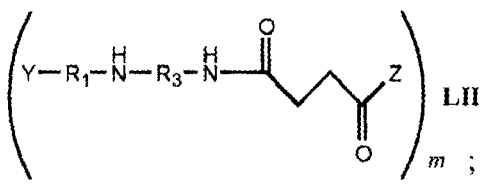

should be

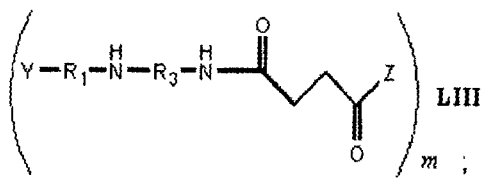

UNITED STATES PATENT AND TRADEMARK OFFICE
CERTIFICATE OF CORRECTION

PATENT NO. : 7,371,852 B2
APPLICATION NO. : 10/762078
DATED : May 13, 2008
INVENTOR(S) : Hardeman et al.

It is certified that error appears in the above-identified patent and that said Letters Patent is hereby corrected as shown below:

Column 29
Lines 24-37

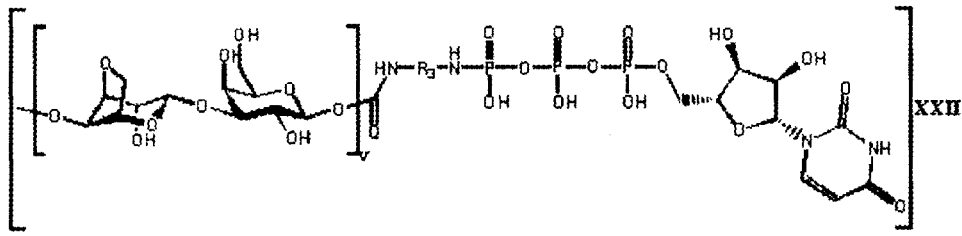

should be

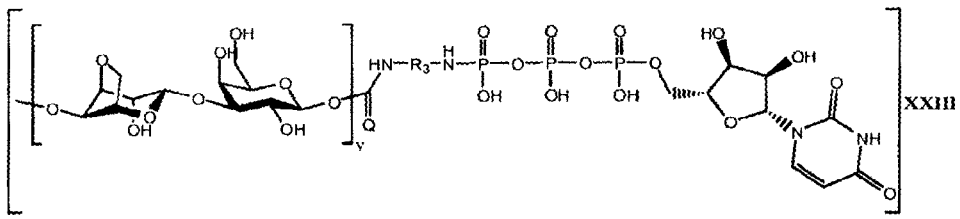

UNITED STATES PATENT AND TRADEMARK OFFICE
CERTIFICATE OF CORRECTION

PATENT NO. : 7,371,852 B2  Page 3 of 4
APPLICATION NO. : 10/762078
DATED : May 13, 2008
INVENTOR(S) : Hardeman et al.

It is certified that error appears in the above-identified patent and that said Letters Patent is hereby corrected as shown below:

Column 64
Lines 51-64

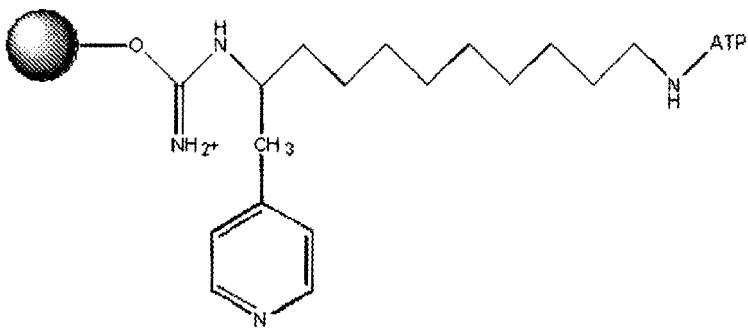

and/or

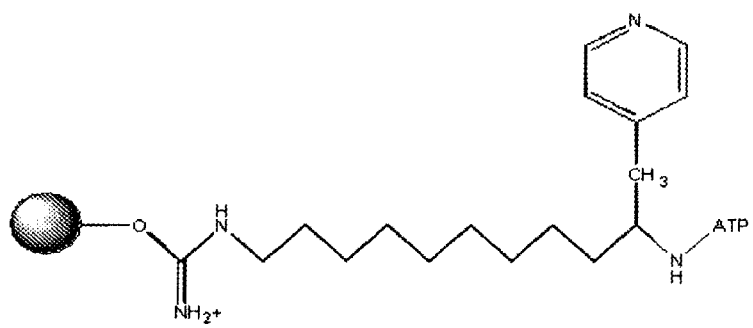

should be

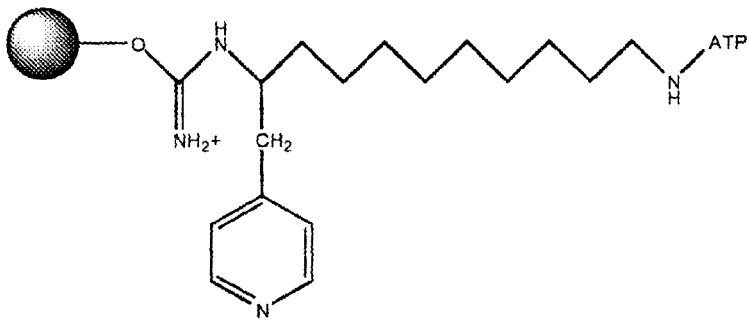

and/or

UNITED STATES PATENT AND TRADEMARK OFFICE
CERTIFICATE OF CORRECTION

PATENT NO. : 7,371,852 B2
APPLICATION NO. : 10/762078
DATED : May 13, 2008
INVENTOR(S) : Hardeman et al.

It is certified that error appears in the above-identified patent and that said Letters Patent is hereby corrected as shown below:

Column 64
Lines 51-64 (con'd)

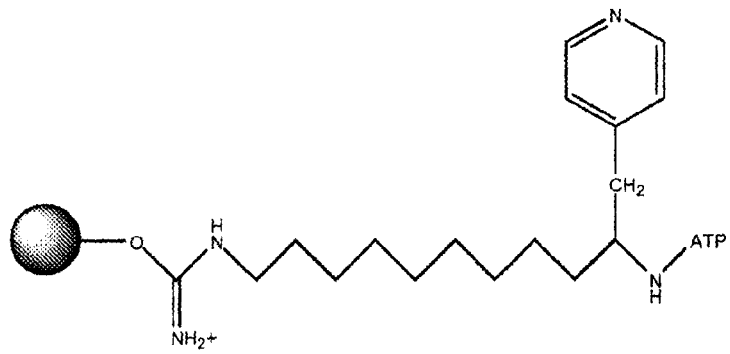

Signed and Sealed this

Second Day of September, 2008

JON W. DUDAS
*Director of the United States Patent and Trademark Office*